United States Patent
Grice et al.

(10) Patent No.: US 11,059,822 B2
(45) Date of Patent: Jul. 13, 2021

(54) MAGL INHIBITORS

(71) Applicant: H. LUNDBECK A/S, Valby (DK)

(72) Inventors: Cheryl A. Grice, Encinitas, CA (US);
Daniel J. Buzard, San Diego, CA (US); Michael B. Shaghafi, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 4 days.

(21) Appl. No.: 16/349,047

(22) PCT Filed: Nov. 15, 2017

(86) PCT No.: PCT/US2017/061870
§ 371 (c)(1),
(2) Date: May 10, 2019

(87) PCT Pub. No.: WO2018/093949
PCT Pub. Date: May 24, 2018

(65) Prior Publication Data
US 2020/0291023 A1    Sep. 17, 2020

Related U.S. Application Data

(60) Provisional application No. 62/423,102, filed on Nov. 16, 2016.

(51) Int. Cl.
*C07D 471/10* (2006.01)
*A61K 31/438* (2006.01)

(52) U.S. Cl.
CPC .................... *C07D 471/10* (2013.01)

(58) Field of Classification Search
CPC .. C07D 471/10; C07D 487/02; A61K 31/438; A61K 31/407
USPC ...................... 546/16; 548/453; 514/278, 412
See application file for complete search history.

(56) References Cited

U.S. PATENT DOCUMENTS

| | | | |
|---|---|---|---|
| 9,133,148 B2 | 9/2015 | Cisar et al. | |
| 9,487,495 B2 | 11/2016 | Cisar et al. | |
| 9,828,379 B2 | 11/2017 | Jones et al. | |
| 1,003,002 A1 | 7/2018 | Cisar et al. | |
| 2005/0234090 A1 | 10/2005 | Colon-Cruz et al. | |
| 2011/0071180 A1 | 3/2011 | Akireddy et al. | |
| 2011/0172230 A1 | 7/2011 | Ishii et al. | |
| 2012/0165422 A1 | 6/2012 | Vernon et al. | |
| 2012/0208812 A1 | 8/2012 | Chai et al. | |
| 2016/0137649 A1 | 5/2016 | Jones et al. | |
| 2016/0272602 A1 | 9/2016 | Cisar et al. | |
| 2017/0029390 A1 | 2/2017 | Butler et al. | |
| 2020/0022977 A1 | 1/2020 | Cisar et al. | |

FOREIGN PATENT DOCUMENTS

| | | |
|---|---|---|
| CL | 2019000661 A1 | 7/2019 |
| CL | 2019000662 A1 | 7/2019 |
| CN | 110267962 A | 9/2019 |
| WO | WO-2010089510 A2 | 8/2010 |
| WO | WO-2010141817 A1 | 12/2010 |
| WO | WO-2011109277 A1 | 9/2011 |
| WO | WO-2011151808 A1 | 12/2011 |
| WO | WO-2012052730 A1 | 4/2012 |
| WO | WO-2013103973 A1 | 7/2013 |
| WO | WO-2014048865 A1 | 4/2014 |
| WO | WO-2015003002 A1 | 1/2015 |
| WO | WO-2016149401 A2 | 9/2016 |
| WO | WO-2017021805 A1 | 2/2017 |
| WO | WO-2017087858 A1 | 5/2017 |
| WO | WO-2017171100 A1 | 10/2017 |
| WO | WO-2017197192 A1 | 11/2017 |
| WO | WO-2018093946 A1 | 5/2018 |
| WO | WO-2018093947 A1 | 5/2018 |
| WO | WO-2018093949 A1 | 5/2018 |
| WO | WO-2018093950 A1 | 5/2018 |
| WO | WO-2018093953 A1 | 5/2018 |
| WO | WO-2019046318 A1 | 3/2019 |
| WO | WO-2019046330 A1 | 3/2019 |

OTHER PUBLICATIONS

Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Brun et al. Drug sensitivity of Chinese Trypanosoma evansi and Trypanosoma equiperdum isolates. Vet. Parasitol. 52:37-46 (1994).
Chang et al. Highly Selective Inhibitors of Monoacylglycerol Lipase Bearing a Reactive Group that is Bioisosteric with Endocannabinoid Substrates. ChemBiol 19(5):579-588 (2012).
Changsen et al. Improved green fluorescent protein reporter gene-based microplate screening for antituberculosis compounds by utilizing an acctamidasc promoter. Antimicrob AgentsChemother 47:3682-3687 (2003).
Chen et al. SAP102 mediates synaptic clearance of NMDA receptors. Cell Rep. 2(5):1120-1128 (2012).
Cho et al. Low-oxygen-recovery assay for high-throughput screening of compounds against nonreplicating Mycobacterium tuberculosis. Antimicrobl AgentsChemother 51:1380-1385 (2007).
Collins et al. Microplate alamar blue assay versus BACTEC 460 system for high-throughput screening of compounds against Mycobacterium tuberculosis and Mycobacterium avium. Antimicrobl Agents Chemother 41:1004-1009 (1997).
Fleisher et al. Improved oral drug delivery: solubility limitations overcome by the use of prodrugs. Advanced Drug Delivery Reviews 19:115-130 (1996).
Long et al. Selective blockade of 2-arachidonoylglycerol hydrolysis produces cannabinoid behavioral effects. Nat Chem Biol. 5(1):37-44 (2009).
Niphakis et al. Evaluation of NHS carbamates as a potent and selective class of endocannabinoid hydrolase inhibitors. ACS Chem Neurosci 4(9):1322-1332 (2013).

(Continued)

*Primary Examiner* — Charanjit Aulakh
(74) *Attorney, Agent, or Firm* — Wilson Sonsini Goodrich & Rosati

(57) ABSTRACT

Provided herein are spirocyclic and fused bicyclic carbamates and pharmaceutical compositions comprising said compounds. The subject compounds and compositions are useful as modulators of MAGL. Furthermore, the subject compounds and compositions are useful for the treatment of pain.

18 Claims, No Drawings

(56) References Cited

OTHER PUBLICATIONS

Niphakis et al.O-Hydroxyacetamide Carbamates as a Highly Potent and Selective Class of Endocannabinoid Hydrolase Inhibitors. ACS Chem. Neurosci. 3(5):418-426 (2012/Web2011).

Nomura et al. Activation of the endocannabinoid system by organophosphorus nerve agents. Nat Chem Biol. 4(6):373-378 (2008).

Nomura et al. Endocannabinoid hydrolysis generates brain prostaglandins that promote neuroinflammation. Science 334(6057):809-813 (2011).

Nomura et al. Monoacylglycerol lipase regulates 2-arachidonoylglycerol action and arachidonic acid levels. Bioorg Med Chem Lett. 18(22):5875-5878 (2008).

PCT/US2014045145 International Preliminary Report on Patentability dated Jan. 14, 2016.

PCT/US2014045145 International Search Report and Written Opinion dated Dec. 10, 2014.

PCT/US2017/032276 International Search Report and Written Opinion dated Sep. 26, 2017.

PCT/US2017/061870 International Search Report and Written Opinion dated Mar. 26, 2018.

PCT/US2017/061870 Invitation to Pay Additional Fees dated Jan. 22, 2018.

Piro et al. A dysregulated endocannabinoid-eicosanoid network supports pathogenesis in a mouse model of Alzheimer's disease. Cell Rep. 1(6):617-623 (2012).

Pubchem, Substance Database, SID 239803465. Retrieved from Internet<URL: https://pubchem.ncbi.nlm.nih.gov/substance/239803465> (7pgs.) (Available Date Feb. 13, 2015) (retrieved Jun. 27, 2017).

Raz et al. The Alamar Blue® assay to determine drug sensitivity of African trypanosomes (T.b. rhodesiense and T.b. gambiense) in vitro. Acta Tropica 68:139-147 (1997).

Snewin et al. Assessment of immunity to mycobacterial infection with luciferase reporter constructs. Infection and Immunity 67:4586-4593 (1999).

U.S. Appl. No. 14/902,324 Office Action dated Dec. 30, 2016.

PCT/US2018/048372 International Search Report and Written Opinion dated Dec. 4, 2018.

PCT/US2018/048372 Invitation to Pay Additional Fees dated Oct. 4, 2018.

PCT/US2018/048388 International Search Report and Written Opinion dated Dec. 4, 2018.

PCT/US2018/048388 Invitation to Pay Additional Fees dated Oct. 4, 2018.

Keith et al. Heteroarylureas with spirocyclic diamine cores as inhibitors of fatty acid amide hydrolase. Bioorg Med Chem Lett 24(3):737-41 (2014).

MAGL INHIBITORS

CROSS-REFERENCE

This application is a U.S. National Stage entry of PCT application PCT/US2017/061,870 filed Nov. 15, 2017, which claims the benefit of U.S. Provisional Application No. 62/423,102, filed on Nov. 16, 2016, which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound of Formula (I):

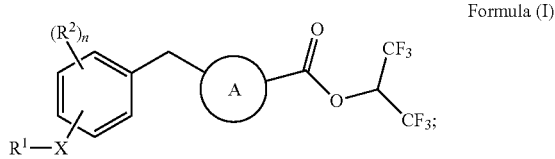

wherein:

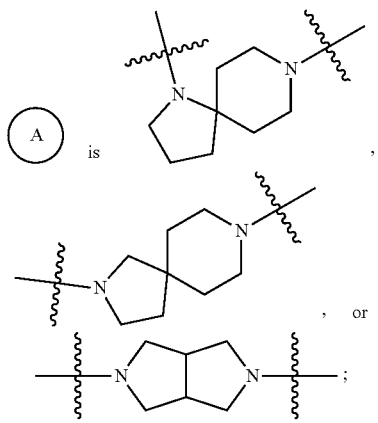

X is —O—, —S—, —SO$_2$—, —N(R$^3$)—, or —CH$_2$—;
Y is —O— or —N(R$^7$)—;
R$^1$ is —(CR$^4$R$^5$)$_m$—R$^6$, —(CR$^4$R$^5$)$_p$—Y—(CR$^4$R$^5$)$_q$—R$^6$, or —(CR$^4$R$^5$)$_t$—C$_{3-6}$cycloalkyl-R$^6$;
each R$^2$ is independently selected from halogen, —CN, C$_{1-6}$alkyl, C$_{1-6}$haloalkyl, —C$_{1-6}$alkyl(heterocycloalkyl), —OR$^{17}$, and —C(O)NR$^{18}$R$^{19}$;
R$^3$ is H or C$_{1-6}$alkyl;
each R$^4$ and R$^5$ is each independently selected from H, F, and C$_{1-6}$alkyl; or R$^4$ and R$^5$, together with the carbon to which they are attached, form a C$_{3-6}$cycloalkyl ring;
R$^6$ is —CO$_2$R$^9$, —C(O)R$^{10}$, or —C(O)O—(CR$^{12}$R$^{13}$)—OC(O)R$^{11}$;
R$^7$ is H, C$_{1-6}$alkyl, or —SO$_2$R$^8$;
R$^8$ is C$_{1-6}$alkyl;
R$^9$ is H or C$_{1-6}$alkyl;
R$^{10}$ is C$_{1-6}$alkyl or —NHSO$_2$R$^{21}$;
R$^{11}$ is C$_{1-6}$alkyl or C$_{1-6}$alkoxy;
R$^{12}$ and R$^{13}$ is each independently H or C$_{1-6}$alkyl;
each R$^{17}$ is independently selected from H, C$_{1-6}$alkyl, C$_{1-6}$haloalkyl, aminoalkyl, cycloalkyl, —C$_{1-6}$alkyl(heterocycloalkyl), —C$_{1-6}$alkyl-C(O)(heterocycloalkyl), optionally substituted heterocycloalkyl, optionally substituted aryl, and optionally substituted heteroaryl;
each R$^{18}$ and R$^{19}$ is independently selected from H, C$_{1-6}$alkyl, C$_{1-6}$haloalkyl, cycloalkyl, aryl, and heteroaryl; or R$^{18}$ and R$^{19}$, together with the nitrogen to which they are attached, form a heterocycloalkyl ring optionally substituted with one, two, or three R$^{20}$; each R$^{20}$ is independently selected from halogen, C$_{1-6}$alkyl, C$_{1-6}$haloalkyl, oxo, —CN, and C$_{3-6}$cycloalkyl;
R$^{21}$ is C$_{1-6}$alkyl;
m is 1, 2, 3 or 4;
n is 0, 1, 2, 3, or 4;
p is 2, 3, or 4;
q is 1, 2, or 3; and
t is 0, 1, or 2;
or a pharmaceutically acceptable salt or solvate thereof.

In some embodiments is a compound of Formula (I), or a pharmaceutically acceptable salt or solvate thereof, wherein R$^1$ is —(CR$^4$R$^5$)$_m$—R$^6$. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein R$^1$ is —(CR$^4$R$^5$)$_p$—Y—(CR$^4$R$^5$)$_q$—R$^6$. In some embodiments is a compound of Formula (I), or a pharmaceutically acceptable salt or solvate thereof, wherein Y is —O—. In some embodiments is a compound of Formula (I), or a pharmaceutically acceptable salt or solvate thereof, wherein Y is —N(R$^7$)—. In some embodiments is a compound of Formula (I), or a pharmaceutically acceptable salt or solvate thereof, wherein R$^7$ is —SO$_2$R$^8$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein R$^1$ is —(CR$^4$R$^5$)$_t$—C$_{3-6}$cycloalkyl-R$^6$. In some embodiments is a compound of Formula (I), or a pharmaceutically acceptable salt or solvate thereof, wherein t is 0. In some embodiments is a compound of Formula (I), or a pharmaceutically acceptable salt or solvate thereof, wherein t is 1. In some embodiments is a compound of Formula (I), or a pharmaceutically acceptable salt or solvate thereof, wherein t is 2. In some embodiments is a compound of Formula (I), or a pharmaceutically acceptable salt or solvate thereof, wherein each $R^4$ and $R^5$ is each independently selected from H and $C_{1-6}$alkyl. In some embodiments is a compound of Formula (I), or a pharmaceutically acceptable salt or solvate thereof, wherein each $R^4$ and $R^5$ is H. In some embodiments is a compound of Formula (I), or a pharmaceutically acceptable salt or solvate thereof, wherein $R^6$ is —C(O)OR$^9$. In some embodiments is a compound of Formula (I), or a pharmaceutically acceptable salt or solvate thereof, wherein $R^9$ is H. In some embodiments is a compound of Formula (I), or a pharmaceutically acceptable salt or solvate thereof, wherein $R^9$ is $C_{1-6}$alkyl. In some embodiments is a compound of Formula (I), or a pharmaceutically acceptable salt or solvate thereof, wherein $R^6$ is —C(O)R$^{10}$. In some embodiments is a compound of Formula (I), or a pharmaceutically acceptable salt or solvate thereof, wherein $R^{10}$ is —NHSO$_2$R$^{21}$. In some embodiments is a compound of Formula (I), or a pharmaceutically acceptable salt or solvate thereof, wherein $R^6$ is —C(O)O—(CR$^{12}$R$^{13}$)—OC(O)R$^{11}$. In some embodiments is a compound of Formula (I), or a pharmaceutically acceptable salt or solvate thereof, wherein $R^{11}$ is $C_{1-6}$alkyl. In some embodiments is a compound of Formula (I), or a pharmaceutically acceptable salt or solvate thereof, wherein $R^1$ is $C_{1-6}$alkoxy. In some embodiments is a compound of Formula (I), or a pharmaceutically acceptable salt or solvate thereof, wherein X is —O—. In some embodiments is a compound of Formula (I), or a pharmaceutically acceptable salt or solvate thereof, wherein X is —SO$_2$—. In some embodiments is a compound of Formula (I), or a pharmaceutically acceptable salt or solvate thereof, wherein X is —N(R$^3$)—. In some embodiments is a compound of Formula (I), or a pharmaceutically acceptable salt or solvate thereof, wherein $R^3$ is H. In some embodiments is a compound of Formula (I), or a pharmaceutically acceptable salt or solvate thereof, wherein $R^3$ is $C_{1-6}$alkyl. In some embodiments is a compound of Formula (I), or a pharmaceutically acceptable salt or solvate thereof, wherein X is —CH$_2$—. In some embodiments is a compound of Formula (I), or a pharmaceutically acceptable salt or solvate thereof, wherein

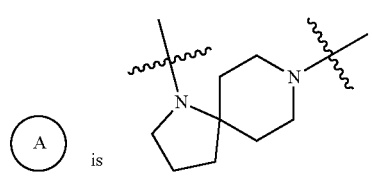

In some embodiments is a compound of Formula (I), or a pharmaceutically acceptable salt or solvate thereof, wherein

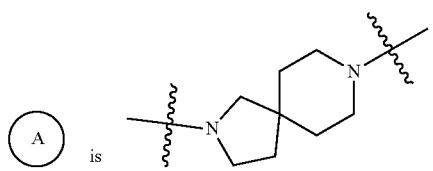

In some embodiments is a compound of Formula (I), or a pharmaceutically acceptable salt or solvate thereof, wherein

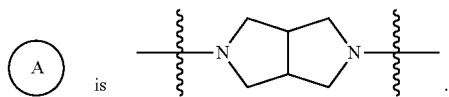

In some embodiments is a compound of Formula (I), or a pharmaceutically acceptable salt or solvate thereof, wherein each $R^2$ is independently selected from halogen, $C_{1-6}$alkyl, and $C_{1-6}$haloalkyl. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein each $R^2$ is —Cl. In some embodiments is a compound of Formula (I), or a pharmaceutically acceptable salt or solvate thereof, wherein each $R^2$ is —CF$_3$.

In another aspect is a compound selected from:

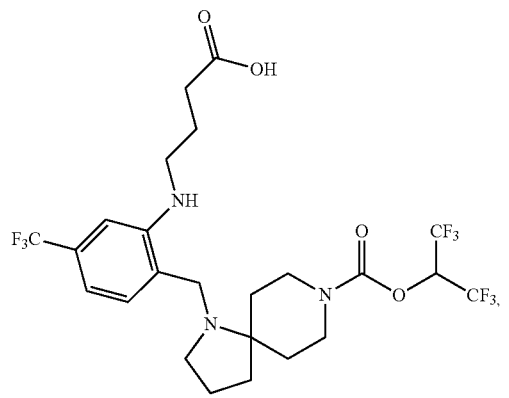

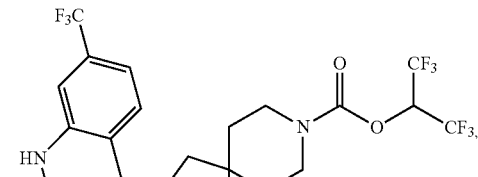

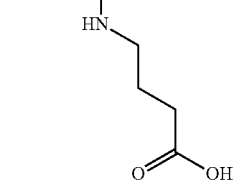

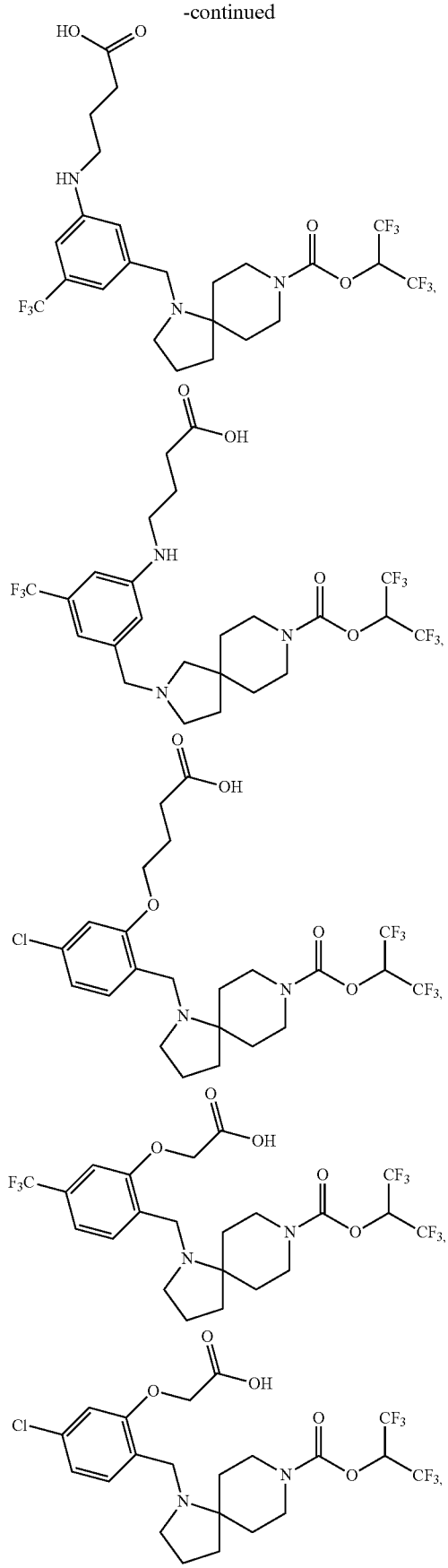
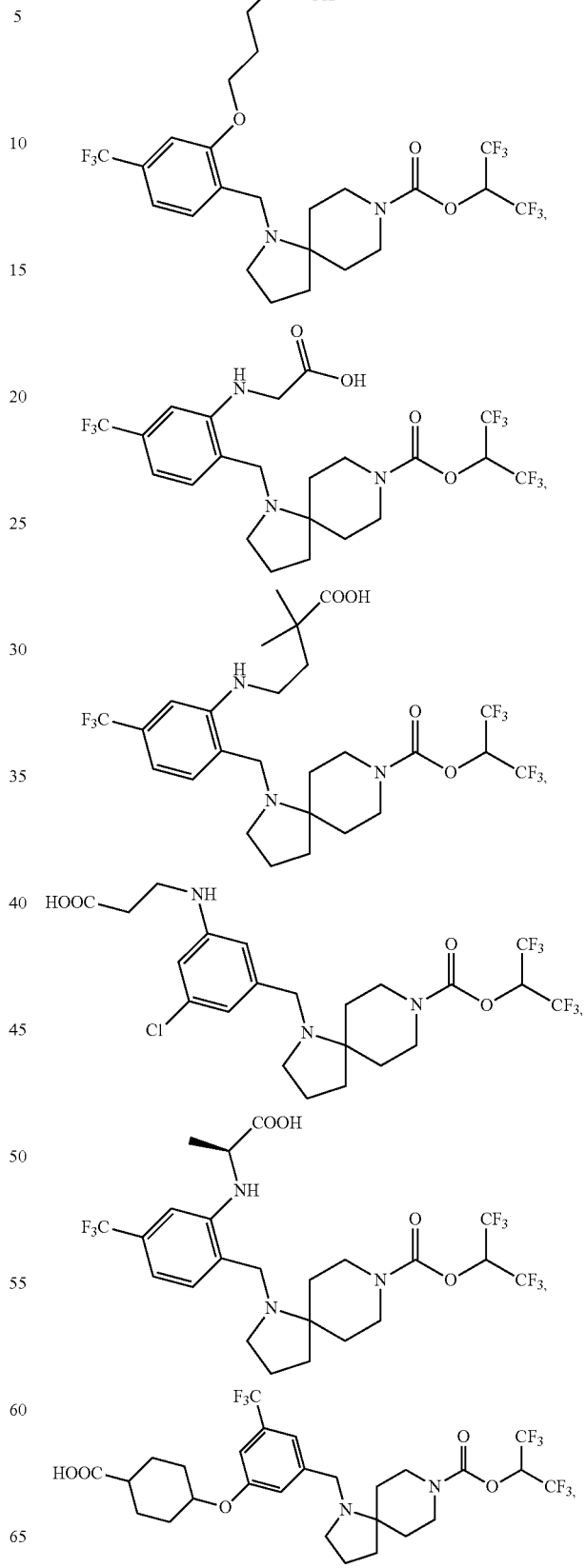

-continued
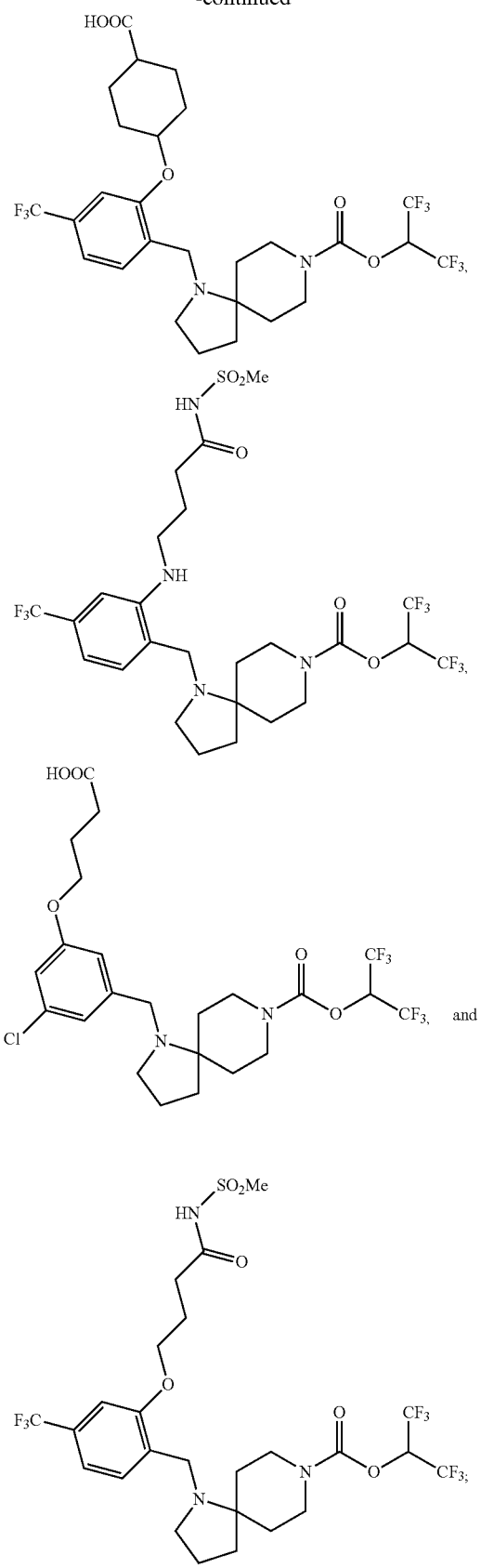
and or a pharmaceutically acceptable salt or solvate thereof.
In another aspect is a compound selected from:
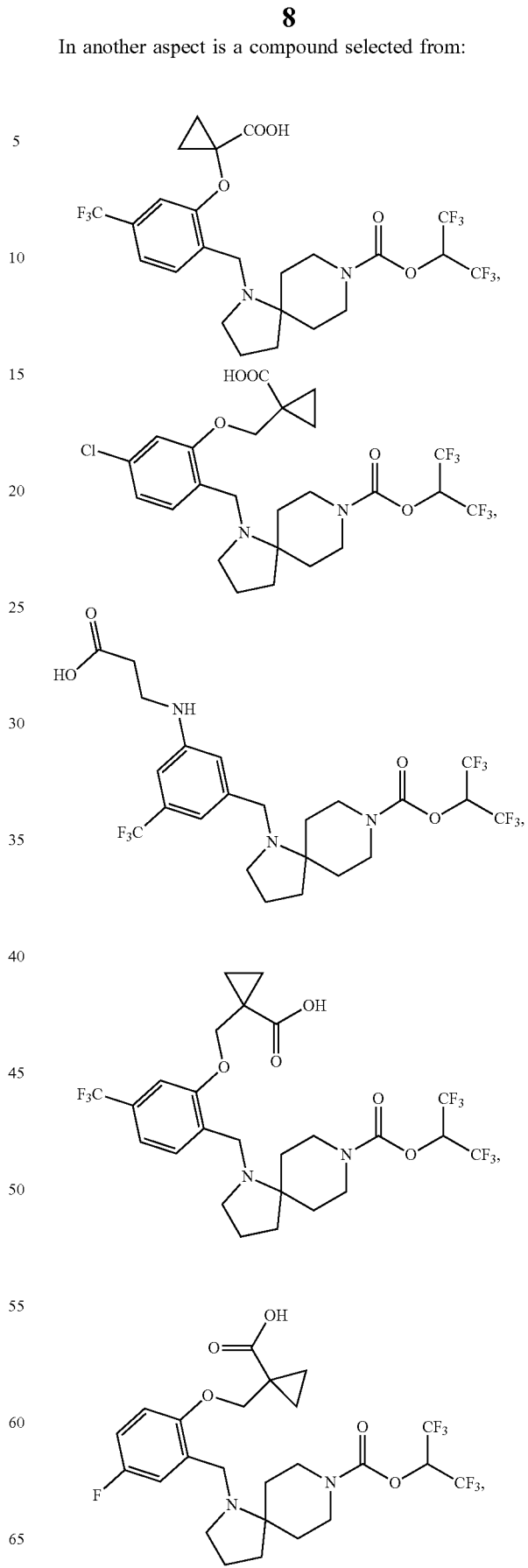

-continued

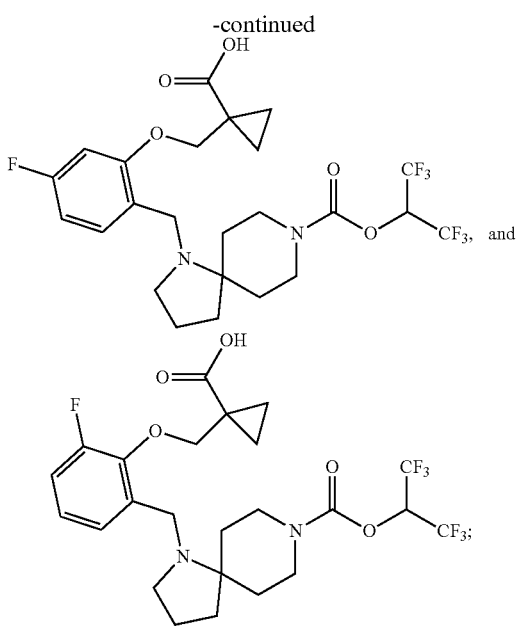

or a pharmaceutically acceptable salt or solvate thereof.

In another embodiment is a pharmaceutical composition comprising a compound of Formula (I) described herein, or a pharmaceutically acceptable salt or solvate thereof, and at least one pharmaceutically acceptable excipient.

In another embodiment is a method of treating pain in a patient in need thereof comprising administering to the patient a therapeutically effective amount of a compound of Formula (I) described herein, or a pharmaceutically acceptable salt or solvate thereof. In some embodiments, the pain is neuropathic pain. In some embodiments, the pain is inflammatory pain.

In another embodiment is a method of treating a disease or disorder in a patient in need thereof comprising administering to the patient a therapeutically effective amount of a compound of Formula (I) described herein, or a pharmaceutically acceptable salt or solvate thereof, wherein the disease or disorder is selected from the group consisting of epilepsy/seizure disorder, multiple sclerosis, neuromyelit is optica (NMO), Tourette syndrome, Alzheimer's disease, and abdominal pain associated with irritable bowel syndrome. In some embodiments, the disease or disorder is epilepsy/seizure disorder. In some embodiments, the disease or disorder is multiple sclerosis. In some embodiments, the disease or disorder is neuromyelit is optica (NMO). In some embodiments, the disease or disorder is Tourette syndrome. In some embodiments, the disease or disorder is Alzheimer's disease. In some embodiments, the disease or disorder is abdominal pain associated with irritable bowel syndrome.

In another embodiment is a method of treating attention deficit and hyperactivity disorder (ADHD) in a patient in need thereof comprising administering to the patient a therapeutically effective amount of a compound of Formula (I) described herein, or a pharmaceutically acceptable salt or solvate thereof.

DETAILED DESCRIPTION OF THE INVENTION

This disclosure is directed, at least in part, to compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within stat is tical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$RR (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^f$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) t-electron system in accordance with the Huckel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Aryloxy" refers to a radical bonded through an oxygen atom of the formula—O—aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) t-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, cit-

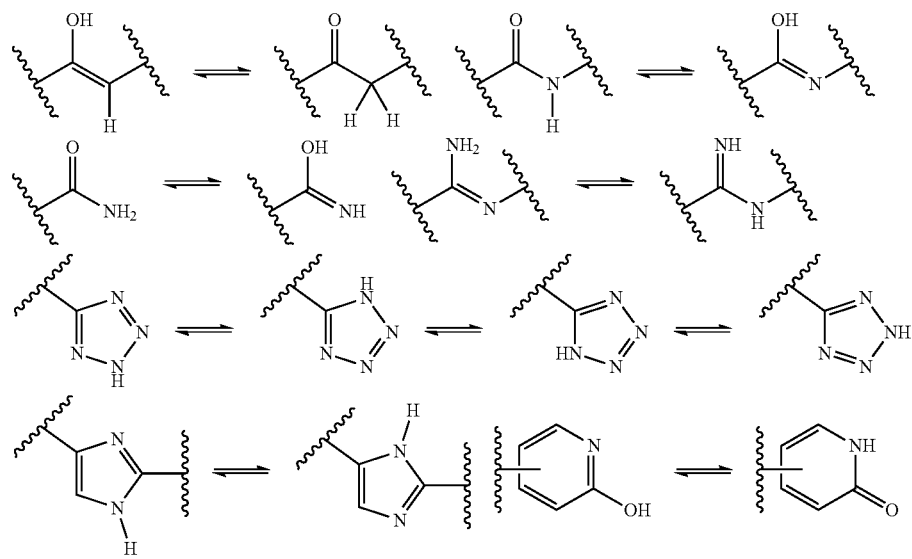

rates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Iaa), (Ib), (Ibb), (Ic), or (Icc) described herein which are modulators of MAGL. These compounds, and compositions comprising these compounds, are useful for the treatment of pain. In some embodiments, the compounds of Formula (I), (Ia), (Iaa), (Ib), (Ibb), (Ic), or (Icc) described herein are useful for treating epilepsy/seizure disorder, multiple sclerosis, neuromyelit is optica (NMO), Tourette syndrome, Alzheimer's disease, or abdominal pain associated with irritable bowel syndrome.

In some embodiments is a compound of Formula (I):

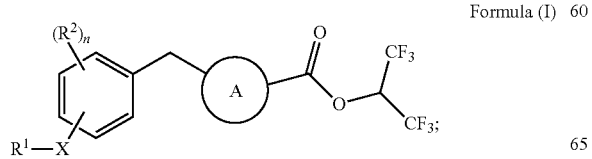

Formula (I)

wherein:

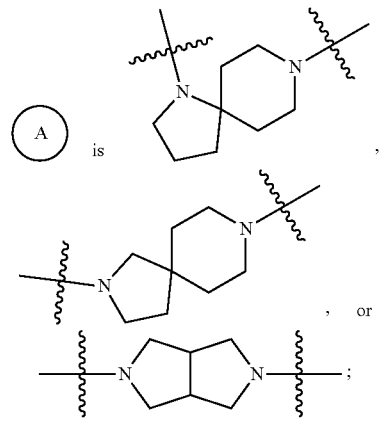

$X$ is —O—, —S—, —SO$_2$—, —N(R$^3$)—, or —CH$_2$—;

$Y$ is —O— or —N(R$^7$)—;

$R^1$ is —(CR$^4$R$^5$)$_m$—R$^6$, —(CR$^4$R$^5$)$_p$—Y—(CR$^4$R$^5$)$_q$—R$^6$, or —(CR$^4$R$^5$)$_t$—C$_{3-6}$cycloalkyl-R$^6$; each R$^2$ is independently selected from halogen, —CN, C$_{1-6}$alkyl, C$_{1-6}$haloalkyl, —C$_{1-6}$alkyl(heterocycloalkyl), —OR$^{17}$, and —C(O)NR$^{18}$R$^{19}$;

$R^3$ is H or C$_{1-6}$alkyl;

each R$^4$ and R$^5$ is each independently selected from H, F, and C$_{1-6}$alkyl; or R$^4$ and R$^5$, together with the carbon to which they are attached, form a C$_{3-6}$cycloalkyl ring;

$R^6$ is —CO$_2$R$^9$, —C(O)R$^{10}$, or —C(O)O—(CR$^{12}$R$^{13}$)—OC(O)R;

$R^7$ is H, C$_{1-6}$alkyl, or —SO$_2$R$^8$;

$R^8$ is C$_{1-6}$alkyl;

$R^9$ is H or C$_{1-6}$alkyl;

$R^{10}$ is C$_{1-6}$alkyl or —NHSO$_2$R$^{21}$;

$R^{11}$ is C$_{1-6}$alkyl or C$_{1-6}$alkoxy;

$R^{12}$ and $R^{13}$ is each independently H or C$_{1-6}$alkyl;

each R$^{17}$ is independently selected from H, C$_{1-6}$alkyl, C$_{1-6}$haloalkyl, aminoalkyl, cycloalkyl, —C$_{1-6}$alkyl(heterocycloalkyl), —C$_{1-6}$alkyl-C(O)(heterocycloalkyl), optionally substituted heterocycloalkyl, optionally substituted aryl, and optionally substituted heteroaryl;

each R$^{18}$ and R$^{19}$ is independently selected from H, C$_{1-6}$alkyl, C$_{1-6}$haloalkyl, cycloalkyl, aryl, and heteroaryl; or R$^{18}$ and R$^{19}$, together with the nitrogen to which they are attached, form a heterocycloalkyl ring optionally substituted with one, two, or three R$^{20}$; each R$^{20}$ is independently selected from halogen, C$_{1-6}$alkyl, C$_{1-6}$haloalkyl, oxo, —CN, and C$_{3-6}$cycloalkyl;

$R^{21}$ is C$_{1-6}$alkyl;

m is 1, 2, 3 or 4;

n is 0, 1, 2, 3, or 4;

p is 2, 3, or 4;

q is 1, 2, or 3; and t is 0, 1, or 2;

or a pharmaceutically acceptable salt or solvate thereof.

In some embodiments is a compound of Formula (I), or a pharmaceutically acceptable salt or solvate thereof, wherein

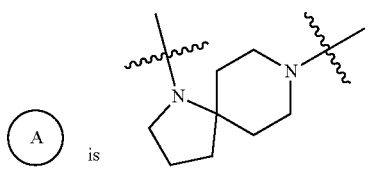

In some embodiments is a compound of Formula (I) or a pharmaceutically acceptable salt or solvate thereof, wherein

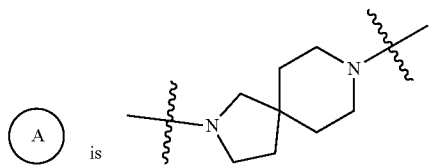

In some embodiments is a compound of Formula (I), or a pharmaceutically acceptable salt or solvate thereof, wherein

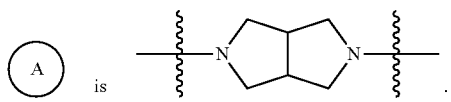

In some embodiments is a compound of Formula (I), or a pharmaceutically acceptable salt or solvate thereof, wherein X is —O—, —S—, —SO$_2$—, —N(R$^3$)—, or —CH$_2$—. In some embodiments is a compound of Formula (I), or a pharmaceutically acceptable salt or solvate thereof, wherein X is —O—. In some embodiments is a compound of Formula (I), or a pharmaceutically acceptable salt or solvate thereof, wherein X is —S—. In some embodiments is a compound of Formula (I), or a pharmaceutically acceptable salt or solvate thereof, wherein X is —SO$_2$—. In some embodiments is a compound of Formula (I), or a pharmaceutically acceptable salt or solvate thereof, wherein X is —N(R$^3$)—. In some embodiments is a compound of Formula (I), or a pharmaceutically acceptable salt or solvate thereof, wherein X is —N(H)—. In some embodiments is a compound of Formula (I), or a pharmaceutically acceptable salt or solvate thereof, wherein X is —N(CH$_3$)—. In some embodiments is a compound of Formula (I), or a pharmaceutically acceptable salt or solvate thereof, wherein X is —N(CH$_2$CH$_3$)—. In some embodiments is a compound of Formula (I), or a pharmaceutically acceptable salt or solvate thereof, wherein X is —CH$_2$—.

In some embodiments is a compound of Formula (I), or a pharmaceutically acceptable salt or solvate thereof, wherein R$^1$ is —(CR$^4$R$^5$)$_m$—R$^6$. In some embodiments is a compound of Formula (I), or a pharmaceutically acceptable salt or solvate thereof, wherein R$^1$ is —(CR$^4$R$^5$)$_m$—R$^6$ and R$^6$ is —CO$_2$R$^9$. In some embodiments is a compound of Formula (I), or a pharmaceutically acceptable salt or solvate thereof, wherein R$^1$ is —(CR$^4$R$^5$)$_m$—R$^6$ and R$^6$ is —CO$_2$H. In some embodiments is a compound of Formula (I), or a pharmaceutically acceptable salt or solvate thereof, wherein R$^1$ is —(CR$^4$R$^5$)$_m$—R$^6$ and R$^6$ is —CO$_2$CH$_3$. In some embodiments is a compound of Formula (I), or a pharmaceutically acceptable salt or solvate thereof, wherein R$^1$ is —(CR$^4$R$^5$)$_m$—R$^6$ and R$^6$ is —CO$_2$CH$_2$CH$_3$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)R$^{10}$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)NHSO$_2$CH$_3$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)O—(CR$^{12}$R$^{13}$)—OC(O)R. In some embodiments is a compound of Formula (I), or a pharmaceutically acceptable salt or solvate thereof, wherein R$^1$ is —(CR$^4$R$^5$)$_m$—R$^6$ and R$^6$ is —C(O)OCH$_2$OC(O)R$^{11}$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)OCH$_2$OC(O)OCH$_2$CH$_3$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)OCH$_2$OC(O)OCH(CH$_3$)$_2$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)OCH$_2$OC(O)OC(CH$_3$)$_3$. In some embodiments is a compound of Formula (I), or a pharmaceutically acceptable salt or solvate thereof, wherein R$^1$ is —(CR$^4$R$^5$)$_m$—R$^6$ and R$^6$ is —C(O)OCH$_2$OC(O)CH(CH$_3$)$_2$. In some embodiments is a compound of Formula (I), or a pharmaceutically acceptable salt or solvate thereof, wherein R$^1$ is —(CR$^4$R$^5$)$_m$—R$^6$ and m is 1. In some embodiments is a compound of Formula (I), or a pharmaceutically acceptable salt or solvate thereof, wherein R$^1$ is —(CR$^4$R$^5$)$_m$—R$^6$ and m is 2. In some embodiments is a compound of Formula (I), or a pharmaceutically acceptable salt or solvate thereof, wherein R$^1$ is —(CR$^4$R$^5$)$_m$—R$^6$ and m is 3. In some embodiments is a compound of Formula (I), or a pharmaceutically acceptable salt or solvate thereof, wherein R$^1$ is —(CR$^4$R$^5$)$_m$—R$^6$ and m is 4. In some embodiments is a compound of Formula (I), or a pharmaceutically acceptable salt or solvate thereof, wherein R$^1$ is —(CR$^4$R$^5$)$_m$—R$^6$ and each R$^4$ and R$^5$ is each independently selected from H and C$_{1-6}$alkyl. In some embodiments is a compound of Formula (I), or a pharmaceutically acceptable salt or solvate thereof, wherein R$^1$ is —(CR$^4$R$^5$)$_m$—R$^6$ and each R$^4$ and R$^5$ is H.

In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 1, and R$^4$ and R$^5$ is independently selected from H and C$_{1-6}$alkyl. In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 2, and each R$^4$ and R$^5$ is each independently selected from H and C$_{1-6}$alkyl. In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 3, and each R$^4$ and R$^5$ is each independently selected from H and C$_{1-6}$alkyl. In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 4, and each R$^4$ and R$^5$ is each independently selected from H and C$_{1-6}$alkyl.

In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 1, and R$^4$ and R$^5$ are H. In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 2, and each R$^4$ and R$^5$ is H. In some embodiments is a compound of Formula (I), or a pharmaceutically acceptable salt or solvate thereof, wherein R$^1$ is —(CR$^4$R$^5$)$_m$—R$^6$, R$^6$ is —CO$_2$H, m is 3, and each R$^4$ and R$^5$ is H. In some embodiments is a compound of Formula (I), or a pharmaceutically acceptable salt or solvate thereof, wherein $R^1$ is $-(CR^4R^5)_m-R^6$, $R^6$ is $-CO_2H$, m is 4, and each $R^4$ and $R^5$ is H.

In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ is independently selected from H and $C_{1-6}$alkyl. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 2, and each $R^4$ and $R^5$ is each independently selected from H and $C_{1-6}$alkyl. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is each independently selected from H and $C_{1-6}$alkyl. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is each independently selected from H and $C_{1-6}$alkyl.

In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ are H. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 2, and each $R^4$ and $R^5$ is H. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is H. In some embodiments is a compound of Formula (I), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is H.

In some embodiments is a compound of Formula (I), or a pharmaceutically acceptable salt or solvate thereof, wherein $R^1$ is $-(CR^4R^5)_p-Y-(CR^4R^5)_q-R^6$. In some embodiments is a compound of Formula (I), or a pharmaceutically acceptable salt or solvate thereof, wherein $R^1$ is $-(CR^4R^5)_p-Y-(CR^4R^5)_q-R^6$ and $R^6$ is $-CO_2R^9$. In some embodiments is a compound of Formula (I), or a pharmaceutically acceptable salt or solvate thereof, wherein $R^1$ is $-(CR^4R^5)_p-Y-(CR^4R^5)_q-R^6$ and $R^6$ is $-CO_2H$. In some embodiments is a compound of Formula (I), or a pharmaceutically acceptable salt or solvate thereof, wherein $R^1$ is $-(CR^4R^5)_p-Y-(CR^4R^5)_q-R^6$ and $R^6$ is $-CO_2CH_3$. In some embodiments is a compound of Formula (I), or a pharmaceutically acceptable salt or solvate thereof, wherein $R^1$ is $-(CR^4R^5)_p-Y-(CR^4R^5)_q-R^6$ and $R^6$ is $-CO_2CH_2CH_3$. In some embodiments is a compound of Formula (I), or a pharmaceutically acceptable salt or solvate thereof, wherein $R^1$ is $-(CR^4R^5)_p-Y-(CR^4R^5)_q-R^6$ and Y is $-O-$. In some embodiments is a compound of Formula (I), or a pharmaceutically acceptable salt or solvate thereof, wherein $R^1$ is $-(CR^4R^5)_p-Y-(CR^4R^5)_q-R^6$ and Y is $-N(R^7)-$. In some embodiments is a compound of Formula (I), or a pharmaceutically acceptable salt or solvate thereof, wherein $R^1$ is $-(CR^4R^5)_p-Y-(CR^4R^5)_q-R^6$ and Y is $-N(H)-$. In some embodiments is a compound of Formula (I), or a pharmaceutically acceptable salt or solvate thereof, wherein $R^1$ is $-(CR^4R^5)_p-Y-(CR^4R^5)_q-R^6$ and Y is $-N(SO_2Me)-$. In some embodiments is a compound of Formula (I), or a pharmaceutically acceptable salt or solvate thereof, wherein $R^1$ is $-(CR^4R^5)_p-Y-(CR^4R^5)_q-R^6$ and p is 2. In some embodiments is a compound of Formula (I), or a pharmaceutically acceptable salt or solvate thereof, wherein $R^1$ is $-(CR^4R^5)_p-Y-(CR^4R^5)_q-R^6$ and p is 3. In some embodiments is a compound of Formula (I), or a pharmaceutically acceptable salt or solvate thereof, wherein $R^1$ is $-(CR^4R^5)_p-Y-(CR^4R^5)_q-R^6$ and p is 4. In some embodiments is a compound of Formula (I), or a pharmaceutically acceptable salt or solvate thereof, wherein $R^1$ is $-(CR^4R^5)_p-Y-(CR^4R^5)_q-R^6$ and q is 1. In some embodiments is a compound of Formula (I), or a pharmaceutically acceptable salt or solvate thereof, wherein $R^1$ is $-(CR^4R^5)_p-Y-(CR^4R^5)_q-R^6$ and q is 2. In some embodiments is a compound of Formula (I), or a pharmaceutically acceptable salt or solvate thereof, wherein $R^1$ is $-(CR^4R^5)_p-Y-(CR^4R^5)_q-R^6$ and q is 3. In some embodiments is a compound of Formula (I), or a pharmaceutically acceptable salt or solvate thereof, wherein $R^1$ is $-(CR^4R^5)_p-Y-(CR^4R^5)_q-R^6$ and each $R^4$ and $R^5$ is each independently selected from H and $C_{1-6}$alkyl. In some embodiments is a compound of Formula (I), or a pharmaceutically acceptable salt or solvate thereof, wherein $R^1$ is $-(CR^4R^5)_p-Y-(CR^4R^5)_q-R^6$ and each $R^4$ and $R^5$ is H.

In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ is independently selected from H and $C_{1-6}$alkyl. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is each independently selected from H and $C_{1-6}$alkyl. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is each independently selected from H and $C_{1-6}$alkyl.

In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ are H. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is H. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is H.

In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ is independently selected from H and $C_{1-6}$alkyl. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(H)-$, p is 2, q is 1, and each $R^4$ and $R^5$ is each independently selected from H and $C_{1-6}$alkyl. In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(SO_2Me)-$, p is 2, q is 1, and each $R^4$ and $R^5$ is each independently selected from H and $C_{1-6}$alkyl.

In some embodiments is a compound of Formula (I), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ are H. In some embodiments is a compound of Formula (I), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —N(H)—, p is 2, q is 1, and each $R^4$ and $R^5$ is H. In some embodiments is a compound of Formula (I), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —N($SO_2$Me)—, p is 2, q is 1, and each $R^4$ and $R^5$ is H.

In some embodiments is a compound of Formula (I), or a pharmaceutically acceptable salt or solvate thereof, wherein $R^1$ is —$(CR^4R^5)_t$—$C_{3-6}$cycloalkyl-$R^6$. In some embodiments is a compound of Formula (I), or a pharmaceutically acceptable salt or solvate thereof, wherein $R^1$ is —$(CR^4R^5)_t$-cyclopropyl-$R^6$. In some embodiments is a compound of Formula (I), or a pharmaceutically acceptable salt or solvate thereof, wherein $R^1$ is —$(CR^4R^5)_t$-cyclobutyl-$R^6$. In some embodiments is a compound of Formula (I), or a pharmaceutically acceptable salt or solvate thereof, wherein $R^1$ is —$(CR^4R^5)_t$-cyclopentyl-$R^6$. In some embodiments is a compound of Formula (I), or a pharmaceutically acceptable salt or solvate thereof, wherein $R^1$ is —$(CR^4R^5)_t$-cyclohexyl-$R^6$. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and $R^6$ is —$CO_2R^9$. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and $R^6$ is —$CO_2H$. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and $R^6$ is —$CO_2CH_3$. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and $R^6$ is —$CO_2CH_2CH_3$. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and t is 0. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and t is 1. In some embodiments is a compound of Formula (I), or a pharmaceutically acceptable salt or solvate thereof, wherein $R^1$ is —$(CR^4R^5)_t$—$C_{3-6}$cycloalkyl-$R^6$ and t is 2.

In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 0, and $R^4$ and $R^5$ is independently selected from H and $C_{1-6}$alkyl. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 1, and each $R^4$ and $R^5$ is each independently selected from H and $C_{1-6}$alkyl. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 2, and each $R^4$ and $R^5$ is each independently selected from H and $C_{1-6}$alkyl.

In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 0, and $R^4$ and $R^5$ are H. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 1, and each $R^4$ and $R^5$ is H. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 2, and each $R^4$ and $R^5$ is H.

In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 0, and $R^4$ and $R^5$ is independently selected from H and $C_{1-6}$alkyl. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 1, and each $R^4$ and $R^5$ is each independently selected from H and $C_{1-6}$alkyl. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 2, and each $R^4$ and $R^5$ is each independently selected from H and $C_{1-6}$alkyl.

In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 0, and $R^4$ and $R^5$ are H. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 1, and each $R^4$ and $R^5$ is H. In some embodiments is a compound of Formula (I), or a pharmaceutically acceptable salt or solvate thereof, wherein $R^1$ is —$(CR^4R^5)_t$—$C_{3-6}$cycloalkyl-$R^6$, $R^6$ is —$CO_2R^9$, $R^9$ is $C_{1-6}$alkyl, t is 2, and each $R^4$ and $R^5$ is H.

In some embodiments is a compound of Formula (I), or a pharmaceutically acceptable salt or solvate thereof, wherein —X—$R^1$ is —$OCH_2C(O)OH$. In some embodiments is a compound of Formula (I), or a pharmaceutically acceptable salt or solvate thereof, wherein —X—$R^1$ is —$N(H)CH_2C(O)OH$. In some embodiments is a compound of Formula (I), or a pharmaceutically acceptable salt or solvate thereof, wherein —X—$R^1$ is —$OCH(CH_3)C(O)OH$. In some embodiments is a compound of Formula (I), or a pharmaceutically acceptable salt or solvate thereof, wherein —X—$R^1$ is —$N(H)CH(CH_3)C(O)OH$. In some embodiments is a compound of Formula (I), or a pharmaceutically acceptable salt or solvate thereof, wherein —X—$R^1$ is —$OCH_2CH_2C(O)OH$. In some embodiments is a compound of Formula (I), or a pharmaceutically acceptable salt or solvate thereof, wherein —X—$R^1$ is —$N(H)CH_2CH_2C(O)OH$. In some embodiments is a compound of Formula (I), or a pharmaceutically acceptable salt or solvate thereof, wherein —X—$R^1$ is —$OCH_2CH_2CH_2C(O)OH$. In some embodiments is a compound of Formula (I), or a pharmaceutically acceptable salt or solvate thereof, wherein —X—$R^1$ is —$N(H)CH_2CH_2CH_2C(O)OH$. In some embodiments is a compound of Formula (I), or a pharmaceutically acceptable salt or solvate thereof, wherein —X—$R^1$ is —$OCH_2CH_2C(CH_3)_2C(O)OH$. In some embodiments is a compound of Formula (I), or a pharmaceutically acceptable salt or solvate thereof, wherein —X—$R^1$ is —$N(H)CH_2CH_2C(CH_3)_2C(O)OH$.

In some embodiments is a compound of Formula (I), or a pharmaceutically acceptable salt or solvate thereof, wherein —X—$R^1$ is —$OCH_2C(O)OCH_3$. In some embodiments is a compound of Formula (I), or a pharmaceutically acceptable salt or solvate thereof, wherein —X—$R^1$ is —$N(H)CH_2C(O)OCH_3$. In some embodiments is a compound of Formula (I), or a pharmaceutically acceptable salt or solvate thereof, wherein —X—$R^1$ is —$OCH(CH_3)C(O)OCH_3$. In some embodiments is a compound of Formula (I), or a pharmaceutically acceptable salt or solvate thereof, wherein —X—$R^1$ is —$N(H)CH(CH_3)C(O)OCH_3$. In some embodiments is a compound of Formula (I), or a pharmaceutically acceptable salt or solvate thereof, wherein —X—$R^1$ is —OCH$_2$CH$_2$C(O)OCH$_3$. In some embodiments is a compound of Formula (I), or a pharmaceutically acceptable salt or solvate thereof, wherein —X—R$^1$ is —N(H)CH$_2$CH$_2$C(O)OCH$_3$. In some embodiments is a compound of Formula (I), or a pharmaceutically acceptable salt or solvate thereof, wherein —X—R$^1$ is —OCH$_2$CH$_2$CH$_2$C(O)OCH$_3$. In some embodiments is a compound of Formula (I), or a pharmaceutically acceptable salt or solvate thereof, wherein —X—R$^1$ is —N(H)CH$_2$CH$_2$CH$_2$C(O)OCH$_3$. In some embodiments is a compound of Formula (I), or a pharmaceutically acceptable salt or solvate thereof, wherein —X—R$^1$ is —OCH$_2$CH$_2$C(CH$_3$)$_2$C(O)OCH$_3$. In some embodiments is a compound of Formula (I), or a pharmaceutically acceptable salt or solvate thereof, wherein —X—R$^1$ is —N(H)CH$_2$CH$_2$C(CH$_3$)$_2$C(O)OCH$_3$.

In some embodiments is a compound of Formula (I), or a pharmaceutically acceptable salt or solvate thereof, wherein —X—R$^1$ is —OCH$_2$CH$_2$OCH$_2$C(O)OH. In some embodiments is a compound of Formula (I), or a pharmaceutically acceptable salt or solvate thereof, wherein —X—R$^1$ is —N(H)CH$_2$CH$_2$OCH$_2$C(O)OH. In some embodiments is a compound of Formula (I), or a pharmaceutically acceptable salt or solvate thereof, wherein —X—R$^1$ is —OCH$_2$CH$_2$N(H)CH$_2$C(O)OH. In some embodiments is a compound of Formula (I), or a pharmaceutically acceptable salt or solvate thereof, wherein —X—R$^1$ is —N(H)CH$_2$CH$_2$N(SO$_2$CH$_3$)CH$_2$C(O)OH. In some embodiments is a compound of Formula (I), or a pharmaceutically acceptable salt or solvate thereof, wherein —X—R$^1$ is —OCH$_2$CH$_2$CH$_2$C(O)OCH(CH$_3$)OC(O)OCH$_2$CH$_3$. In some embodiments is a compound of Formula (I), or a pharmaceutically acceptable salt or solvate thereof, wherein —X—R$^1$ is —N(H)CH$_2$CH$_2$CH$_2$C(O)OCH(CH$_3$)OC(O)OCH(CH$_3$)$_2$. In some embodiments is a compound of Formula (I), or a pharmaceutically acceptable salt or solvate thereof, wherein —X—R$^1$ is —OCH$_2$CH$_2$CH$_2$C(O)OCH$_2$OC(O)OC(CH$_3$)$_3$. In some embodiments is a compound of Formula (I), or a pharmaceutically acceptable salt or solvate thereof, wherein —X—R$^1$ is —N(H)CH$_2$CH$_2$CH$_2$C(O)OCH(CH$_3$)OC(O)CH(CH$_3$)$_2$.

In some embodiments is a compound of Formula (I), or a pharmaceutically acceptable salt or solvate thereof, wherein —X—R$^1$ is —O-cyclopropyl-C(O)OH. In some embodiments is a compound of Formula (I), or a pharmaceutically acceptable salt or solvate thereof, wherein —X—R$^1$ is —N(H)-cyclopropyl-C(O)OH. In some embodiments is a compound of Formula (I), or a pharmaceutically acceptable salt or solvate thereof, wherein —X—R$^1$ is —O-cyclobutyl-C(O)OH. In some embodiments is a compound of Formula (I), or a pharmaceutically acceptable salt or solvate thereof, wherein —X—R$^1$ is —N(H)-cyclobutyl-C(O)OH.

In some embodiments is a compound of Formula (I), or a pharmaceutically acceptable salt or solvate thereof, wherein n is 0, 1, 2, or 3. In some embodiments is a compound of Formula (I), or a pharmaceutically acceptable salt or solvate thereof, wherein n is 0, 1, or 2. In some embodiments is a compound of Formula (I), or a pharmaceutically acceptable salt or solvate thereof, wherein n is 1 or 2. In some embodiments is a compound of Formula (I), or a pharmaceutically acceptable salt or solvate thereof, wherein n is 0 or 1. In some embodiments is a compound of Formula (I), or a pharmaceutically acceptable salt or solvate thereof, wherein n is 0. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein n is 3. In some embodiments is a compound of Formula (I), or a pharmaceutically acceptable salt or solvate thereof, wherein n is 4.

In some embodiments is a compound of Formula (I), or a pharmaceutically acceptable salt or solvate thereof, wherein n is 1 and R$^2$ is halogen, C$_{1-6}$alkyl, C$_{1-6}$haloalkyl, or —OR$^{17}$. In some embodiments is a compound of Formula (I), or a pharmaceutically acceptable salt or solvate thereof, wherein n is 1 and R$^2$ is halogen, C$_{1-6}$alkyl, or C$_{1-6}$haloalkyl. In some embodiments is a compound of Formula (I), or a pharmaceutically acceptable salt or solvate thereof, wherein n is 1 and R$^2$ is halogen. In some embodiments is a compound of Formula (I), or a pharmaceutically acceptable salt or solvate thereof, wherein n is 1 and R$^2$ is —Cl. In some embodiments is a compound of Formula (I), or a pharmaceutically acceptable salt or solvate thereof, wherein n is 1 and R$^2$ is —F. In some embodiments is a compound of Formula (I), or a pharmaceutically acceptable salt or solvate thereof, wherein n is 1 and R$^2$ is C$_{1-6}$alkyl. In some embodiments is a compound of Formula (I), or a pharmaceutically acceptable salt or solvate thereof, wherein n is 1 and R$^2$ is —CH$_3$. In some embodiments is a compound of Formula (I), or a pharmaceutically acceptable salt or solvate thereof, wherein n is 1 and R$^2$ is C$_{1-6}$haloalkyl. In some embodiments is a compound of Formula (I), or a pharmaceutically acceptable salt or solvate thereof, wherein n is 1 and R$^2$ is —CF$_3$. In some embodiments is a compound of Formula (I), or a pharmaceutically acceptable salt or solvate thereof, wherein n is 1 and R$^2$ is C$_{1-6}$alkoxy. In some embodiments is a compound of Formula (I), or a pharmaceutically acceptable salt or solvate thereof, wherein n is 1 and R$^2$ is —OCH$_3$. In some embodiments is a compound of Formula (I), or a pharmaceutically acceptable salt or solvate thereof, wherein n is 1 and R$^2$ is C$_{1-6}$haloalkoxy. In some embodiments is a compound of Formula (I), or a pharmaceutically acceptable salt or solvate thereof, wherein n is 1 and R$^2$ is —OCF$_3$. In some embodiments is a compound of Formula (I), or a pharmaceutically acceptable salt or solvate thereof, wherein n is 1 and R$^2$ is —OH. In some embodiments is a compound of Formula (I), or a pharmaceutically acceptable salt or solvate thereof, wherein n is 1 and R$^2$ is —CN.

In some embodiments is a compound of Formula (I), or a pharmaceutically acceptable salt or solvate thereof, wherein n is 2 and each R$^2$ is independently halogen, C$_{1-6}$alkyl, C$_{1-6}$haloalkyl, or —OR$^{17}$. In some embodiments is a compound of Formula (I), or a pharmaceutically acceptable salt or solvate thereof, wherein n is 2 and each R$^2$ is independently halogen, C$_{1-6}$alkyl, C$_{1-6}$haloalkyl, C$_{1-6}$alkoxy, C$_{1-6}$haloalkoxy, —OH, or —CN. In some embodiments is a compound of Formula (I), or a pharmaceutically acceptable salt or solvate thereof, wherein n is 2 and each R$^2$ is independently halogen, C$_{1-6}$alkyl, C$_{1-6}$haloalkyl, C$_{1-6}$alkoxy, —OCF$_3$, or —CN. In some embodiments is a compound of Formula (I), or a pharmaceutically acceptable salt or solvate thereof, wherein n is 2 and each R$^2$ is independently halogen, C$_{1-6}$alkyl, C$_{1-6}$haloalkyl, C$_{1-6}$alkoxy, or —OCF$_3$. In some embodiments is a compound of Formula (I), or a pharmaceutically acceptable salt or solvate thereof, wherein n is 2 and each R$^2$ is independently halogen, C$_{1-6}$alkyl, C$_{1-6}$haloalkyl, or —OCF$_3$. In some embodiments is a compound of Formula (I), or a pharmaceutically acceptable salt or solvate thereof, wherein n is 2 and each R$^2$ is independently halogen, C$_{1-6}$alkyl, or C$_{1-6}$haloalkyl. In some embodiments is a compound of Formula (I), or a pharmaceutically acceptable salt or solvate thereof, wherein n is 2 and each R$^2$ is independently halogen or $C_{1-6}$haloalkyl. In some embodiments is a compound of Formula (I), or a pharmaceutically acceptable salt or solvate thereof, wherein n is 2 and each $R^2$ is independently halogen or $C_{1-6}$alkyl. In some embodiments is a compound of Formula (I), or a pharmaceutically acceptable salt or solvate thereof, wherein n is 2 and each $R^2$ is independently halogen. In some embodiments is a compound of Formula (I), or a pharmaceutically acceptable salt or solvate thereof, wherein n is 2 and each $R^2$ is independently $C_{1-6}$alkyl. In some embodiments is a compound of Formula (I), or a pharmaceutically acceptable salt or solvate thereof, wherein n is 2 and each $R^2$ is independently $C_{1-6}$haloalkyl.

In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, or —$OR^{17}$. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —$OCF_3$, or —CN. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —$OCF_3$. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, or —$OCF_3$. In some embodiments is a compound of Formula (I), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (I), or a pharmaceutically acceptable salt or solvate thereof, wherein n is 3 and each $R^2$ is independently halogen or $C_{1-6}$haloalkyl. In some embodiments is a compound of Formula (I), or a pharmaceutically acceptable salt or solvate thereof, wherein n is 3 and each $R^2$ is independently halogen or $C_{1-6}$alkyl. In some embodiments is a compound of Formula (I), or a pharmaceutically acceptable salt or solvate thereof, wherein n is 3 and each $R^2$ is independently halogen. In some embodiments is a compound of Formula (I), or a pharmaceutically acceptable salt or solvate thereof, wherein n is 3 and each $R^2$ is independently $C_{1-6}$alkyl. In some embodiments is a compound of Formula (I), or a pharmaceutically acceptable salt or solvate thereof, wherein n is 3 and each $R^2$ is independently $C_{1-6}$haloalkyl.

In some embodiments is a compound of Formula (I), or a pharmaceutically acceptable salt or solvate thereof, wherein n is 4 and each $R^2$ is independently halogen, $C_{1-6}$alkyl, $C_{1-6}$haloalkyl, and —$OR^{17}$.

In some embodiments is a compound of Formula (Ia):

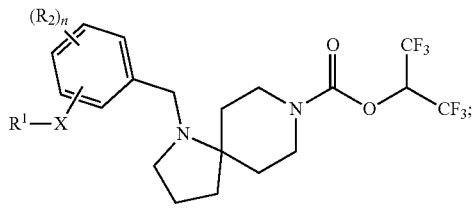

Formula (Ia)

wherein:
X is —O—, —S—, —$SO_2$—, —$N(R^3)$—, or —$CH_2$—;
Y is —O— or —$N(R^7)$—;
$R^1$ is —$(CR^4R^5)_m$—$R^6$, —$(CR^4R^5)_p$—Y—$(CR^4R^5)_q$—$R^6$, or —$(CR^4R^5)_t$—$C_{3-6}$cycloalkyl-$R^6$;
each $R^2$ is independently selected from halogen, —CN, $C_{1-6}$alkyl, $C_{1-6}$haloalkyl, —$C_{1-6}$alkyl(heterocycloalkyl), —$OR^{17}$, and —$C(O)NR^{18}R^{19}$;
$R^3$ is H or $C_{1-6}$alkyl;
each $R^4$ and $R^5$ is each independently selected from H, F, and $C_{1-6}$alkyl; or $R^4$ and $R^5$, together with the carbon to which they are attached, form a $C_{3-6}$cycloalkyl ring;
$R^6$ is —$CO_2R^9$, —$C(O)R^{10}$, or —$C(O)O$—$(CR^{12}R^{13})$—$OC(O)R^{11}$;
$R^7$ is H, $C_{1-6}$alkyl, or —$SO_2R^8$;
$R^8$ is $C_{1-6}$alkyl;
$R^9$ is H or $C_{1-6}$alkyl;
$R^{10}$ is $C_{1-6}$alkyl or —$NHSO_2R^{21}$;
$R^{11}$ is $C_{1-6}$alkyl or $C_{1-6}$alkoxy;
$R^{12}$ and $R^{13}$ is each independently H or $C_{1-6}$alkyl;
each $R^{17}$ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl-$C(O)$(heterocycloalkyl), optionally substituted heterocycloalkyl, optionally substituted aryl, and optionally substituted heteroaryl;
each $R^{18}$ and $R^{19}$ is independently selected from H, $C_{1-6}$alkyl, $C_{1-6}$haloalkyl, cycloalkyl, aryl, and heteroaryl; or $R^{18}$ and $R^{19}$, together with the nitrogen to which they are attached, form a heterocycloalkyl ring optionally substituted with one, two, or three $R^{20}$; each $R^{20}$ is independently selected from halogen, $C_{1-6}$alkyl, $C_{1-6}$haloalkyl, oxo, —CN, and $C_{3-6}$cycloalkyl;
$R^{21}$ is $C_{1-6}$alkyl;
m is 1, 2, 3 or 4;
n is 0, 1, 2, 3, or 4;
p is 2, 3, or 4;
q is 1, 2, or 3; and
t is 0, 1, or 2;
or a pharmaceutically acceptable salt or solvate thereof.

In some embodiments is a compound of Formula (Ia), or a pharmaceutically acceptable salt or solvate thereof, wherein X is —O—, —S—, —$SO_2$—, —$N(R^3)$—, or —$CH_2$—. In some embodiments is a compound of Formula (Ia), or a pharmaceutically acceptable salt or solvate thereof, wherein X is —O—. In some embodiments is a compound of Formula (Ia), or a pharmaceutically acceptable salt or solvate thereof, wherein X is —S—. In some embodiments is a compound of Formula (Ia), or a pharmaceutically acceptable salt or solvate thereof, wherein X is —$SO_2$—. In some embodiments is a compound of Formula (Ia), or a pharmaceutically acceptable salt or solvate thereof, wherein X is —$N(R^3)$—. In some embodiments is a compound of Formula (Ia), or a pharmaceutically acceptable salt or solvate thereof, wherein X is —N(H)—. In some embodiments is a compound of Formula (Ia), or a pharmaceutically acceptable salt or solvate thereof, wherein X is —$N(CH_3)$—. In some embodiments is a compound of Formula (Ia), or a pharmaceutically acceptable salt or solvate thereof, wherein X is —$N(CH_2CH_3)$—. In some embodiments is a compound of Formula (Ia), or a pharmaceutically acceptable salt or solvate thereof, wherein X is —$CH_2$—.

In some embodiments is a compound of Formula (Ia), or a pharmaceutically acceptable salt or solvate thereof, wherein $R^1$ is —$(CR^4R^5)_m$—$R^6$. In some embodiments is a compound of Formula (Ia), or a pharmaceutically acceptable salt or solvate thereof, wherein $R^1$ is —$(CR^4R^5)_m$—$R^6$ and $R^6$ is —$CO_2R^9$. In some embodiments is a compound of Formula (Ia), or a pharmaceutically acceptable salt or solvate thereof, wherein $R^1$ is —$(CR^4R^5)_m$—$R^6$ and $R^6$ is —$CO_2H$. In some embodiments is a compound of Formula (Ia), or a pharmaceutically acceptable salt or solvate thereof, wherein $R^1$ is —$(CR^4R^5)_m$—$R^6$ and $R^6$ is —$CO_2CH_3$. In some embodiments is a compound of Formula (Ia), or a pharmaceutically acceptable salt or solvate thereof, wherein $R^1$ is —$(CR^4R^5)_m$—$R^6$ and $R^6$ is —$CO_2CH_2CH_3$. In some embodiments is a compound of Formula (Ia), or a pharmaceutically acceptable salt or solvate thereof, wherein $R^1$ is —$(CR^4R^5)_m$—$R^6$ and $R^6$ is —$C(O)R^{10}$. In some embodiments is a compound of Formula (Ia), or a pharmaceutically acceptable salt or solvate thereof, wherein $R^1$ is —$(CR^4R^5)_m$—$R^6$ and $R^6$ is —$C(O)NHSO_2CH_3$. In some embodiments is a compound of Formula (Ia), or a pharmaceutically acceptable salt or solvate thereof, wherein $R^1$ is —$(CR^4R^5)_m$—$R^6$ and $R^6$ is —$C(O)O$—$(CR^{12}R^{13})$—$OC(O)R^1$. In some embodiments is a compound of Formula (Ia), or a pharmaceutically acceptable salt or solvate thereof, wherein $R^1$ is —$(CR^4R^5)_m$—$R^6$ and $R^6$ is —$C(O)OCH_2OC(O)R^{11}$. In some embodiments is a compound of Formula (Ia), or a pharmaceutically acceptable salt or solvate thereof, wherein $R^1$ is —$(CR^4R^5)_m$—$R^6$ and $R^6$ is —$C(O)OCH_2OC(O)OCH_2CH_3$. In some embodiments is a compound of Formula (Ia), or a pharmaceutically acceptable salt or solvate thereof, wherein $R^1$ is —$(CR^4R^5)_m$—$R^6$ and $R^6$ is —$C(O)OCH_2OC(O)OCH(CH_3)_2$. In some embodiments is a compound of Formula (Ia), or a pharmaceutically acceptable salt or solvate thereof, wherein $R^1$ is —$(CR^4R^5)_m$—$R^6$ and $R^6$ is —$C(O)OCH_2OC(O)OC(CH_3)_3$. In some embodiments is a compound of Formula (Ia), or a pharmaceutically acceptable salt or solvate thereof, wherein $R^1$ is —$(CR^4R^5)_m$—$R^6$ and $R^6$ is —$C(O)OCH_2OC(O)CH(CH_3)_2$. In some embodiments is a compound of Formula (Ia), or a pharmaceutically acceptable salt or solvate thereof, wherein $R^1$ is —$(CR^4R^5)_m$—$R^6$ and m is 1. In some embodiments is a compound of Formula (Ia), or a pharmaceutically acceptable salt or solvate thereof, wherein $R^1$ is —$(CR^4R^5)_m$—$R^6$ and m is 2. In some embodiments is a compound of Formula (Ia), or a pharmaceutically acceptable salt or solvate thereof, wherein $R^1$ is —$(CR^4R^5)_m$—$R^6$ and m is 3. In some embodiments is a compound of Formula (Ia), or a pharmaceutically acceptable salt or solvate thereof, wherein $R^1$ is —$(CR^4R^5)_m$—$R^6$ and m is 4. In some embodiments is a compound of Formula (Ia), or a pharmaceutically acceptable salt or solvate thereof, wherein $R^1$ is —$(CR^4R^5)_m$—$R^6$ and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$ and each $R^4$ and $R^5$ is H.

In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ is independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is each independently selected from H and $C_{1-6}$alkyl.

In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ are H. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is H. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is H. In some embodiments is a compound of Formula (Ia), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is H.

In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ is independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ are H. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is H. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is H. In some embodiments is a compound of Formula (Ia), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is H.

In some embodiments is a compound of Formula (Ia), or a pharmaceutically acceptable salt or solvate thereof, wherein $R^1$ is —$(CR^4R^5)_p$—Y—$(CR^4R^5)_q$—$R^6$. In some embodiments is a compound of Formula (Ia), or a pharmaceutically acceptable salt or solvate thereof, wherein $R^1$ is —$(CR^4R^5)_p$—Y—$(CR^4R^5)_q$—$R^6$ and $R^6$ is —$CO_2R^9$. In some embodiments is a compound of Formula (Ia), or a pharmaceutically acceptable salt or solvate thereof, wherein $R^1$ is —$(CR^4R^5)_p$—Y—$(CR^4R^5)_q$—$R^6$ and $R^6$ is —$CO_2H$. In some embodiments is a compound of Formula (Ia), or a pharmaceutically acceptable salt or solvate thereof, wherein $R^1$ is —$(CR^4R^5)_p$—Y—$(CR^4R^5)_q$—$R^6$ and $R^6$ is —$CO_2CH_3$. In some embodiments is a compound of Formula (Ia), or a pharmaceutically acceptable salt or solvate thereof, wherein $R^1$ is —$(CR^4R^5)_p$—Y—$(CR^4R^5)_q$—$R^6$ and $R^6$ is —$CO_2CH_2CH_3$. In some embodiments is a compound of Formula (Ia), or a pharmaceutically acceptable salt or solvate thereof, wherein $R^1$ is —$(CR^4R^5)_p$—Y—$(CR^4R^5)_q$—$R^6$ and Y is —O—. In some embodiments is a compound of Formula (Ia), or a pharmaceutically acceptable salt or solvate thereof, wherein $R^1$ is $-(CR^4R^5)_p-Y-(CR^4R^5)_q-R^6$ and Y is $-N(R^7)-$. In some embodiments is a compound of Formula (Ia), or a pharmaceutically acceptable salt or solvate thereof, wherein $R^1$ is $-(CR^4R^5)_p-Y-(CR^4R^5)_q-R^6$ and Y is $-N(H)-$. In some embodiments is a compound of Formula (Ia), or a pharmaceutically acceptable salt or solvate thereof, wherein $R^1$ is $-(CR^4R^5)_p-Y-(CR^4R^5)_q-R^6$ and Y is $-N(SO_2Me)-$. In some embodiments is a compound of Formula (Ia), or a pharmaceutically acceptable salt or solvate thereof, wherein $R^1$ is $-(CR^4R^5)_p-Y-(CR^4R^5)_q-R^6$ and p is 2. In some embodiments is a compound of Formula (Ia), or a pharmaceutically acceptable salt or solvate thereof, wherein $R^1$ is $-(CR^4R^5)_p-Y-(CR^4R^5)_q-R^6$ and p is 3. In some embodiments is a compound of Formula (Ia), or a pharmaceutically acceptable salt or solvate thereof, wherein $R^1$ is $-(CR^4R^5)_p-Y-(CR^4R^5)_q-R^6$ and p is 4. In some embodiments is a compound of Formula (Ia), or a pharmaceutically acceptable salt or solvate thereof, wherein $R^1$ is $-(CR^4R^5)_p-Y-(CR^4R^5)_q-R^6$ and q is 1. In some embodiments is a compound of Formula (Ia), or a pharmaceutically acceptable salt or solvate thereof, wherein $R^1$ is $-(CR^4R^5)_p-Y-(CR^4R^5)_q-R^6$ and q is 2. In some embodiments is a compound of Formula (Ia), or a pharmaceutically acceptable salt or solvate thereof, wherein $R^1$ is $-(CR^4R^5)_p-Y-(CR^4R^5)_q-R^6$ and q is 3. In some embodiments is a compound of Formula (Ia), or a pharmaceutically acceptable salt or solvate thereof, wherein $R^1$ is $-(CR^4R^5)_p-Y-(CR^4R^5)_q-R^6$ and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is $-(CR^4R^5)_p-Y-(CR^4R^5)_q-R^6$ and each $R^4$ and $R^5$ is H.

In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ is independently selected from H and $C_{1-6}$alkyl. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is each independently selected from H and $C_{1-6}$alkyl.

In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ are H. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is H. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is H.

In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ is independently selected from H and $C_{1-6}$alkyl. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(H)-$, p is 2, q is 1, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(SO_2Me)-$, p is 2, q is 1, and each $R^4$ and $R^5$ is each independently selected from H and $C_{1-6}$alkyl.

In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ are H. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(H)-$, p is 2, q is 1, and each $R^4$ and $R^5$ is H. In some embodiments is a compound of Formula (Ia), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(SO_2Me)-$, p is 2, q is 1, and each $R^4$ and $R^5$ is H.

In some embodiments is a compound of Formula (Ia), or a pharmaceutically acceptable salt or solvate thereof, wherein $R^1$ is $-(CR^4R^5)_t-C_{3-6}$cycloalkyl-$R^6$. In some embodiments is a compound of Formula (Ia), or a pharmaceutically acceptable salt or solvate thereof, wherein $R^1$ is $-(CR^4R^5)_t$-cyclopropyl-$R^6$. In some embodiments is a compound of Formula (Ia), or a pharmaceutically acceptable salt or solvate thereof, wherein $R^1$ is $-(CR^4R^5)_t$-cyclobutyl-$R^6$. In some embodiments is a compound of Formula (Ia), or a pharmaceutically acceptable salt or solvate thereof, wherein $R^1$ is $-(CR^4R^5)_t$-cyclopentyl-$R^6$. In some embodiments is a compound of Formula (Ia), or a pharmaceutically acceptable salt or solvate thereof, wherein $R^1$ is $-(CR^4R^5)_t$-cyclohexyl-$R^6$. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and $R^6$ is $-CO_2R^9$. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and $R^6$ is $-CO_2H$. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and $R^6$ is $-CO_2CH_3$. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and $R^6$ is $-CO_2CH_2CH_3$. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and t is 0. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and t is 1. In some embodiments is a compound of Formula (Ia), or a pharmaceutically acceptable salt or solvate thereof, wherein $R^1$ is $-(CR^4R^5)_t-C_{3-6}$cycloalkyl-$R^6$ and t is 2.

In some embodiments is a compound of Formula (Ia), or a pharmaceutically acceptable salt or solvate thereof, wherein $R^1$ is $-(CR^4R^5)_t-C_{3-6}$cycloalkyl-$R^6$, $R^6$ is $-CO_2H$, t is 0, and $R^4$ and $R^5$ is independently selected from H and $C_{1-6}$alkyl. In some embodiments is a compound of Formula (Ia), or a pharmaceutically acceptable salt or solvate thereof, wherein $R^1$ is $-(CR^4R^5)_t-C_{3-6}$cycloalkyl-$R^6$, $R^6$ is $-CO_2H$, t is 1, and each $R^4$ and $R^5$ is each independently selected from H and $C_{1-6}$alkyl. In some embodiments is a compound of Formula (Ia), or a pharmaceutically acceptable salt or solvate thereof, wherein $R^1$ is —(CR$^4$R$^5$)$_t$—C$_{3-6}$cycloalkyl-R$^6$, R$^6$ is —CO$_2$H, t is 2, and each R$^4$ and R$^5$ is each independently selected from H and C$_{1-6}$alkyl.

In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$H, t is 0, and R$^4$ and R$^5$ are H. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$H, t is 1, and each R$^4$ and R$^5$ is H. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$H, t is 2, and each R$^4$ and R$^5$ is H.

In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 0, and R$^4$ and R$^5$ is independently selected from H and C$_{1-6}$alkyl. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 1, and each R$^4$ and R$^5$ is each independently selected from H and C$_{1-6}$alkyl. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 2, and each R$^4$ and R$^5$ is each independently selected from H and C$_{1-6}$alkyl.

In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 0, and R$^4$ and R$^5$ are H. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 1, and each R$^4$ and R$^5$ is H. In some embodiments is a compound of Formula (Ia), or a pharmaceutically acceptable salt or solvate thereof, wherein R$^1$ is —(CR$^4$R$^5$)$_t$—C$_{3-6}$cycloalkyl-R$^6$, R$^6$ is —CO$_2$R$^9$, R$^9$ is C$_{1-6}$alkyl, t is 2, and each R$^4$ and R$^5$ is H.

In some embodiments is a compound of Formula (Ia), or a pharmaceutically acceptable salt or solvate thereof, wherein —X—R$^1$ is —OCH$_2$C(O)OH. In some embodiments is a compound of Formula (Ia), or a pharmaceutically acceptable salt or solvate thereof, wherein —X—R$^1$ is —N(H)CH$_2$C(O)OH. In some embodiments is a compound of Formula (Ia), or a pharmaceutically acceptable salt or solvate thereof, wherein —X—R$^1$ is —OCH(CH$_3$)C(O)OH. In some embodiments is a compound of Formula (Ia), or a pharmaceutically acceptable salt or solvate thereof, wherein —X—R$^1$ is —N(H)CH(CH$_3$)C(O)OH. In some embodiments is a compound of Formula (Ia), or a pharmaceutically acceptable salt or solvate thereof, wherein —X—R$^1$ is —OCH$_2$CH$_2$C(O)OH. In some embodiments is a compound of Formula (Ia), or a pharmaceutically acceptable salt or solvate thereof, wherein —X—R$^1$ is —N(H)CH$_2$CH$_2$C(O)OH. In some embodiments is a compound of Formula (Ia), or a pharmaceutically acceptable salt or solvate thereof, wherein —X—R$^1$ is —OCH$_2$CH$_2$CH$_2$C(O)OH. In some embodiments is a compound of Formula (Ia), or a pharmaceutically acceptable salt or solvate thereof, wherein —X—R$^1$ is —N(H)CH$_2$CH$_2$CH$_2$C(O)OH. In some embodiments is a compound of Formula (Ia), or a pharmaceutically acceptable salt or solvate thereof, wherein —X—R$^1$ is —OCH$_2$CH$_2$C(CH$_3$)$_2$C(O)OH. In some embodiments is a compound of Formula (Ia), or a pharmaceutically acceptable salt or solvate thereof, wherein —X—R$^1$ is —N(H)CH$_2$CH$_2$C(CH$_3$)$_2$C(O)OH.

In some embodiments is a compound of Formula (Ia), or a pharmaceutically acceptable salt or solvate thereof, wherein —X—R$^1$ is —OCH$_2$C(O)OCH$_3$. In some embodiments is a compound of Formula (Ia), or a pharmaceutically acceptable salt or solvate thereof, wherein —X—R$^1$ is —N(H)CH$_2$C(O)OCH$_3$. In some embodiments is a compound of Formula (Ia), or a pharmaceutically acceptable salt or solvate thereof, wherein —X—R$^1$ is —OCH(CH$_3$)C(O)OCH$_3$. In some embodiments is a compound of Formula (Ia), or a pharmaceutically acceptable salt or solvate thereof, wherein —X—R$^1$ is —N(H)CH(CH$_3$)C(O)OCH$_3$. In some embodiments is a compound of Formula (Ia), or a pharmaceutically acceptable salt or solvate thereof, wherein —X—R$^1$ is —OCH$_2$CH$_2$C(O)OCH$_3$. In some embodiments is a compound of Formula (Ia), or a pharmaceutically acceptable salt or solvate thereof, wherein —X—R$^1$ is —N(H)CH$_2$CH$_2$C(O)OCH$_3$. In some embodiments is a compound of Formula (Ia), or a pharmaceutically acceptable salt or solvate thereof, wherein —X—R$^1$ is —OCH$_2$CH$_2$CH$_2$C(O)OCH$_3$. In some embodiments is a compound of Formula (Ia), or a pharmaceutically acceptable salt or solvate thereof, wherein —X—R$^1$ is —N(H)CH$_2$CH$_2$CH$_2$C(O)OCH$_3$. In some embodiments is a compound of Formula (Ia), or a pharmaceutically acceptable salt or solvate thereof, wherein —X—R$^1$ is —OCH$_2$CH$_2$C(CH$_3$)$_2$C(O)OCH$_3$. In some embodiments is a compound of Formula (Ia), or a pharmaceutically acceptable salt or solvate thereof, wherein —X—R$^1$ is —N(H)CH$_2$CH$_2$C(CH$_3$)$_2$C(O)OCH$_3$.

In some embodiments is a compound of Formula (Ia), or a pharmaceutically acceptable salt or solvate thereof, wherein —X—R$^1$ is —OCH$_2$CH$_2$OCH$_2$C(O)OH. In some embodiments is a compound of Formula (Ia), or a pharmaceutically acceptable salt or solvate thereof, wherein —X—R$^1$ is —N(H)CH$_2$CH$_2$OCH$_2$C(O)OH. In some embodiments is a compound of Formula (Ia), or a pharmaceutically acceptable salt or solvate thereof, wherein —X—R$^1$ is —OCH$_2$CH$_2$N(H)CH$_2$C(O)OH. In some embodiments is a compound of Formula (Ia), or a pharmaceutically acceptable salt or solvate thereof, wherein —X—R$^1$ is —N(H)CH$_2$CH$_2$N(SO$_2$CH$_3$)CH$_2$C(O)OH. In some embodiments is a compound of Formula (Ia), or a pharmaceutically acceptable salt or solvate thereof, wherein —X—R$^1$ is —OCH$_2$CH$_2$CH$_2$C(O)OCH(CH$_3$)OC(O)OCH$_2$CH$_3$. In some embodiments is a compound of Formula (Ia), or a pharmaceutically acceptable salt or solvate thereof, wherein —X—R$^1$ is —N(H)CH$_2$CH$_2$CH$_2$C(O)OCH(CH$_3$)OC(O)OCH(CH$_3$)$_2$. In some embodiments is a compound of Formula (Ia), or a pharmaceutically acceptable salt or solvate thereof, wherein —X—R$^1$ is —OCH$_2$CH$_2$CH$_2$C(O)OCH$_2$OC(O)OC(CH$_3$)$_3$. In some embodiments is a compound of Formula (Ia), or a pharmaceutically acceptable salt or solvate thereof, wherein —X—R$^1$ is —N(H)CH$_2$CH$_2$CH$_2$C(O)OCH(CH$_3$)OC(O)CH(CH$_3$)$_2$.

In some embodiments is a compound of Formula (Ia), or a pharmaceutically acceptable salt or solvate thereof, wherein —X—R$^1$ is —O-cyclopropyl-C(O)OH. In some embodiments is a compound of Formula (Ia), or a pharmaceutically acceptable salt or solvate thereof, wherein —X—R$^1$ is —N(H)-cyclopropyl-C(O)OH. In some embodiments is a compound of Formula (Ia), or a pharmaceutically acceptable salt or solvate thereof, wherein —X—R$^1$ is —O-cyclobutyl-C(O)OH. In some embodiments is a compound of Formula (Ia), or a pharmaceutically acceptable salt or solvate thereof, wherein —X—R¹ is —N(H)-cyclobutyl-C(O)OH.

In some embodiments is a compound of Formula (Ia), or a pharmaceutically acceptable salt or solvate thereof, wherein n is 0, 1, 2, or 3. In some embodiments is a compound of Formula (Ia), or a pharmaceutically acceptable salt or solvate thereof, wherein n is 0, 1, or 2. In some embodiments is a compound of Formula (Ia), or a pharmaceutically acceptable salt or solvate thereof, wherein n is 1 or 2. In some embodiments is a compound of Formula (Ia), or a pharmaceutically acceptable salt or solvate thereof, wherein n is 0 or 1. In some embodiments is a compound of Formula (Ia), or a pharmaceutically acceptable salt or solvate thereof, wherein n is 0. In some embodiments is a compound of Formula (Ia), or a pharmaceutically acceptable salt or solvate thereof, wherein n is 1. In some embodiments is a compound of Formula (Ia), or a pharmaceutically acceptable salt or solvate thereof, wherein n is 2. In some embodiments is a compound of Formula (Ia), or a pharmaceutically acceptable salt or solvate thereof, wherein n is 3. In some embodiments is a compound of Formula (Ia), or a pharmaceutically acceptable salt or solvate thereof, wherein n is 4.

In some embodiments is a compound of Formula (Ia), or a pharmaceutically acceptable salt or solvate thereof, wherein n is 1 and $R^2$ is halogen, $C_{1-6}$alkyl, $C_{1-6}$haloalkyl, or —$OR^{17}$. In some embodiments is a compound of Formula (Ia), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (Ia), or a pharmaceutically acceptable salt or solvate thereof, wherein n is 1 and $R^2$ is halogen. In some embodiments is a compound of Formula (Ia), or a pharmaceutically acceptable salt or solvate thereof, wherein n is 1 and $R^2$ is —Cl. In some embodiments is a compound of Formula (Ia), or a pharmaceutically acceptable salt or solvate thereof, wherein n is 1 and $R^2$ is —F. In some embodiments is a compound of Formula (Ia), or a pharmaceutically acceptable salt or solvate thereof, wherein n is 1 and $R^2$ is $C_{1-6}$alkyl. In some embodiments is a compound of Formula (Ia), or a pharmaceutically acceptable salt or solvate thereof, wherein n is 1 and $R^2$ is —$CH_3$. In some embodiments is a compound of Formula (Ia), or a pharmaceutically acceptable salt or solvate thereof, wherein n is 1 and $R^2$ is $C_{1-6}$haloalkyl. In some embodiments is a compound of Formula (Ia), or a pharmaceutically acceptable salt or solvate thereof, wherein n is 1 and $R^2$ is —$CF_3$. In some embodiments is a compound of Formula (Ia), or a pharmaceutically acceptable salt or solvate thereof, wherein n is 1 and $R^2$ is $C_{1-6}$alkoxy. In some embodiments is a compound of Formula (Ia), or a pharmaceutically acceptable salt or solvate thereof, wherein n is 1 and $R^2$ is —$OCH_3$. In some embodiments is a compound of Formula (Ia), or a pharmaceutically acceptable salt or solvate thereof, wherein n is 1 and $R^2$ is $C_{1-6}$haloalkoxy. In some embodiments is a compound of Formula (Ia), or a pharmaceutically acceptable salt or solvate thereof, wherein n is 1 and $R^2$ is —$OCF_3$. In some embodiments is a compound of Formula (Ia), or a pharmaceutically acceptable salt or solvate thereof, wherein n is 1 and $R^2$ is —OH. In some embodiments is a compound of Formula (Ia), or a pharmaceutically acceptable salt or solvate thereof, wherein n is 1 and $R^2$ is —CN.

In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, or —$OR^{17}$. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, —$OCF_3$, or —CN. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, or —$OCF_3$. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, or —$OCF_3$. In some embodiments is a compound of Formula (Ia), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (Ia), or a pharmaceutically acceptable salt or solvate thereof, wherein n is 2 and each $R^2$ is independently halogen or $C_{1-6}$haloalkyl. In some embodiments is a compound of Formula (Ia), or a pharmaceutically acceptable salt or solvate thereof, wherein n is 2 and each $R^2$ is independently halogen or $C_{1-6}$alkyl. In some embodiments is a compound of Formula (Ia), or a pharmaceutically acceptable salt or solvate thereof, wherein n is 2 and each $R^2$ is independently halogen. In some embodiments is a compound of Formula (Ia), or a pharmaceutically acceptable salt or solvate thereof, wherein n is 2 and each $R^2$ is independently $C_{1-6}$alkyl. In some embodiments is a compound of Formula (Ia), or a pharmaceutically acceptable salt or solvate thereof, wherein n is 2 and each $R^2$ is independently $C_{1-6}$haloalkyl.

In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, or —$OR^{17}$. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —$OCF_3$, or —CN. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —$OCF_3$. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, or —$OCF_3$. In some embodiments is a compound of Formula (Ia), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (Ia), or a pharmaceutically acceptable salt or solvate thereof, wherein n is 3 and each $R^2$ is independently halogen or $C_{1-6}$haloalkyl. In some embodiments is a compound of Formula (Ia), or a pharmaceutically acceptable salt or solvate thereof, wherein n is 3 and each $R^2$ is independently halogen or $C_{1-6}$alkyl. In some embodiments is a compound of Formula (Ia), or a pharmaceutically acceptable salt or solvate thereof, wherein n is 3 and each $R^2$ is independently halogen. In some embodiments is a compound of Formula (Ia), or a pharmaceutically acceptable salt or solvate thereof, wherein n is 3 and each $R^2$ is independently $C_{1-6}$alkyl. In some embodiments is a compound of Formula (Ia), or a pharmaceutically acceptable salt or solvate thereof, wherein n is 3 and each $R^2$ is independently $C_{1-6}$haloalkyl.

In some embodiments is a compound of Formula (Ia), or a pharmaceutically acceptable salt or solvate thereof, wherein n is 4 and each $R^2$ is independently halogen, $C_{1-6}$alkyl, $C_{1-6}$haloalkyl, and $-OR^{17}$.

In some embodiments is a compound of Formula (Iaa):

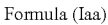

Formula (Iaa)

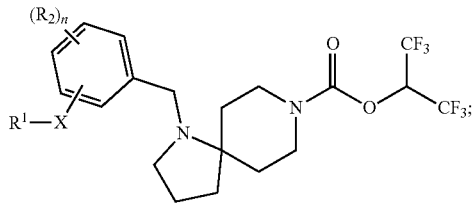

wherein:
X is $-O-$ or $-N(R^3)-$;
$R^1$ is $-(CR^4R^5)_m-R^6$;
each $R^2$ is independently selected from halogen, $C_{1-6}$alkyl, or $C_{1-6}$haloalkyl;
$R^3$ is H or $C_{1-6}$alkyl;
each $R^4$ and $R^5$ is each independently selected from H, F, and $C_{1-6}$alkyl;
$R^6$ is $-CO_2R^9$;
$R^9$ is H or $C_{1-6}$alkyl;
m is 1, 2, 3 or 4; and
n is 0, 1, or 2;
or a pharmaceutically acceptable salt or solvate thereof.

In some embodiments is a compound of Formula (Iaa), or a pharmaceutically acceptable salt or solvate thereof, wherein X is $-O-$. In some embodiments is a compound of Formula (Iaa), or a pharmaceutically acceptable salt or solvate thereof, wherein X is $-N(R^3)-$. In some embodiments is a compound of Formula (Iaa), or a pharmaceutically acceptable salt or solvate thereof, wherein X is $-N(H)-$. In some embodiments is a compound of Formula (Iaa), or a pharmaceutically acceptable salt or solvate thereof, wherein X is $-N(CH_3)-$. In some embodiments is a compound of Formula (Iaa), or a pharmaceutically acceptable salt or solvate thereof, wherein X is $-N(CH_2CH_3)-$.

In some embodiments is a compound of Formula (Iaa), or a pharmaceutically acceptable salt or solvate thereof, wherein $R^1$ is $-(CR^4R^5)_m-R^6$. In some embodiments is a compound of Formula (Iaa), or a pharmaceutically acceptable salt or solvate thereof, wherein $R^1$ is $-(CR^4R^5)_m-R^6$ and $R^6$ is $-CO_2R^9$. In some embodiments is a compound of Formula (Iaa), or a pharmaceutically acceptable salt or solvate thereof, wherein $R^1$ is $-(CR^4R^5)_m-R^6$ and $R^6$ is $-CO_2H$. In some embodiments is a compound of Formula (Iaa), or a pharmaceutically acceptable salt or solvate thereof, wherein $R^1$ is $-(CR^4R^5)_m-R^6$ and $R^6$ is $-CO_2CH_3$. In some embodiments is a compound of Formula (Iaa), or a pharmaceutically acceptable salt or solvate thereof, wherein $R^1$ is $-(CR^4R^5)_m-R^6$ and $R^6$ is $-CO_2CH_2CH_3$. In some embodiments is a compound of Formula (Iaa), or a pharmaceutically acceptable salt or solvate thereof, wherein $R^1$ is $-(CR^4R^5)_m-R^6$ and m is 1. In some embodiments is a compound of Formula (Iaa), or a pharmaceutically acceptable salt or solvate thereof, wherein $R^1$ is $-(CR^4R^5)_m-R^6$ and m is 2. In some embodiments is a compound of Formula (Iaa), or a pharmaceutically acceptable salt or solvate thereof, wherein $R^1$ is $-(CR^4R^5)_m-R^6$ and m is 3. In some embodiments is a compound of Formula (Iaa), or a pharmaceutically acceptable salt or solvate thereof, wherein $R^1$ is $-(CR^4R^5)_m-R^6$ and m is 4. In some embodiments is a compound of Formula (Iaa), or a pharmaceutically acceptable salt or solvate thereof, wherein $R^1$ is $-(CR^4R^5)_m-R^6$ and each $R^4$ and $R^5$ is each independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$ and each $R^4$ and $R^5$ is H.

In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 1, and $R^4$ and $R^5$ is independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 2, and each $R^4$ and $R^5$ is each independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 3, and each $R^4$ and $R^5$ is each independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 4, and each $R^4$ and $R^5$ is each independently selected from H and $C_{1-6}$alkyl.

In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 1, and $R^4$ and $R^5$ are H. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 2, and each $R^4$ and $R^5$ is H. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 3, and each $R^4$ and $R^5$ is H. In some embodiments is a compound of Formula (Iaa), or a pharmaceutically acceptable salt or solvate thereof, wherein $R^1$ is $-(CR^4R^5)_m-R^6$, $R^6$ is $-CO_2H$, m is 4, and each $R^4$ and $R^5$ is H.

In some embodiments is a compound of Formula (Iaa), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ is independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 2, and each $R^4$ and $R^5$ is each independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is each independently selected from H and $C_{1-6}$alkyl. In some embodiments is a compound of Formula (Iaa), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Iaa), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ are H. In some embodiments is a compound of Formula (Iaa), or a pharmaceutically acceptable salt or solvate thereof, wherein $R^1$ is $-(CR^4R^5)$ $_m$—R$^6$, R$^6$ is —CO$_2$R$^9$, R$^9$ is C$_{1-6}$alkyl, m is 2, and each R$^4$ and R$^5$ is H. In some embodiments is a compound of Formula (Iaa), or a pharmaceutically acceptable salt or solvate thereof, wherein R$^1$ is —(CR$^4$R$^5$)$_m$—R$^6$, R$^6$ is —CO$_2$R$^9$, R$^9$ is C$_{1-6}$alkyl, m is 3, and each R$^4$ and R$^5$ is H. In some embodiments is a compound of Formula (Iaa), or a pharmaceutically acceptable salt or solvate thereof, wherein R$^1$ is —(CR$^4$R$^5$)$_m$—R$^6$, R$^6$ is —CO$_2$R$^9$, R$^9$ is C$_{1-6}$alkyl, m is 4, and each R$^4$ and R$^5$ is H.

In some embodiments is a compound of Formula (Iaa), or a pharmaceutically acceptable salt or solvate thereof, wherein —X—R$^1$ is —OCH$_2$C(O)OH. In some embodiments is a compound of Formula (Iaa), or a pharmaceutically acceptable salt or solvate thereof, wherein —X—R$^1$ is —N(H)CH$_2$C(O)OH. In some embodiments is a compound of Formula (Iaa), or a pharmaceutically acceptable salt or solvate thereof, wherein —X—R$^1$ is —OCH(CH$_3$)C(O)OH. In some embodiments is a compound of Formula (Iaa), or a pharmaceutically acceptable salt or solvate thereof, wherein —X—R$^1$ is —N(H)CH(CH$_3$)C(O)OH. In some embodiments is a compound of Formula (Iaa), or a pharmaceutically acceptable salt or solvate thereof, wherein —X—R$^1$ is —OCH$_2$CH$_2$C(O)OH. In some embodiments is a compound of Formula (Iaa), or a pharmaceutically acceptable salt or solvate thereof, wherein —X—R$^1$ is —N(H)CH$_2$CH$_2$C(O)OH. In some embodiments is a compound of Formula (Iaa), or a pharmaceutically acceptable salt or solvate thereof, wherein —X—R$^1$ is —OCH$_2$CH$_2$CH$_2$C(O)OH. In some embodiments is a compound of Formula (Iaa), or a pharmaceutically acceptable salt or solvate thereof, wherein —X—R$^1$ is —N(H)CH$_2$CH$_2$CH$_2$C(O)OH. In some embodiments is a compound of Formula (Iaa), or a pharmaceutically acceptable salt or solvate thereof, wherein —X—R$^1$ is —OCH$_2$CH$_2$C(CH$_3$)$_2$C(O)OH. In some embodiments is a compound of Formula (Iaa), or a pharmaceutically acceptable salt or solvate thereof, wherein —X—R$^1$ is —N(H)CH$_2$CH$_2$C(CH$_3$)$_2$C(O)OH.

In some embodiments is a compound of Formula (Iaa), or a pharmaceutically acceptable salt or solvate thereof, wherein —X—R$^1$ is —OCH$_2$C(O)OCH$_3$. In some embodiments is a compound of Formula (Iaa), or a pharmaceutically acceptable salt or solvate thereof, wherein —X—R$^1$ is —N(H)CH$_2$C(O)OCH$_3$. In some embodiments is a compound of Formula (Iaa), or a pharmaceutically acceptable salt or solvate thereof, wherein —X—R$^1$ is —OCH(CH$_3$)C(O)OCH$_3$. In some embodiments is a compound of Formula (Iaa), or a pharmaceutically acceptable salt or solvate thereof, wherein —X—R$^1$ is —N(H)CH(CH$_3$)C(O)OCH$_3$. In some embodiments is a compound of Formula (Iaa), or a pharmaceutically acceptable salt or solvate thereof, wherein —X—R$^1$ is —OCH$_2$CH$_2$C(O)OCH$_3$. In some embodiments is a compound of Formula (Iaa), or a pharmaceutically acceptable salt or solvate thereof, wherein —X—R$^1$ is —N(H)CH$_2$CH$_2$C(O)OCH$_3$. In some embodiments is a compound of Formula (Iaa), or a pharmaceutically acceptable salt or solvate thereof, wherein —X—R$^1$ is —OCH$_2$CH$_2$CH$_2$C(O)OCH$_3$. In some embodiments is a compound of Formula (Iaa), or a pharmaceutically acceptable salt or solvate thereof, wherein —X—R$^1$ is —N(H)CH$_2$CH$_2$CH$_2$C(O)OCH$_3$. In some embodiments is a compound of Formula (Iaa), or a pharmaceutically acceptable salt or solvate thereof, wherein —X—R$^1$ is —OCH$_2$CH$_2$C(CH$_3$)$_2$C(O)OCH$_3$. In some embodiments is a compound of Formula (Iaa), or a pharmaceutically acceptable salt or solvate thereof, wherein —X—R$^1$ is —N(H)CH$_2$CH$_2$C(CH$_3$)$_2$C(O)OCH$_3$.

In some embodiments is a compound of Formula (Iaa), or a pharmaceutically acceptable salt or solvate thereof, wherein n is 1 or 2. In some embodiments is a compound of Formula (Iaa), or a pharmaceutically acceptable salt or solvate thereof, wherein n is 0 or 1. In some embodiments is a compound of Formula (Iaa), or a pharmaceutically acceptable salt or solvate thereof, wherein n is 0. In some embodiments is a compound of Formula (Iaa), or a pharmaceutically acceptable salt or solvate thereof, wherein n is 1. In some embodiments is a compound of Formula (Iaa), or a pharmaceutically acceptable salt or solvate thereof, wherein n is 2.

In some embodiments is a compound of Formula (Iaa), or a pharmaceutically acceptable salt or solvate thereof, wherein n is 1 and R$^2$ is halogen, C$_{1-6}$alkyl, or C$_{1-6}$haloalkyl. In some embodiments is a compound of Formula (Iaa), or a pharmaceutically acceptable salt or solvate thereof, wherein n is 1 and R$^2$ is halogen. In some embodiments is a compound of Formula (Iaa), or a pharmaceutically acceptable salt or solvate thereof, wherein n is 1 and R$^2$ is —Cl. In some embodiments is a compound of Formula (Iaa), or a pharmaceutically acceptable salt or solvate thereof, wherein n is 1 and R$^2$ is —F. In some embodiments is a compound of Formula (Iaa), or a pharmaceutically acceptable salt or solvate thereof, wherein n is 1 and R$^2$ is C$_{1-6}$alkyl. In some embodiments is a compound of Formula (Iaa), or a pharmaceutically acceptable salt or solvate thereof, wherein n is 1 and R$^2$ is —CH$_3$. In some embodiments is a compound of Formula (Iaa), or a pharmaceutically acceptable salt or solvate thereof, wherein n is 1 and R$^2$ is C$_{1-6}$haloalkyl. In some embodiments is a compound of Formula (Iaa), or a pharmaceutically acceptable salt or solvate thereof, wherein n is 1 and R$^2$ is —CF$_3$.

In some embodiments is a compound of Formula (Iaa), or a pharmaceutically acceptable salt or solvate thereof, wherein n is 2 and each R$^2$ is independently halogen, C$_{1-6}$alkyl, or C$_{1-6}$haloalkyl. In some embodiments is a compound of Formula (Iaa), or a pharmaceutically acceptable salt or solvate thereof, wherein n is 2 and each R$^2$ is independently halogen or C$_{1-6}$haloalkyl. In some embodiments is a compound of Formula (Iaa), or a pharmaceutically acceptable salt or solvate thereof, wherein n is 2 and each R$^2$ is independently halogen or C$_{1-6}$alkyl. In some embodiments is a compound of Formula (Iaa), or a pharmaceutically acceptable salt or solvate thereof, wherein n is 2 and each R$^2$ is independently halogen. In some embodiments is a compound of Formula (Iaa), or a pharmaceutically acceptable salt or solvate thereof, wherein n is 2 and each R$^2$ is independently C$_{1-6}$alkyl. In some embodiments is a compound of Formula (Iaa), or a pharmaceutically acceptable salt or solvate thereof, wherein n is 2 and each R$^2$ is independently C$_{1-6}$haloalkyl.

In some embodiments is a compound of Formula (Ib):

Formula (Ib)

wherein:
X is —O—, —S—, —SO$_2$—, —N(R$^3$)—, or —CH$_2$—;
Y is —O— or —N(R$^7$)—;
R$^1$ is —(CR$^4$R$^5$)$_m$—R$^6$, —(CR$^4$R$^5$)$_p$—Y—(CR$^4$R$^5$)$_q$—R$^6$, or —(CR$^4$R$^5$)$_t$—C$_{3-6}$cycloalkyl-R$^6$; each R$^2$ is independently selected from halogen, —CN, C$_{1-6}$alkyl, C$_{1-6}$haloalkyl, —C$_{1-6}$alkyl(heterocycloalkyl), —OR$^{17}$, and —C(O)NR$^{18}$R$^{19}$;
R$^3$ is H or C$_{1-6}$alkyl;
each R$^4$ and R$^5$ is each independently selected from H, F, and C$_{1-6}$alkyl; or R$^4$ and R$^5$, together with the carbon to which they are attached, form a C$_{3-6}$cycloalkyl ring;
R$^6$ is —CO$_2$R$^9$, —C(O)R$^{10}$, or —C(O)O—(CR$^{12}$R$^{13}$)—OC(O)R$^{11}$;
R$^7$ is H, C$_{1-6}$alkyl, or —SO$_2$R$^8$;
R$^8$ is C$_{1-6}$alkyl;
R$^9$ is H or C$_{1-6}$alkyl;
R$^{10}$ is C$_{1-6}$alkyl or —NHSO$_2$R$^{21}$;
R$^{11}$ is C$_{1-6}$alkyl or C$_{1-6}$alkoxy;
R$^{12}$ and R$^{13}$ is each independently H or C$_{1-6}$alkyl;
each R$^{17}$ is independently selected from H, C$_{1-6}$alkyl, C$_{1-6}$haloalkyl, aminoalkyl, cycloalkyl, —C$_{1-6}$alkyl(heterocycloalkyl), —C$_{1-6}$alkyl-C(O)(heterocycloalkyl), optionally substituted heterocycloalkyl, optionally substituted aryl, and optionally substituted heteroaryl;
each R$^{18}$ and R$^{19}$ is independently selected from H, C$_{1-6}$alkyl, C$_{1-6}$haloalkyl, cycloalkyl, aryl, and heteroaryl; or R$^{18}$ and R$^{19}$, together with the nitrogen to which they are attached, form a heterocycloalkyl ring optionally substituted with one, two, or three R$^{20}$; each R$^{20}$ is independently selected from halogen, C$_{1-6}$alkyl, C$_{1-6}$haloalkyl, oxo, —CN, and C$_{3-6}$cycloalkyl;
R$^{21}$ is C$_{1-6}$alkyl;
m is 1, 2, 3 or 4;
n is 0, 1, 2, 3, or 4;
p is 2, 3, or 4;
q is 1, 2, or 3; and
t is 0, 1, or 2;
or a pharmaceutically acceptable salt or solvate thereof.

In some embodiments is a compound of Formula (Ib), or a pharmaceutically acceptable salt or solvate thereof, wherein X is —O—, —S—, —SO$_2$—, —N(R$^3$)—, or —CH$_2$—. In some embodiments is a compound of Formula (Ib), or a pharmaceutically acceptable salt or solvate thereof, wherein X is —O—. In some embodiments is a compound of Formula (Ib), or a pharmaceutically acceptable salt or solvate thereof, wherein X is —S—. In some embodiments is a compound of Formula (Ib), or a pharmaceutically acceptable salt or solvate thereof, wherein X is —SO$_2$—. In some embodiments is a compound of Formula (Ib), or a pharmaceutically acceptable salt or solvate thereof, wherein X is —N(R$^3$)—. In some embodiments is a compound of Formula (Ib), or a pharmaceutically acceptable salt or solvate thereof, wherein X is —N(H)—. In some embodiments is a compound of Formula (Ib), or a pharmaceutically acceptable salt or solvate thereof, wherein X is —N(CH$_3$)—. In some embodiments is a compound of Formula (Ib), or a pharmaceutically acceptable salt or solvate thereof, wherein X is —N(CH$_2$CH$_3$)—. In some embodiments is a compound of Formula (Ib), or a pharmaceutically acceptable salt or solvate thereof, wherein X is —CH$_2$—.

In some embodiments is a compound of Formula (Ib), or a pharmaceutically acceptable salt or solvate thereof, wherein R$^1$ is —(CR$^4$R$^5$)$_m$—R$^6$. In some embodiments is a compound of Formula (Ib), or a pharmaceutically acceptable salt or solvate thereof, wherein R$^1$ is —(CR$^4$R$^5$)$_m$—R$^6$ and R$^6$ is —CO$_2$R$^9$. In some embodiments is a compound of Formula (Ib), or a pharmaceutically acceptable salt or solvate thereof, wherein R$^1$ is —(CR$^4$R$^5$)$_m$—R$^6$ and R$^6$ is —CO$_2$H. In some embodiments is a compound of Formula (Ib), or a pharmaceutically acceptable salt or solvate thereof, wherein R$^1$ is —(CR$^4$R$^5$)$_m$—R$^6$ and R$^6$ is —CO$_2$CH$_3$. In some embodiments is a compound of Formula (Ib), or a pharmaceutically acceptable salt or solvate thereof, wherein R$^1$ is —(CR$^4$R$^5$)$_m$—R$^6$ and R$^6$ is —CO$_2$CH$_2$CH$_3$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)R$^{10}$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)NHSO$_2$CH$_3$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)O—(CR$^{12}$R$^{13}$)—OC(O)R$^1$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)OCH$_2$OC(O)R$^{11}$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)OCH$_2$OC(O)OCH$_2$CH$_3$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)OCH$_2$OC(O)OCH(CH$_3$)$_2$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)OCH$_2$OC(O)OC(CH$_3$)$_3$. In some embodiments is a compound of Formula (Ib), or a pharmaceutically acceptable salt or solvate thereof, wherein R$^1$ is —(CR$^4$R$^5$)$_m$—R$^6$ and R$^6$ is —C(O)OCH$_2$OC(O)CH(CH$_3$)$_2$. In some embodiments is a compound of Formula (Ib), or a pharmaceutically acceptable salt or solvate thereof, wherein R$^1$ is —(CR$^4$R$^5$)$_m$—R$^6$ and m is 1. In some embodiments is a compound of Formula (Ib), or a pharmaceutically acceptable salt or solvate thereof, wherein R$^1$ is —(CR$^4$R$^5$)$_m$—R$^6$ and m is 2. In some embodiments is a compound of Formula (Ib), or a pharmaceutically acceptable salt or solvate thereof, wherein R$^1$ is —(CR$^4$R$^5$)$_m$—R$^6$ and m is 3. In some embodiments is a compound of Formula (Ib), or a pharmaceutically acceptable salt or solvate thereof, wherein R$^1$ is —(CR$^4$R$^5$)$_m$—R$^6$ and m is 4. In some embodiments is a compound of Formula (Ib), or a pharmaceutically acceptable salt or solvate thereof, wherein R$^1$ is —(CR$^4$R$^5$)$_m$—R$^6$ and each R$^4$ and R$^5$ is each independently selected from H and C$_{1-6}$alkyl. In some embodiments is a compound of Formula (Ib), or a pharmaceutically acceptable salt or solvate thereof, wherein R$^1$ is —(CR$^4$R$^5$)$_m$—R$^6$ and each R$^4$ and R$^5$ is H.

In some embodiments is a compound of Formula (Ib), or a pharmaceutically acceptable salt or solvate thereof, wherein R$^1$ is —(CR$^4$R$^5$)$_m$—R$^6$, R$^6$ is —CO$_2$H, m is 1, and R$^4$ and R$^5$ is independently selected from H and C$_{1-6}$alkyl. In some embodiments is a compound of Formula (Ib), or a pharmaceutically acceptable salt or solvate thereof, wherein R$^1$ is —(CR$^4$R$^5$)$_m$—R$^6$, R$^6$ is —CO$_2$H, m is 2, and each R$^4$ and R$^5$ is each independently selected from H and C$_{1-6}$alkyl. In some embodiments is a compound of Formula (Ib), or a pharmaceutically acceptable salt or solvate thereof, wherein R$^1$ is —(CR$^4$R$^5$)$_m$—R$^6$, R$^6$ is —CO$_2$H, m is 3, and each R$^4$ and R$^5$ is each independently selected from H and C$_{1-6}$alkyl. In some embodiments is a compound of Formula (Ib), or a pharmaceutically acceptable salt or solvate thereof, wherein R$^1$ is —(CR$^4$R$^5$)$_m$—R$^6$, R$^6$ is —CO$_2$H, m is 4, and each R$^4$ and R$^5$ is each independently selected from H and C$_{1-6}$alkyl.

In some embodiments is a compound of Formula (Ib), or a pharmaceutically acceptable salt or solvate thereof, wherein $R^1$ is $-(CR^4R^5)_m-R^6$, $R^6$ is $-CO_2H$, m is 1, and $R^4$ and $R^5$ are H. In some embodiments is a compound of Formula (Ib), or a pharmaceutically acceptable salt or solvate thereof, wherein $R^1$ is $-(CR^4R^5)_m-R^6$, $R^6$ is $-CO_2H$, m is 2, and each $R^4$ and $R^5$ is H. In some embodiments is a compound of Formula (Ib), or a pharmaceutically acceptable salt or solvate thereof, wherein $R^1$ is $-(CR^4R^5)_m-R^6$, $R^6$ is $-CO_2H$, m is 3, and each $R^4$ and $R^5$ is H. In some embodiments is a compound of Formula (Ib), or a pharmaceutically acceptable salt or solvate thereof, wherein $R^1$ is $-(CR^4R^5)_m-R^6$, $R^6$ is $-CO_2H$, m is 4, and each $R^4$ and $R^5$ is H.

In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ is independently selected from H and $C_{1-6}$alkyl. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 2, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 1, and $R^4$ and $R^5$ are H. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 2, and each $R^4$ and $R^5$ is H. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is H. In some embodiments is a compound of Formula (Ib), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is H.

In some embodiments is a compound of Formula (Ib), or a pharmaceutically acceptable salt or solvate thereof, wherein $R^1$ is $-(CR^4R^5)_p-Y-(CR^4R^5)_q-R^6$. In some embodiments is a compound of Formula (Ib), or a pharmaceutically acceptable salt or solvate thereof, wherein $R^1$ is $-(CR^4R^5)_p-Y-(CR^4R^5)_q-R^6$ and $R^6$ is $-CO_2R^9$. In some embodiments is a compound of Formula (Ib), or a pharmaceutically acceptable salt or solvate thereof, wherein $R^1$ is $-(CR^4R^5)_p-Y-(CR^4R^5)_q-R^6$ and $R^6$ is $-CO_2H$. In some embodiments is a compound of Formula (Ib), or a pharmaceutically acceptable salt or solvate thereof, wherein $R^1$ is $-(CR^4R^5)_p-Y-(CR^4R^5)_q-R^6$ and $R^6$ is $-CO_2CH_3$. In some embodiments is a compound of Formula (Ib), or a pharmaceutically acceptable salt or solvate thereof, wherein $R^1$ is $-(CR^4R^5)_p-Y-(CR^4R^5)_q-R^6$ and $R^6$ is $-CO_2CH_2CH_3$. In some embodiments is a compound of Formula (Ib), or a pharmaceutically acceptable salt or solvate thereof, wherein $R^1$ is $-(CR^4R^5)_p-Y-(CR^4R^5)_q-R^6$ and Y is $-O-$. In some embodiments is a compound of Formula (Ib), or a pharmaceutically acceptable salt or solvate thereof, wherein $R^1$ is $-(CR^4R^5)_p-Y-(CR^4R^5)_q-R^6$ and Y is $-N(R^7)-$. In some embodiments is a compound of Formula (Ib), or a pharmaceutically acceptable salt or solvate thereof, wherein $R^1$ is $-(CR^4R^5)_p-Y-(CR^4R^5)_q-R^6$ and Y is $-N(H)-$. In some embodiments is a compound of Formula (Ib), or a pharmaceutically acceptable salt or solvate thereof, wherein $R^1$ is $-(CR^4R^5)_p-Y-(CR^4R^5)_q-R^6$ and Y is $-N(SO_2Me)-$. In some embodiments is a compound of Formula (Ib), or a pharmaceutically acceptable salt or solvate thereof, wherein $R^1$ is $-(CR^4R^5)_p-Y-(CR^4R^5)_q-R^6$ and p is 2. In some embodiments is a compound of Formula (Ib), or a pharmaceutically acceptable salt or solvate thereof, wherein $R^1$ is $-(CR^4R^5)_p-Y-(CR^4R^5)_q-R^6$ and p is 3. In some embodiments is a compound of Formula (Ib), or a pharmaceutically acceptable salt or solvate thereof, wherein $R^1$ is $-(CR^4R^5)_p-Y-(CR^4R^5)_q-R^6$ and p is 4. In some embodiments is a compound of Formula (Ib), or a pharmaceutically acceptable salt or solvate thereof, wherein $R^1$ is $-(CR^4R^5)_p-Y-(CR^4R^5)_q-R^6$ and q is 1. In some embodiments is a compound of Formula (Ib), or a pharmaceutically acceptable salt or solvate thereof, wherein $R^1$ is $-(CR^4R^5)_p-Y-(CR^4R^5)_q-R^6$ and q is 2. In some embodiments is a compound of Formula (Ib), or a pharmaceutically acceptable salt or solvate thereof, wherein $R^1$ is $-(CR^4R^5)_p-Y-(CR^4R^5)_q-R^6$ and q is 3. In some embodiments is a compound of Formula (Ib), or a pharmaceutically acceptable salt or solvate thereof, wherein $R^1$ is $-(CR^4R^5)_p-Y-(CR^4R^5)_q-R^6$ and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_p-Y-(CR^4R^5)_q-R^6$ and each $R^4$ and $R^5$ is H.

In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ is independently selected from H and $C_{1-6}$alkyl. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is each independently selected from H and $C_{1-6}$alkyl.

In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-O-$, p is 2, q is 1, and $R^4$ and $R^5$ are H. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(H)-$, p is 2, q is 1, and each $R^4$ and $R^5$ is H. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2H$, Y is $-N(SO_2Me)-$, p is 2, q is 1, and each $R^4$ and $R^5$ is H.

In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ is independently selected from H and $C_{1-6}$alkyl. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(H)-$, p is 2, q is 1, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(SO_2Me)-$, p is 2, q is 1, and each $R^4$ and $R^5$ is each independently selected from H and $C_{1-6}$alkyl.

In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-O-$, p is 2, q is 1, and $R^4$ and $R^5$ are H. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(H)-$, p is 2, q is 1, and each $R^4$ and $R^5$ is H. In some embodiments is a compound of Formula (Ib), or a pharmaceutically acceptable salt or solvate thereof, wherein $R^1$ is $-(CR^4R^5)_p-Y-(CR^4R^5)_q-R^6$, $R^6$ is $-CO_2R^9$, $R^9$ is $C_{1-6}$alkyl, Y is $-N(SO_2Me)-$, p is 2, q is 1, and each $R^4$ and $R^5$ is H.

In some embodiments is a compound of Formula (Ib), or a pharmaceutically acceptable salt or solvate thereof, wherein $R^1$ is $-(CR^4R^5)_t-C_{3-6}$cycloalkyl-$R^6$. In some embodiments is a compound of Formula (Ib), or a pharmaceutically acceptable salt or solvate thereof, wherein $R^1$ is $-(CR^4R^5)_t$-cyclopropyl-$R^6$. In some embodiments is a compound of Formula (Ib), or a pharmaceutically acceptable salt or solvate thereof, wherein $R^1$ is $-(CR^4R^5)_t$-cyclobutyl-$R^6$. In some embodiments is a compound of Formula (Ib), or a pharmaceutically acceptable salt or solvate thereof, wherein $R^1$ is $-(CR^4R^5)_t$-cyclopentyl-$R^6$. In some embodiments is a compound of Formula (Ib), or a pharmaceutically acceptable salt or solvate thereof, wherein $R^1$ is $-(CR^4R^5)_t$-cyclohexyl-$R^6$. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and $R^6$ is $-CO_2R^9$. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and $R^6$ is $-CO_2H$. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and $R^6$ is $-CO_2CH_3$. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and $R^6$ is $-CO_2CH_2CH_3$. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and t is 0. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and t is 1. In some embodiments is a compound of Formula (Ib), or a pharmaceutically acceptable salt or solvate thereof, wherein $R^1$ is $-(CR^4R^5)_t-C_{3-6}$cycloalkyl-$R^6$ and t is 2.

In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 0, and $R^4$ and $R^5$ is independently selected from H and $C_{1-6}$alkyl. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 1, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 2, and each $R^4$ and $R^5$ is each independently selected from H and $C_{1-6}$alkyl.

In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 0, and $R^4$ and $R^5$ are H. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 1, and each $R^4$ and $R^5$ is H. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2H$, t is 2, and each $R^4$ and $R^5$ is H.

In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 0, and $R^4$ and $R^5$ is independently selected from H and $C_{1-6}$alkyl. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 1, and each $R^4$ and $R^5$ is each independently selected from H and $C_{1-6}$alkyl. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 2, and each $R^4$ and $R^5$ is each independently selected from H and $C_{1-6}$alkyl.

In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 0, and $R^4$ and $R^5$ are H. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 1, and each $R^4$ and $R^5$ is H. In some embodiments is a compound of Formula (Ib), or a pharmaceutically acceptable salt or solvate thereof, wherein $R^1$ is $-(CR^4R^5)_t-C_{3-6}$cycloalkyl-$R^6$, $R^6$ is $-CO_2R^9$, $R^9$ is $C_{1-6}$alkyl, t is 2, and each $R^4$ and $R^5$ is H.

In some embodiments is a compound of Formula (Ib), or a pharmaceutically acceptable salt or solvate thereof, wherein $-X-R^1$ is $-OCH_2C(O)OH$. In some embodiments is a compound of Formula (Ib), or a pharmaceutically acceptable salt or solvate thereof, wherein $-X-R^1$ is $-N(H)CH_2C(O)OH$. In some embodiments is a compound of Formula (Ib), or a pharmaceutically acceptable salt or solvate thereof, wherein $-X-R^1$ is $-OCH(CH_3)C(O)OH$. In some embodiments is a compound of Formula (Ib), or a pharmaceutically acceptable salt or solvate thereof, wherein $-X-R^1$ is $-N(H)CH(CH_3)C(O)OH$. In some embodiments is a compound of Formula (Ib), or a pharmaceutically acceptable salt or solvate thereof, wherein $-X-R^1$ is $-OCH_2CH_2C(O)OH$. In some embodiments is a compound of Formula (Ib), or a pharmaceutically acceptable salt or solvate thereof, wherein $-X-R^1$ is $-N(H)CH_2CH_2C(O)OH$. In some embodiments is a compound of Formula (Ib), or a pharmaceutically acceptable salt or solvate thereof, wherein $-X-R^1$ is $-OCH_2CH_2CH_2C(O)OH$. In some embodiments is a compound of Formula (Ib), or a pharmaceutically acceptable salt or solvate thereof, wherein $-X-R^1$ is $-N(H)CH_2CH_2CH_2C(O)OH$. In some embodiments is a compound of Formula (Ib), or a pharmaceutically acceptable salt or solvate thereof, wherein $-X-R^1$ is $-OCH_2CH_2C(CH_3)_2C(O)OH$. In some embodiments is a compound of Formula (Ib), or a pharmaceutically acceptable salt or solvate thereof, wherein —X—$R^1$ is —N(H)CH$_2$CH$_2$C(CH$_3$)$_2$C(O)OH.

In some embodiments is a compound of Formula (Ib), or a pharmaceutically acceptable salt or solvate thereof, wherein —X—$R^1$ is —OCH$_2$C(O)OCH$_3$. In some embodiments is a compound of Formula (Ib), or a pharmaceutically acceptable salt or solvate thereof, wherein —X—$R^1$ is —N(H)CH$_2$C(O)OCH$_3$. In some embodiments is a compound of Formula (Ib), or a pharmaceutically acceptable salt or solvate thereof, wherein —X—$R^1$ is —OCH(CH$_3$)C(O)OCH$_3$. In some embodiments is a compound of Formula (Ib), or a pharmaceutically acceptable salt or solvate thereof, wherein —X—$R^1$ is —N(H)CH(CH$_3$)C(O)OCH$_3$. In some embodiments is a compound of Formula (Ib), or a pharmaceutically acceptable salt or solvate thereof, wherein —X—$R^1$ is —OCH$_2$CH$_2$C(O)OCH$_3$. In some embodiments is a compound of Formula (Ib), or a pharmaceutically acceptable salt or solvate thereof, wherein —X—$R^1$ is —N(H)CH$_2$CH$_2$C(O)OCH$_3$. In some embodiments is a compound of Formula (Ib), or a pharmaceutically acceptable salt or solvate thereof, wherein —X—$R^1$ is —OCH$_2$CH$_2$CH$_2$C(O)OCH$_3$. In some embodiments is a compound of Formula (Ib), or a pharmaceutically acceptable salt or solvate thereof, wherein —X—$R^1$ is —N(H)CH$_2$CH$_2$CH$_2$C(O)OCH$_3$. In some embodiments is a compound of Formula (Ib), or a pharmaceutically acceptable salt or solvate thereof, wherein —X—$R^1$ is —OCH$_2$CH$_2$C(CH$_3$)$_2$C(O)OCH$_3$. In some embodiments is a compound of Formula (Ib), or a pharmaceutically acceptable salt or solvate thereof, wherein —X—$R^1$ is —N(H)CH$_2$CH$_2$C(CH$_3$)$_2$C(O)OCH$_3$.

In some embodiments is a compound of Formula (Ib), or a pharmaceutically acceptable salt or solvate thereof, wherein —X—$R^1$ is —OCH$_2$CH$_2$OCH$_2$C(O)OH. In some embodiments is a compound of Formula (Ib), or a pharmaceutically acceptable salt or solvate thereof, wherein —X—$R^1$ is —N(H)CH$_2$CH$_2$OCH$_2$C(O)OH. In some embodiments is a compound of Formula (Ib), or a pharmaceutically acceptable salt or solvate thereof, wherein —X—$R^1$ is —OCH$_2$CH$_2$N(H)CH$_2$C(O)OH. In some embodiments is a compound of Formula (Ib), or a pharmaceutically acceptable salt or solvate thereof, wherein —X—$R^1$ is —N(H)CH$_2$CH$_2$N(SO$_2$CH$_3$)CH$_2$C(O)OH. In some embodiments is a compound of Formula (Ib), or a pharmaceutically acceptable salt or solvate thereof, wherein —X—$R^1$ is —OCH$_2$CH$_2$CH$_2$C(O)OCH(CH$_3$)OC(O)OCH$_2$CH$_3$. In some embodiments is a compound of Formula (Ib), or a pharmaceutically acceptable salt or solvate thereof, wherein —X—$R^1$ is —N(H)CH$_2$CH$_2$CH$_2$C(O)OCH(CH$_3$)OC(O)OCH(CH$_3$)$_2$. In some embodiments is a compound of Formula (Ib), or a pharmaceutically acceptable salt or solvate thereof, wherein —X—$R^1$ is —OCH$_2$CH$_2$CH$_2$C(O)OCH$_2$OC(O)OC(CH$_3$)$_3$. In some embodiments is a compound of Formula (Ib), or a pharmaceutically acceptable salt or solvate thereof, wherein —X—$R^1$ is —N(H)CH$_2$CH$_2$CH$_2$C(O)OCH(CH$_3$)OC(O)CH(CH$_3$)$_2$.

In some embodiments is a compound of Formula (Ib), or a pharmaceutically acceptable salt or solvate thereof, wherein —X—$R^1$ is —O-cyclopropyl-C(O)OH. In some embodiments is a compound of Formula (Ib), or a pharmaceutically acceptable salt or solvate thereof, wherein —X—$R^1$ is —N(H)-cyclopropyl-C(O)OH. In some embodiments is a compound of Formula (Ib), or a pharmaceutically acceptable salt or solvate thereof, wherein —X—$R^1$ is —O-cyclobutyl-C(O)OH. In some embodiments is a compound of Formula (Ib), or a pharmaceutically acceptable salt or solvate thereof, wherein —X—$R^1$ is —N(H)-cyclobutyl-C(O)OH.

In some embodiments is a compound of Formula (Ib), or a pharmaceutically acceptable salt or solvate thereof, wherein n is 0, 1, 2, or 3. In some embodiments is a compound of Formula (Ib), or a pharmaceutically acceptable salt or solvate thereof, wherein n is 0, 1, or 2. In some embodiments is a compound of Formula (Ib), or a pharmaceutically acceptable salt or solvate thereof, wherein n is 1 or 2. In some embodiments is a compound of Formula (Ib), or a pharmaceutically acceptable salt or solvate thereof, wherein n is 0 or 1. In some embodiments is a compound of Formula (Ib), or a pharmaceutically acceptable salt or solvate thereof, wherein n is 0. In some embodiments is a compound of Formula (Ib), or a pharmaceutically acceptable salt or solvate thereof, wherein n is 1. In some embodiments is a compound of Formula (Ib), or a pharmaceutically acceptable salt or solvate thereof, wherein n is 2. In some embodiments is a compound of Formula (Ib), or a pharmaceutically acceptable salt or solvate thereof, wherein n is 3. In some embodiments is a compound of Formula (Ib), or a pharmaceutically acceptable salt or solvate thereof, wherein n is 4.

In some embodiments is a compound of Formula (Ib), or a pharmaceutically acceptable salt or solvate thereof, wherein n is 1 and $R^2$ is halogen, $C_{1-6}$alkyl, $C_{1-6}$haloalkyl, or —OR$^{17}$. In some embodiments is a compound of Formula (Ib), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (Ib), or a pharmaceutically acceptable salt or solvate thereof, wherein n is 1 and $R^2$ is halogen. In some embodiments is a compound of Formula (Ib), or a pharmaceutically acceptable salt or solvate thereof, wherein n is 1 and $R^2$ is —Cl. In some embodiments is a compound of Formula (Ib), or a pharmaceutically acceptable salt or solvate thereof, wherein n is 1 and $R^2$ is —F. In some embodiments is a compound of Formula (Ib), or a pharmaceutically acceptable salt or solvate thereof, wherein n is 1 and $R^2$ is $C_{1-6}$alkyl. In some embodiments is a compound of Formula (Ib), or a pharmaceutically acceptable salt or solvate thereof, wherein n is 1 and $R^2$ is —CH$_3$. In some embodiments is a compound of Formula (Ib), or a pharmaceutically acceptable salt or solvate thereof, wherein n is 1 and $R^2$ is $C_{1-6}$haloalkyl. In some embodiments is a compound of Formula (Ib), or a pharmaceutically acceptable salt or solvate thereof, wherein n is 1 and $R^2$ is —CF$_3$. In some embodiments is a compound of Formula (Ib), or a pharmaceutically acceptable salt or solvate thereof, wherein n is 1 and $R^2$ is $C_{1-6}$alkoxy. In some embodiments is a compound of Formula (Ib), or a pharmaceutically acceptable salt or solvate thereof, wherein n is 1 and $R^2$ is —OCH$_3$. In some embodiments is a compound of Formula (Ib), or a pharmaceutically acceptable salt or solvate thereof, wherein n is 1 and $R^2$ is $C_{1-6}$haloalkoxy. In some embodiments is a compound of Formula (Ib), or a pharmaceutically acceptable salt or solvate thereof, wherein n is 1 and $R^2$ is —OCF$_3$. In some embodiments is a compound of Formula (Ib), or a pharmaceutically acceptable salt or solvate thereof, wherein n is 1 and $R^2$ is —OH. In some embodiments is a compound of Formula (Ib), or a pharmaceutically acceptable salt or solvate thereof, wherein n is 1 and $R^2$ is —CN.

In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, or —OR$^{17}$. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, or —OCF$_3$. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, or —OCF$_3$. In some embodiments is a compound of Formula (Ib), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (Ib), or a pharmaceutically acceptable salt or solvate thereof, wherein n is 2 and each $R^2$ is independently halogen or $C_{1-6}$haloalkyl. In some embodiments is a compound of Formula (Ib), or a pharmaceutically acceptable salt or solvate thereof, wherein n is 2 and each $R^2$ is independently halogen or $C_{1-6}$alkyl. In some embodiments is a compound of Formula (Ib), or a pharmaceutically acceptable salt or solvate thereof, wherein n is 2 and each $R^2$ is independently halogen. In some embodiments is a compound of Formula (Ib), or a pharmaceutically acceptable salt or solvate thereof, wherein n is 2 and each $R^2$ is independently $C_{1-6}$alkyl. In some embodiments is a compound of Formula (Ib), or a pharmaceutically acceptable salt or solvate thereof, wherein n is 2 and each $R^2$ is independently $C_{1-6}$haloalkyl.

In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, or —OR$^{17}$. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —OCF$_3$. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, or —OCF$_3$. In some embodiments is a compound of Formula (Ib), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (Ib), or a pharmaceutically acceptable salt or solvate thereof, wherein n is 3 and each $R^2$ is independently halogen or $C_{1-6}$haloalkyl. In some embodiments is a compound of Formula (Ib), or a pharmaceutically acceptable salt or solvate thereof, wherein n is 3 and each $R^2$ is independently halogen or $C_{1-6}$alkyl. In some embodiments is a compound of Formula (Ib), or a pharmaceutically acceptable salt or solvate thereof, wherein n is 3 and each $R^2$ is independently halogen. In some embodiments is a compound of Formula (Ib), or a pharmaceutically acceptable salt or solvate thereof, wherein n is 3 and each $R^2$ is independently $C_{1-6}$alkyl. In some embodiments is a compound of Formula (Ib), or a pharmaceutically acceptable salt or solvate thereof, wherein n is 3 and each $R^2$ is independently $C_{1-6}$haloalkyl.

In some embodiments is a compound of Formula (Ib), or a pharmaceutically acceptable salt or solvate thereof, wherein n is 4 and each $R^2$ is independently halogen, $C_{1-6}$alkyl, $C_{1-6}$haloalkyl, and —OR$^{17}$.

In some embodiments is a compound of Formula (Ibb):

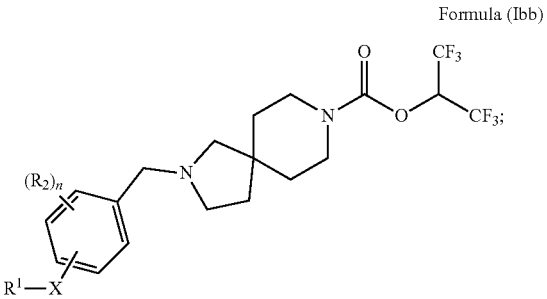

Formula (Ibb)

wherein:
X is —O— or —N(R$^3$)—;
R$^1$ is —(CR$^4$R$^5$)$_m$—R$^6$;
each R$^2$ is independently selected from halogen, $C_{1-6}$alkyl, or $C_{1-6}$haloalkyl;
R$^3$ is H or $C_{1-6}$alkyl;
each R$^4$ and R$^5$ is each independently selected from H, F, and $C_{1-6}$alkyl;
R$^6$ is —CO$_2$R$^9$;
R$^9$ is H or $C_{1-6}$alkyl;
m is 1, 2, 3 or 4; and
n is 0, 1, or 2;
or a pharmaceutically acceptable salt or solvate thereof.

In some embodiments is a compound of Formula (Ibb), or a pharmaceutically acceptable salt or solvate thereof, wherein X is —O—. In some embodiments is a compound of Formula (Ibb), or a pharmaceutically acceptable salt or solvate thereof, wherein X is —N(R$^3$)—. In some embodiments is a compound of Formula (Ibb), or a pharmaceutically acceptable salt or solvate thereof, wherein X is —N(H)—. In some embodiments is a compound of Formula (Ibb), or a pharmaceutically acceptable salt or solvate thereof, wherein X is —N(CH$_3$)—. In some embodiments is a compound of Formula (Ibb), or a pharmaceutically acceptable salt or solvate thereof, wherein X is —N(CH$_2$CH$_3$)—.

In some embodiments is a compound of Formula (Ibb), or a pharmaceutically acceptable salt or solvate thereof, wherein R$^1$ is —(CR$^4$R$^5$)$_m$—R$^6$. In some embodiments is a compound of Formula (Ibb), or a pharmaceutically acceptable salt or solvate thereof, wherein R$^1$ is —(CR$^4$R$^5$)$_m$—R$^6$ and R$^6$ is —CO$_2$R$^9$. In some embodiments is a compound of Formula (Ibb), or a pharmaceutically acceptable salt or solvate thereof, wherein R$^1$ is —(CR$^4$R$^5$)$_m$—R$^6$ and R$^6$ is —CO$_2$H. In some embodiments is a compound of Formula (Ibb), or a pharmaceutically acceptable salt or solvate thereof, wherein R$^1$ is —(CR$^4$R$^5$)$_m$—R$^6$ and R$^6$ is —CO$_2$CH$_3$. In some embodiments is a compound of Formula (Ibb), or a pharmaceutically acceptable salt or solvate thereof, wherein R$^1$ is —(CR$^4$R$^5$)$_m$—R$^6$ and R$^6$ is —CO$_2$CH$_2$CH$_3$. In some embodiments is a compound of Formula (Ibb), or a pharmaceutically acceptable salt or solvate thereof, wherein R$^1$ is —(CR$^4$R$^5$)$_m$—R$^6$ and m is 1.

In some embodiments is a compound of Formula (Ibb), or a pharmaceutically acceptable salt or solvate thereof, wherein $R^1$ is —$(CR^4R^5)_m$—$R^6$ and m is 2. In some embodiments is a compound of Formula (Ibb), or a pharmaceutically acceptable salt or solvate thereof, wherein $R^1$ is —$(CR^4R^5)_m$—$R^6$ and m is 3. In some embodiments is a compound of Formula (Ibb), or a pharmaceutically acceptable salt or solvate thereof, wherein $R^1$ is —$(CR^4R^5)_m$—$R^6$ and m is 4. In some embodiments is a compound of Formula (Ibb), or a pharmaceutically acceptable salt or solvate thereof, wherein $R^1$ is —$(CR^4R^5)_m$—$R^6$ and each $R^4$ and $R^5$ is each independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$ and each $R^4$ and $R^5$ is H.

In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ is independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is each independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is each independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is each independently selected from H and $C_{1-6}$alkyl.

In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ are H. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is H. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is H. In some embodiments is a compound of Formula (Ibb), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is H.

In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ is independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is each independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is each independently selected from H and $C_{1-6}$alkyl. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ are H. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is H. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is H. In some embodiments is a compound of Formula (Ibb), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is H.

In some embodiments is a compound of Formula (Ibb), or a pharmaceutically acceptable salt or solvate thereof, wherein —X—$R^1$ is —$OCH_2C(O)OH$. In some embodiments is a compound of Formula (Ibb), or a pharmaceutically acceptable salt or solvate thereof, wherein —X—$R^1$ is —$N(H)CH_2C(O)OH$. In some embodiments is a compound of Formula (Ibb), or a pharmaceutically acceptable salt or solvate thereof, wherein —X—$R^1$ is —$OCH(CH_3)C(O)OH$. In some embodiments is a compound of Formula (Ibb), or a pharmaceutically acceptable salt or solvate thereof, wherein —X—$R^1$ is —$N(H)CH(CH_3)C(O)OH$. In some embodiments is a compound of Formula (Ibb), or a pharmaceutically acceptable salt or solvate thereof, wherein —X—$R^1$ is —$OCH_2CH_2C(O)OH$. In some embodiments is a compound of Formula (Ibb), or a pharmaceutically acceptable salt or solvate thereof, wherein —X—$R^1$ is —$N(H)CH_2CH_2C(O)OH$. In some embodiments is a compound of Formula (Ibb), or a pharmaceutically acceptable salt or solvate thereof, wherein —X—$R^1$ is —$OCH_2CH_2CH_2C(O)OH$. In some embodiments is a compound of Formula (Ibb), or a pharmaceutically acceptable salt or solvate thereof, wherein —X—$R^1$ is —$N(H)CH_2CH_2CH_2C(O)OH$. In some embodiments is a compound of Formula (Ibb), or a pharmaceutically acceptable salt or solvate thereof, wherein —X—$R^1$ is —$OCH_2CH_2C(CH_3)_2C(O)OH$. In some embodiments is a compound of Formula (Ibb), or a pharmaceutically acceptable salt or solvate thereof, wherein —X—$R^1$ is —$N(H)CH_2CH_2C(CH_3)_2C(O)OH$.

In some embodiments is a compound of Formula (Ibb), or a pharmaceutically acceptable salt or solvate thereof, wherein —X—$R^1$ is —$OCH_2C(O)OCH_3$. In some embodiments is a compound of Formula (Ibb), or a pharmaceutically acceptable salt or solvate thereof, wherein —X—$R^1$ is —$N(H)CH_2C(O)OCH_3$. In some embodiments is a compound of Formula (Ibb), or a pharmaceutically acceptable salt or solvate thereof, wherein —X—$R^1$ is —$OCH(CH_3)C(O)OCH_3$. In some embodiments is a compound of Formula (Ibb), or a pharmaceutically acceptable salt or solvate thereof, wherein —X—$R^1$ is —$N(H)CH(CH_3)C(O)OCH_3$. In some embodiments is a compound of Formula (Ibb), or a pharmaceutically acceptable salt or solvate thereof, wherein —X—$R^1$ is —$OCH_2CH_2C(O)OCH_3$. In some embodiments is a compound of Formula (Ibb), or a pharmaceutically acceptable salt or solvate thereof, wherein —X—$R^1$ is —$N(H)CH_2CH_2C(O)OCH_3$. In some embodiments is a compound of Formula (Ibb), or a pharmaceutically acceptable salt or solvate thereof, wherein —X—$R^1$ is —$OCH_2CH_2CH_2C(O)OCH_3$. In some embodiments is a compound of Formula (Ibb), or a pharmaceutically acceptable salt or solvate thereof, wherein —X—$R^1$ is —$N(H)CH_2CH_2CH_2C(O)OCH_3$. In some embodiments is a compound of Formula (Ibb), or a pharmaceutically acceptable salt or solvate thereof, wherein —X—$R^1$ is —$OCH_2CH_2C(CH_3)_2C(O)OCH_3$. In some embodiments is a compound of Formula (Ibb), or a pharmaceutically acceptable salt or solvate thereof, wherein —X—R$^1$ is —N(H)CH$_2$CH$_2$C(CH$_3$)$_2$C(O)OCH$_3$.

In some embodiments is a compound of Formula (Ibb), or a pharmaceutically acceptable salt or solvate thereof, wherein n is 1 or 2. In some embodiments is a compound of Formula (Ibb), or a pharmaceutically acceptable salt or solvate thereof, wherein n is 0 or 1. In some embodiments is a compound of Formula (Ibb), or a pharmaceutically acceptable salt or solvate thereof, wherein n is 0. In some embodiments is a compound of Formula (Ibb), or a pharmaceutically acceptable salt or solvate thereof, wherein n is 1. In some embodiments is a compound of Formula (Ibb), or a pharmaceutically acceptable salt or solvate thereof, wherein n is 2.

In some embodiments is a compound of Formula (Ibb), or a pharmaceutically acceptable salt or solvate thereof, wherein n is 1 and R$^2$ is halogen, C$_{1-6}$alkyl, or C$_{1-6}$haloalkyl. In some embodiments is a compound of Formula (Ibb), or a pharmaceutically acceptable salt or solvate thereof, wherein n is 1 and R$^2$ is halogen. In some embodiments is a compound of Formula (Ibb), or a pharmaceutically acceptable salt or solvate thereof, wherein n is 1 and R$^2$ is —Cl. In some embodiments is a compound of Formula (Ibb), or a pharmaceutically acceptable salt or solvate thereof, wherein n is 1 and R$^2$ is —F. In some embodiments is a compound of Formula (Ibb), or a pharmaceutically acceptable salt or solvate thereof, wherein n is 1 and R$^2$ is C$_{1-6}$alkyl. In some embodiments is a compound of Formula (Ibb), or a pharmaceutically acceptable salt or solvate thereof, wherein n is 1 and R$^2$ is —CH$_3$. In some embodiments is a compound of Formula (Ibb), or a pharmaceutically acceptable salt or solvate thereof, wherein n is 1 and R$^2$ is C$_{1-6}$haloalkyl. In some embodiments is a compound of Formula (Ibb), or a pharmaceutically acceptable salt or solvate thereof, wherein n is 1 and R$^2$ is —CF$_3$.

In some embodiments is a compound of Formula (Ibb), or a pharmaceutically acceptable salt or solvate thereof, wherein n is 2 and each R$^2$ is independently halogen, C$_{1-6}$alkyl, or C$_{1-6}$haloalkyl. In some embodiments is a compound of Formula (Ibb), or a pharmaceutically acceptable salt or solvate thereof, wherein n is 2 and each R$^2$ is independently halogen or C$_{1-6}$haloalkyl. In some embodiments is a compound of Formula (Ibb), or a pharmaceutically acceptable salt or solvate thereof, wherein n is 2 and each R$^2$ is independently halogen or C$_{1-6}$alkyl. In some embodiments is a compound of Formula (Ibb), or a pharmaceutically acceptable salt or solvate thereof, wherein n is 2 and each R$^2$ is independently halogen. In some embodiments is a compound of Formula (Ibb), or a pharmaceutically acceptable salt or solvate thereof, wherein n is 2 and each R$^2$ is independently C$_{1-6}$alkyl. In some embodiments is a compound of Formula (Ibb), or a pharmaceutically acceptable salt or solvate thereof, wherein n is 2 and each R$^2$ is independently C$_{1-6}$haloalkyl.

In some embodiments is a compound of Formula (Ic):

Formula (Ic)

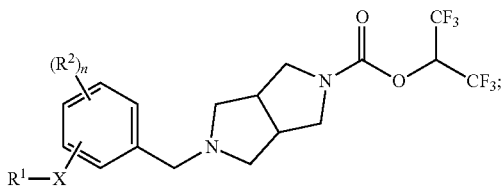

wherein:
X is —O—, —S—, —SO$_2$—, —N(R$^3$)—, or —CH$_2$—;
Y is —O— or —N(R$^7$)—;
R$^1$ is —(CR$^4$R$^5$)$_m$—R$^6$, —(CR$^4$R$^5$)$_p$—Y—(CR$^4$R$^5$)$_q$—R$^6$, or —(CR$^4$R$^5$)$_t$—C$_{3-6}$cycloalkyl-R$^6$; each R$^2$ is independently selected from halogen, —CN, C$_{1-6}$alkyl, C$_{1-6}$haloalkyl, —C$_{1-6}$alkyl(heterocycloalkyl), —OR$^{17}$, and —C(O)NR$^{18}$R$^{19}$;
R$^3$ is H or C$_{1-6}$alkyl;
each R$^4$ and R$^5$ is each independently selected from H, F, and C$_{1-6}$alkyl; or R$^4$ and R$^5$, together with the carbon to which they are attached, form a C$_{3-6}$cycloalkyl ring;
R$^6$ is —CO$_2$R$^9$, —C(O)R$^{10}$, or —C(O)O—(CR$^{12}$R$^{13}$)—OC(O)R$^{11}$;
R$^7$ is H, C$_{1-6}$alkyl, or —SO$_2$R$^8$;
R$^8$ is C$_{1-6}$alkyl;
R$^9$ is H or C$_{1-6}$alkyl;
R$^{10}$ is C$_{1-6}$alkyl or —NHSO$_2$R$^{21}$;
R$^{11}$ is C$_{1-6}$alkyl or C$_{1-6}$alkoxy;
R$^{12}$ and R$^{13}$ is each independently H or C$_{1-6}$alkyl;
each R$^{17}$ is independently selected from H, C$_{1-6}$alkyl, C$_{1-6}$haloalkyl, aminoalkyl, cycloalkyl, —C$_{1-6}$alkyl(heterocycloalkyl), —C$_{1-6}$alkyl-C(O)(heterocycloalkyl), optionally substituted heterocycloalkyl, optionally substituted aryl, and optionally substituted heteroaryl;
each R$^{18}$ and R$^{19}$ is independently selected from H, C$_{1-6}$alkyl, C$_{1-6}$haloalkyl, cycloalkyl, aryl, and heteroaryl; or R$^{18}$ and R$^{19}$, together with the nitrogen to which they are attached, form a heterocycloalkyl ring optionally substituted with one, two, or three R$^{20}$; each R$^{20}$ is independently selected from halogen, C$_{1-6}$alkyl, C$_{1-6}$haloalkyl, oxo, —CN, and C$_{3-6}$cycloalkyl;
R$^{21}$ is C$_{1-6}$alkyl;
m is 1, 2, 3 or 4;
n is 0, 1, 2, 3, or 4;
p is 2, 3, or 4;
q is 1, 2, or 3; and
t is 0, 1, or 2;
or a pharmaceutically acceptable salt or solvate thereof.

In some embodiments is a compound of Formula (Ic), or a pharmaceutically acceptable salt or solvate thereof, wherein X is —O—, —S—, —SO$_2$—, —N(R$^3$)—, or —CH$_2$—. In some embodiments is a compound of Formula (Ic), or a pharmaceutically acceptable salt or solvate thereof, wherein X is —O—. In some embodiments is a compound of Formula (Ic), or a pharmaceutically acceptable salt or solvate thereof, wherein X is —S—. In some embodiments is a compound of Formula (Ic), or a pharmaceutically acceptable salt or solvate thereof, wherein X is —SO$_2$—. In some embodiments is a compound of Formula (Ic), or a pharmaceutically acceptable salt or solvate thereof, wherein X is —N(R$^3$)—. In some embodiments is a compound of Formula (Ic), or a pharmaceutically acceptable salt or solvate thereof, wherein X is —N(H)—. In some embodiments is a compound of Formula (Ic), or a pharmaceutically acceptable salt or solvate thereof, wherein X is —N(CH$_3$)—. In some embodiments is a compound of Formula (Ic), or a pharmaceutically acceptable salt or solvate thereof, wherein X is —N(CH$_2$CH$_3$)—. In some embodiments is a compound of Formula (Ic), or a pharmaceutically acceptable salt or solvate thereof, wherein X is —CH$_2$—.

In some embodiments is a compound of Formula (Ic), or a pharmaceutically acceptable salt or solvate thereof, wherein R$^1$ is —(CR$^4$R$^5$)$_m$—R$^6$. In some embodiments is a compound of Formula (Ic), or a pharmaceutically acceptable salt or solvate thereof, wherein R$^1$ is —(CR$^4$R$^5$)$_m$—R$^6$ and $R^6$ is —$CO_2R^9$. In some embodiments is a compound of Formula (Ic), or a pharmaceutically acceptable salt or solvate thereof, wherein $R^1$ is —$(CR^4R^5)_m$—$R^6$ and $R^6$ is —$CO_2H$. In some embodiments is a compound of Formula (Ic), or a pharmaceutically acceptable salt or solvate thereof, wherein $R^1$ is —$(CR^4R^5)_m$—$R^6$ and $R^6$ is —$CO_2CH_3$. In some embodiments is a compound of Formula (Ic), or a pharmaceutically acceptable salt or solvate thereof, wherein $R^1$ is —$(CR^4R^5)_m$—$R^6$ and $R^6$ is —$CO_2CH_2CH_3$. In some embodiments is a compound of Formula (Ic), or a pharmaceutically acceptable salt or solvate thereof, wherein $R^1$ is —$(CR^4R^5)_m$—$R^6$ and $R^6$ is —$C(O)R^{10}$. In some embodiments is a compound of Formula (Ic), or a pharmaceutically acceptable salt or solvate thereof, wherein $R^1$ is —$(CR^4R^5)_m$—$R^6$ and $R^6$ is —$C(O)NHSO_2CH_3$. In some embodiments is a compound of Formula (Ic), or a pharmaceutically acceptable salt or solvate thereof, wherein $R^1$ is —$(CR^4R^5)_m$—$R^6$ and $R^6$ is —$C(O)O$—$(CR^{12}R^{13})$—$OC(O)R^{11}$. In some embodiments is a compound of Formula (Ic), or a pharmaceutically acceptable salt or solvate thereof, wherein $R^1$ is —$(CR^4R^5)_m$—$R^6$ and $R^6$ is —$C(O)OCH_2OC(O)R^{11}$. In some embodiments is a compound of Formula (Ic), or a pharmaceutically acceptable salt or solvate thereof, wherein $R^1$ is —$(CR^4R^5)_m$—$R^6$ and $R^6$ is —$C(O)OCH_2OC(O)OCH_2CH_3$. In some embodiments is a compound of Formula (Ic), or a pharmaceutically acceptable salt or solvate thereof, wherein $R^1$ is —$(CR^4R^5)_m$—$R^6$ and $R^6$ is —$C(O)OCH_2OC(O)OCH(CH_3)_2$. In some embodiments is a compound of Formula (Ic), or a pharmaceutically acceptable salt or solvate thereof, wherein $R^1$ is —$(CR^4R^5)_m$—$R^6$ and $R^6$ is —$C(O)OCH_2OC(O)OC(CH_3)_3$. In some embodiments is a compound of Formula (Ic), or a pharmaceutically acceptable salt or solvate thereof, wherein $R^1$ is —$(CR^4R^5)_m$—$R^6$ and $R^6$ is —$C(O)OCH_2OC(O)CH(CH_3)_2$. In some embodiments is a compound of Formula (Ic), or a pharmaceutically acceptable salt or solvate thereof, wherein $R^1$ is —$(CR^4R^5)_m$—$R^6$ and m is 1. In some embodiments is a compound of Formula (Ic), or a pharmaceutically acceptable salt or solvate thereof, wherein $R^1$ is —$(CR^4R^5)_m$—$R^6$ and m is 2. In some embodiments is a compound of Formula (Ic), or a pharmaceutically acceptable salt or solvate thereof, wherein $R^1$ is —$(CR^4R^5)_m$—$R^6$ and m is 3. In some embodiments is a compound of Formula (Ic), or a pharmaceutically acceptable salt or solvate thereof, wherein $R^1$ is —$(CR^4R^5)_m$—$R^6$ and m is 4. In some embodiments is a compound of Formula (Ic), or a pharmaceutically acceptable salt or solvate thereof, wherein $R^1$ is —$(CR^4R^5)_m$—$R^6$ and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$ and each $R^4$ and $R^5$ is H.

In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ is independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is each independently selected from H and $C_{1-6}$alkyl.

In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ are H. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is H. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is H. In some embodiments is a compound of Formula (Ic), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is H.

In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ is independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ are H. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is H. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is H. In some embodiments is a compound of Formula (Ic), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is H.

In some embodiments is a compound of Formula (Ic), or a pharmaceutically acceptable salt or solvate thereof, wherein $R^1$ is —$(CR^4R^5)_p$—Y—$(CR^4R^5)_q$—$R^6$. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and $R^6$ is —$CO_2R^9$. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and $R^6$ is —$CO_2H$. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and $R^6$ is —$CO_2CH_3$. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and $R^6$ is —$CO_2CH_2CH_3$. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and Y is —O—. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and Y is —$N(R^7)$—. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and Y is —N(H)—. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and Y is —$N(SO_2Me)$—. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and p is 2. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and p is 3. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and p is 4. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and q is 1. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and q is 2. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and q is 3. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$ and each $R^4$ and $R^5$ is H.

In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —O—, p is 2, q is 1, and $R^4$ and $R^5$ is independently selected from H and $C_{1-6}$alkyl. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —N(H)—, p is 2, q is 1, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —$N(SO_2Me)$—, p is 2, q is 1, and each $R^4$ and $R^5$ is each independently selected from H and $C_{1-6}$alkyl.

In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —O—, p is 2, q is 1, and $R^4$ and $R^5$ are H. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —N(H)—, p is 2, q is 1, and each $R^4$ and $R^5$ is H. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2H$, Y is —$N(SO_2Me)$—, p is 2, q is 1, and each $R^4$ and $R^5$ is H.

In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —O—, p is 2, q is 1, and $R^4$ and $R^5$ is independently selected from H and $C_{1-6}$alkyl. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —N(H)—, p is 2, q is 1, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —$N(SO_2Me)$—, p is 2, q is 1, and each $R^4$ and $R^5$ is each independently selected from H and $C_{1-6}$alkyl.

In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —O—, p is 2, q is 1, and $R^4$ and $R^5$ are H. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —N(H)—, p is 2, q is 1, and each $R^4$ and $R^5$ is H. In some embodiments is a compound of Formula (Ic), or a pharmaceutically acceptable salt or solvate thereof, wherein $R^1$ is —$(CR^4R^5)_p$—Y—$(CR^4R^5)_q$—$R^6$, $R^6$ is —$CO_2R^9$, $R^9$ is $C_{1-6}$alkyl, Y is —$N(SO_2Me)$—, p is 2, q is 1, and each $R^4$ and $R^5$ is H.

In some embodiments is a compound of Formula (Ic), or a pharmaceutically acceptable salt or solvate thereof, wherein $R^1$ is —$(CR^4R^5)_t$—$C_{3-6}$cycloalkyl-$R^6$. In some embodiments is a compound of Formula (Ic), or a pharmaceutically acceptable salt or solvate thereof, wherein $R^1$ is —$(CR^4R^5)_t$-cyclopropyl-$R^6$. In some embodiments is a compound of Formula (Ic), or a pharmaceutically acceptable salt or solvate thereof, wherein $R^1$ is —$(CR^4R^5)_t$-cyclobutyl-$R^6$. In some embodiments is a compound of Formula (Ic), or a pharmaceutically acceptable salt or solvate thereof, wherein $R^1$ is —$(CR^4R^5)_t$-cyclopentyl-$R^6$. In some embodiments is a compound of Formula (Ic), or a pharmaceutically acceptable salt or solvate thereof, wherein $R^1$ is —$(CR^4R^5)_t$-cyclohexyl-$R^6$. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and $R^6$ is —$CO_2R^9$. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and $R^6$ is —$CO_2H$. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and $R^6$ is —$CO_2CH_3$. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and $R^6$ is —$CO_2CH_2CH_3$. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and t is 0. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and t is 1. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$ and t is 2.

In some embodiments is a compound of Formula (Ic), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 0, and $R^4$ and $R^5$ is independently selected from H and $C_{1-6}$alkyl. In some embodiments is a compound of Formula (Ic), or a pharmaceutically acceptable salt or solvate thereof, wherein $R^1$ is —$(CR^4R^5)_t$—$C_{3-6}$cycloalkyl-$R^6$, $R^6$ is —$CO_2H$, t is 1, and each $R^4$ and $R^5$ is each independently selected from H and $C_{1-6}$alkyl. In some embodiments is a compound of Formula (Ic), or a pharmaceutically acceptable salt or solvate thereof, wherein $R^1$ is —(CR⁴R⁵)$_t$—C$_{3-6}$cycloalkyl-R⁶, R⁶ is —CO$_2$H, t is 2, and each R⁴ and R⁵ is each independently selected from H and C$_{1-6}$alkyl.

In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$H, t is 0, and R⁴ and R⁵ are H. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$H, t is 1, and each R⁴ and R⁵ is H. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$H, t is 2, and each R⁴ and R⁵ is H.

In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 0, and R⁴ and R⁵ is independently selected from H and C$_{1-6}$alkyl. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 1, and each R⁴ and R⁵ is each independently selected from H and C$_{1-6}$alkyl. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 2, and each R⁴ and R⁵ is each independently selected from H and C$_{1-6}$alkyl.

In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 0, and R⁴ and R⁵ are H. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 1, and each R⁴ and R⁵ is H. In some embodiments is a compound of Formula (Ic), or a pharmaceutically acceptable salt or solvate thereof, wherein R¹ is —(CR⁴R⁵)$_t$—C$_{3-6}$cycloalkyl-R⁶, R⁶ is —CO$_2$R⁹, R⁹ is C$_{1-6}$alkyl, t is 2, and each R⁴ and R⁵ is H.

In some embodiments is a compound of Formula (Ic), or a pharmaceutically acceptable salt or solvate thereof, wherein —X—R¹ is —OCH$_2$C(O)OH. In some embodiments is a compound of Formula (Ic), or a pharmaceutically acceptable salt or solvate thereof, wherein —X—R¹ is —N(H)CH$_2$C(O)OH. In some embodiments is a compound of Formula (Ic), or a pharmaceutically acceptable salt or solvate thereof, wherein —X—R¹ is —OCH(CH$_3$)C(O)OH. In some embodiments is a compound of Formula (Ic), or a pharmaceutically acceptable salt or solvate thereof, wherein —X—R¹ is —N(H)CH(CH$_3$)C(O)OH. In some embodiments is a compound of Formula (Ic), or a pharmaceutically acceptable salt or solvate thereof, wherein —X—R¹ is —OCH$_2$CH$_2$C(O)OH. In some embodiments is a compound of Formula (Ic), or a pharmaceutically acceptable salt or solvate thereof, wherein —X—R¹ is —N(H)CH$_2$CH$_2$C(O)OH. In some embodiments is a compound of Formula (Ic), or a pharmaceutically acceptable salt or solvate thereof, wherein —X—R¹ is —OCH$_2$CH$_2$CH$_2$C(O)OH. In some embodiments is a compound of Formula (Ic), or a pharmaceutically acceptable salt or solvate thereof, wherein —X—R¹ is —N(H)CH$_2$CH$_2$CH$_2$C(O)OH. In some embodiments is a compound of Formula (Ic), or a pharmaceutically acceptable salt or solvate thereof, wherein —X—R¹ is —OCH$_2$C(CH$_3$)$_2$C(O)OH. In some embodiments is a compound of Formula (Ic), or a pharmaceutically acceptable salt or solvate thereof, wherein —X—R¹ is —N(H)CH$_2$C(CH$_3$)$_2$C(O)OH.

In some embodiments is a compound of Formula (Ic), or a pharmaceutically acceptable salt or solvate thereof, wherein —X—R¹ is —OCH$_2$C(O)OCH$_3$. In some embodiments is a compound of Formula (Ic), or a pharmaceutically acceptable salt or solvate thereof, wherein —X—R¹ is —N(H)CH$_2$C(O)OCH$_3$. In some embodiments is a compound of Formula (Ic), or a pharmaceutically acceptable salt or solvate thereof, wherein —X—R¹ is —OCH(CH$_3$)C(O)OCH$_3$. In some embodiments is a compound of Formula (Ic), or a pharmaceutically acceptable salt or solvate thereof, wherein —X—R¹ is —N(H)CH(CH$_3$)C(O)OCH$_3$. In some embodiments is a compound of Formula (Ic), or a pharmaceutically acceptable salt or solvate thereof, wherein —X—R¹ is —OCH$_2$CH$_2$C(O)OCH$_3$. In some embodiments is a compound of Formula (Ic), or a pharmaceutically acceptable salt or solvate thereof, wherein —X—R¹ is —N(H)CH$_2$CH$_2$C(O)OCH$_3$. In some embodiments is a compound of Formula (Ic), or a pharmaceutically acceptable salt or solvate thereof, wherein —X—R¹ is —OCH$_2$CH$_2$CH$_2$C(O)OCH$_3$. In some embodiments is a compound of Formula (Ic), or a pharmaceutically acceptable salt or solvate thereof, wherein —X—R¹ is —N(H)CH$_2$CH$_2$CH$_2$C(O)OCH$_3$. In some embodiments is a compound of Formula (Ic), or a pharmaceutically acceptable salt or solvate thereof, wherein —X—R¹ is —OCH$_2$CH$_2$C(CH$_3$)$_2$C(O)OCH$_3$. In some embodiments is a compound of Formula (Ic), or a pharmaceutically acceptable salt or solvate thereof, wherein —X—R¹ is —N(H)CH$_2$CH$_2$C(CH$_3$)$_2$C(O)OCH$_3$.

In some embodiments is a compound of Formula (Ic), or a pharmaceutically acceptable salt or solvate thereof, wherein —X—R¹ is —OCH$_2$CH$_2$OCH$_2$C(O)OH. In some embodiments is a compound of Formula (Ic), or a pharmaceutically acceptable salt or solvate thereof, wherein —X—R¹ is —N(H)CH$_2$CH$_2$OCH$_2$C(O)OH. In some embodiments is a compound of Formula (Ic), or a pharmaceutically acceptable salt or solvate thereof, wherein —X—R¹ is —OCH$_2$CH$_2$N(H)CH$_2$C(O)OH. In some embodiments is a compound of Formula (Ic), or a pharmaceutically acceptable salt or solvate thereof, wherein —X—R¹ is —N(H)CH$_2$CH$_2$N(SO$_2$CH$_3$)CH$_2$C(O)OH. In some embodiments is a compound of Formula (Ic), or a pharmaceutically acceptable salt or solvate thereof, wherein —X—R¹ is —OCH$_2$CH$_2$CH$_2$C(O)OCH(CH$_3$)OC(O)OCH$_2$CH$_3$. In some embodiments is a compound of Formula (Ic), or a pharmaceutically acceptable salt or solvate thereof, wherein —X—R¹ is —N(H)CH$_2$CH$_2$CH$_2$C(O)OCH(CH$_3$)OC(O)OCH(CH$_3$)$_2$. In some embodiments is a compound of Formula (Ic), or a pharmaceutically acceptable salt or solvate thereof, wherein —X—R¹ is —OCH$_2$CH$_2$CH$_2$C(O)OCH$_2$OC(O)OC(CH$_3$)$_3$. In some embodiments is a compound of Formula (Ic), or a pharmaceutically acceptable salt or solvate thereof, wherein —X—R¹ is —N(H)CH$_2$CH$_2$CH$_2$C(O)OCH(CH$_3$)OC(O)CH(CH$_3$)$_2$.

In some embodiments is a compound of Formula (Ic), or a pharmaceutically acceptable salt or solvate thereof, wherein —X—R¹ is —O-cyclopropyl-C(O)OH. In some embodiments is a compound of Formula (Ic), or a pharmaceutically acceptable salt or solvate thereof, wherein —X—R¹ is —N(H)-cyclopropyl-C(O)OH. In some embodiments is a compound of Formula (Ic), or a pharmaceutically acceptable salt or solvate thereof, wherein —X—R¹ is —O-cyclobutyl-C(O)OH. In some embodiments is a compound of Formula (Ic), or a pharmaceutically acceptable salt or solvate thereof, wherein —X—R$^1$ is —N(H)-cyclobutyl-C(O)OH.

In some embodiments is a compound of Formula (Ic), or a pharmaceutically acceptable salt or solvate thereof, wherein n is 0, 1, 2, or 3. In some embodiments is a compound of Formula (Ic), or a pharmaceutically acceptable salt or solvate thereof, wherein n is 0, 1, or 2. In some embodiments is a compound of Formula (Ic), or a pharmaceutically acceptable salt or solvate thereof, wherein n is 1 or 2. In some embodiments is a compound of Formula (Ic), or a pharmaceutically acceptable salt or solvate thereof, wherein n is 0 or 1. In some embodiments is a compound of Formula (Ic), or a pharmaceutically acceptable salt or solvate thereof, wherein n is 0. In some embodiments is a compound of Formula (Ic), or a pharmaceutically acceptable salt or solvate thereof, wherein n is 1. In some embodiments is a compound of Formula (Ic), or a pharmaceutically acceptable salt or solvate thereof, wherein n is 2. In some embodiments is a compound of Formula (Ic), or a pharmaceutically acceptable salt or solvate thereof, wherein n is 3. In some embodiments is a compound of Formula (Ic), or a pharmaceutically acceptable salt or solvate thereof, wherein n is 4.

In some embodiments is a compound of Formula (Ic), or a pharmaceutically acceptable salt or solvate thereof, wherein n is 1 and R$^2$ is halogen, $C_{1-6}$alkyl, $C_{1-6}$haloalkyl, or —OR$^{17}$. In some embodiments is a compound of Formula (Ic), or a pharmaceutically acceptable salt or solvate thereof, wherein n is 1 and R$^2$ is halogen, $C_{1-6}$alkyl, or $C_{1-6}$haloalkyl. In some embodiments is a compound of Formula (Ic), or a pharmaceutically acceptable salt or solvate thereof, wherein n is 1 and R$^2$ is halogen. In some embodiments is a compound of Formula (Ic), or a pharmaceutically acceptable salt or solvate thereof, wherein n is 1 and R$^2$ is —Cl. In some embodiments is a compound of Formula (Ic), or a pharmaceutically acceptable salt or solvate thereof, wherein n is 1 and R$^2$ is —F. In some embodiments is a compound of Formula (Ic), or a pharmaceutically acceptable salt or solvate thereof, wherein n is 1 and R$^2$ is $C_{1-6}$alkyl. In some embodiments is a compound of Formula (Ic), or a pharmaceutically acceptable salt or solvate thereof, wherein n is 1 and R$^2$ is —CH$_3$. In some embodiments is a compound of Formula (Ic), or a pharmaceutically acceptable salt or solvate thereof, wherein n is 1 and R$^2$ is $C_{1-6}$haloalkyl. In some embodiments is a compound of Formula (Ic), or a pharmaceutically acceptable salt or solvate thereof, wherein n is 1 and R$^2$ is —CF$_3$. In some embodiments is a compound of Formula (Ic), or a pharmaceutically acceptable salt or solvate thereof, wherein n is 1 and R$^2$ is $C_{1-6}$alkoxy. In some embodiments is a compound of Formula (Ic), or a pharmaceutically acceptable salt or solvate thereof, wherein n is 1 and R$^2$ is —OCH$_3$. In some embodiments is a compound of Formula (Ic), or a pharmaceutically acceptable salt or solvate thereof, wherein n is 1 and R$^2$ is $C_{1-6}$haloalkoxy. In some embodiments is a compound of Formula (Ic), or a pharmaceutically acceptable salt or solvate thereof, wherein n is 1 and R$^2$ is —OCF$_3$. In some embodiments is a compound of Formula (Ic), or a pharmaceutically acceptable salt or solvate thereof, wherein n is 1 and R$^2$ is —OH. In some embodiments is a compound of Formula (Ic), or a pharmaceutically acceptable salt or solvate thereof, wherein n is 1 and R$^2$ is —CN.

In some embodiments is a compound of Formula (Ic), or a pharmaceutically acceptable salt or solvate thereof, wherein n is 2 and each R$^2$ is independently halogen, $C_{1-6}$alkyl, $C_{1-6}$haloalkyl, or —OR$^{17}$. In some embodiments is a compound of Formula (Ic), or a pharmaceutically acceptable salt or solvate thereof, wherein n is 2 and each R$^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ic), or a pharmaceutically acceptable salt or solvate thereof, wherein n is 2 and each R$^2$ is independently halogen, $C_{1-6}$alkyl, $C_{1-6}$haloalkyl, $C_{1-6}$alkoxy, —OCF$_3$, or —CN. In some embodiments is a compound of Formula (Ic), or a pharmaceutically acceptable salt or solvate thereof, wherein n is 2 and each R$^2$ is independently halogen, $C_{1-6}$alkyl, $C_{1-6}$haloalkyl, $C_{1-6}$alkoxy, or —OCF$_3$. In some embodiments is a compound of Formula (Ic), or a pharmaceutically acceptable salt or solvate thereof, wherein n is 2 and each R$^2$ is independently halogen, $C_{1-6}$alkyl, $C_{1-6}$haloalkyl, or —OCF$_3$. In some embodiments is a compound of Formula (Ic), or a pharmaceutically acceptable salt or solvate thereof, wherein n is 2 and each R$^2$ is independently halogen, $C_{1-6}$alkyl, or $C_{1-6}$haloalkyl. In some embodiments is a compound of Formula (Ic), or a pharmaceutically acceptable salt or solvate thereof, wherein n is 2 and each R$^2$ is independently halogen or $C_{1-6}$haloalkyl. In some embodiments is a compound of Formula (Ic), or a pharmaceutically acceptable salt or solvate thereof, wherein n is 2 and each R$^2$ is independently halogen or $C_{1-6}$alkyl. In some embodiments is a compound of Formula (Ic), or a pharmaceutically acceptable salt or solvate thereof, wherein n is 2 and each R$^2$ is independently halogen. In some embodiments is a compound of Formula (Ic), or a pharmaceutically acceptable salt or solvate thereof, wherein n is 2 and each R$^2$ is independently $C_{1-6}$alkyl. In some embodiments is a compound of Formula (Ic), or a pharmaceutically acceptable salt or solvate thereof, wherein n is 2 and each R$^2$ is independently $C_{1-6}$haloalkyl.

In some embodiments is a compound of Formula (Ic), or a pharmaceutically acceptable salt or solvate thereof, wherein n is 3 and each R$^2$ is independently halogen, $C_{1-6}$alkyl, $C_{1-6}$haloalkyl, or —OR$^{17}$. In some embodiments is a compound of Formula (Ic), or a pharmaceutically acceptable salt or solvate thereof, wherein n is 3 and each R$^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ic), or a pharmaceutically acceptable salt or solvate thereof, wherein n is 3 and each R$^2$ is independently halogen, $C_{1-6}$alkyl, $C_{1-6}$haloalkyl, $C_{1-6}$alkoxy, —OCF$_3$, or —CN. In some embodiments is a compound of Formula (Ic), or a pharmaceutically acceptable salt or solvate thereof, wherein n is 3 and each R$^2$ is independently halogen, $C_{1-6}$alkyl, $C_{1-6}$haloalkyl, $C_{1-6}$alkoxy, or —OCF$_3$. In some embodiments is a compound of Formula (Ic), or a pharmaceutically acceptable salt or solvate thereof, wherein n is 3 and each R$^2$ is independently halogen, $C_{1-6}$alkyl, $C_{1-6}$haloalkyl, or —OCF$_3$. In some embodiments is a compound of Formula (Ic), or a pharmaceutically acceptable salt or solvate thereof, wherein n is 3 and each R$^2$ is independently halogen, $C_{1-6}$alkyl, or $C_{1-6}$haloalkyl. In some embodiments is a compound of Formula (Ic), or a pharmaceutically acceptable salt or solvate thereof, wherein n is 3 and each R$^2$ is independently halogen or $C_{1-6}$haloalkyl. In some embodiments is a compound of Formula (Ic), or a pharmaceutically acceptable salt or solvate thereof, wherein n is 3 and each R$^2$ is independently halogen or $C_{1-6}$alkyl. In some embodiments is a compound of Formula (Ic), or a pharmaceutically acceptable salt or solvate thereof, wherein n is 3 and each R$^2$ is independently halogen. In some embodiments is a compound of Formula (Ic), or a pharmaceutically acceptable salt or solvate thereof, wherein n is 3 and each $R^2$ is independently $C_{1-6}$alkyl. In some embodiments is a compound of Formula (Ic), or a pharmaceutically acceptable salt or solvate thereof, wherein n is 3 and each $R^2$ is independently $C_{1-6}$haloalkyl.

In some embodiments is a compound of Formula (Ic), or a pharmaceutically acceptable salt or solvate thereof, wherein n is 4 and each $R^2$ is independently halogen, $C_{1-6}$alkyl, $C_{1-6}$haloalkyl, and —$OR^{17}$.

In some embodiments is a compound of Formula (Icc):

Formula (Icc)

wherein:
X is —O— or —N($R^3$)—;
$R^1$ is —$(CR^4R^5)_m$—$R^6$;
each $R^2$ is independently selected from halogen, $C_{1-6}$alkyl, or $C_{1-6}$haloalkyl;
$R^3$ is H or $C_{1-6}$alkyl;
each $R^4$ and $R^5$ is each independently selected from H, F, and $C_{1-6}$alkyl;
$R^6$ is —$CO_2R^9$;
$R^9$ is H or $C_{1-6}$alkyl;
m is 1, 2, 3 or 4; and
n is 0, 1, or 2;
or a pharmaceutically acceptable salt or solvate thereof.

In some embodiments is a compound of Formula (Icc), or a pharmaceutically acceptable salt or solvate thereof, wherein X is —O—. In some embodiments is a compound of Formula (Icc), or a pharmaceutically acceptable salt or solvate thereof, wherein X is —N($R^3$)—. In some embodiments is a compound of Formula (Icc), or a pharmaceutically acceptable salt or solvate thereof, wherein X is —N(H)—. In some embodiments is a compound of Formula (Icc), or a pharmaceutically acceptable salt or solvate thereof, wherein X is —N($CH_3$)—. In some embodiments is a compound of Formula (Icc), or a pharmaceutically acceptable salt or solvate thereof, wherein X is —N($CH_2CH_3$)—.

In some embodiments is a compound of Formula (Icc), or a pharmaceutically acceptable salt or solvate thereof, wherein $R^1$ is —$(CR^4R^5)_m$—$R^6$. In some embodiments is a compound of Formula (Icc), or a pharmaceutically acceptable salt or solvate thereof, wherein $R^1$ is —$(CR^4R^5)_m$—$R^6$ and $R^6$ is —$CO_2R^9$. In some embodiments is a compound of Formula (Icc), or a pharmaceutically acceptable salt or solvate thereof, wherein $R^1$ is —$(CR^4R^5)_m$—$R^6$ and $R^6$ is —$CO_2H$. In some embodiments is a compound of Formula (Icc), or a pharmaceutically acceptable salt or solvate thereof, wherein $R^1$ is —$(CR^4R^5)_m$—$R^6$ and $R^6$ is —$CO_2CH_3$. In some embodiments is a compound of Formula (Icc), or a pharmaceutically acceptable salt or solvate thereof, wherein $R^1$ is —$(CR^4R^5)_m$—$R^6$ and $R^6$ is —$CO_2CH_2CH_3$. In some embodiments is a compound of Formula (Icc), or a pharmaceutically acceptable salt or solvate thereof, wherein $R^1$ is —$(CR^4R^5)_m$—$R^6$ and m is 1. In some embodiments is a compound of Formula (Icc), or a pharmaceutically acceptable salt or solvate thereof, wherein $R^1$ is —$(CR^4R^5)_m$—$R^6$ and m is 2. In some embodiments is a compound of Formula (Icc), or a pharmaceutically acceptable salt or solvate thereof, wherein $R^1$ is —$(CR^4R^5)_m$—$R^6$ and m is 3. In some embodiments is a compound of Formula (Icc), or a pharmaceutically acceptable salt or solvate thereof, wherein $R^1$ is —$(CR^4R^5)_m$—$R^6$ and m is 4. In some embodiments is a compound of Formula (Icc), or a pharmaceutically acceptable salt or solvate thereof, wherein $R^1$ is —$(CR^4R^5)_m$—$R^6$ and each $R^4$ and $R^5$ is each independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$ and each $R^4$ and $R^5$ is H.

In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ is independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is each independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is each independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is each independently selected from H and $C_{1-6}$alkyl.

In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 1, and $R^4$ and $R^5$ are H. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 2, and each $R^4$ and $R^5$ is H. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 3, and each $R^4$ and $R^5$ is H. In some embodiments is a compound of Formula (Icc), or a pharmaceutically acceptable salt or solvate thereof, wherein $R^1$ is —$(CR^4R^5)_m$—$R^6$, $R^6$ is —$CO_2H$, m is 4, and each $R^4$ and $R^5$ is H.

In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ is independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is each independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 3, and each $R^4$ and $R^5$ is each independently selected from H and $C_{1-6}$alkyl. In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 4, and each $R^4$ and $R^5$ is each independently selected from H and $C_{1-6}$alkyl.

In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 1, and $R^4$ and $R^5$ are H. In some embodiments is a compound of Formula (Icc), or a pharmaceutically acceptable salt or solvate thereof, wherein $R^1$ is —$(CR^4R^5)_m$—$R^6$, $R^6$ is —$CO_2R^9$, $R^9$ is $C_{1-6}$alkyl, m is 2, and each $R^4$ and $R^5$ is H. In some embodiments is a compound of Formula (Icc), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 3, and each $R^4$ and $R^5$ is H. In some embodiments is a compound of Formula (Icc), or a pharmaceutically acceptable salt or solvate thereof, wherein $R^1$ is $-(CR^4R^5)_m-R^6$, $R^6$ is $-CO_2R^9$, $R^9$ is $C_{1-6}$alkyl, m is 4, and each $R^4$ and $R^5$ is H.

In some embodiments is a compound of Formula (Icc), or a pharmaceutically acceptable salt or solvate thereof, wherein $-X-R^1$ is $-OCH_2C(O)OH$. In some embodiments is a compound of Formula (Icc), or a pharmaceutically acceptable salt or solvate thereof, wherein $-X-R^1$ is $-N(H)CH_2C(O)OH$. In some embodiments is a compound of Formula (Icc), or a pharmaceutically acceptable salt or solvate thereof, wherein $-X-R^1$ is $-OCH(CH_3)C(O)OH$. In some embodiments is a compound of Formula (Icc), or a pharmaceutically acceptable salt or solvate thereof, wherein $-X-R^1$ is $-N(H)CH(CH_3)C(O)OH$. In some embodiments is a compound of Formula (Icc), or a pharmaceutically acceptable salt or solvate thereof, wherein $-X-R^1$ is $-OCH_2CH_2C(O)OH$. In some embodiments is a compound of Formula (Icc), or a pharmaceutically acceptable salt or solvate thereof, wherein $-X-R^1$ is $-N(H)CH_2CH_2C(O)OH$. In some embodiments is a compound of Formula (Icc), or a pharmaceutically acceptable salt or solvate thereof, wherein $-X-R^1$ is $-OCH_2CH_2CH_2C(O)OH$. In some embodiments is a compound of Formula (Icc), or a pharmaceutically acceptable salt or solvate thereof, wherein $-X-R^1$ is $-N(H)CH_2CH_2CH_2C(O)OH$. In some embodiments is a compound of Formula (Icc), or a pharmaceutically acceptable salt or solvate thereof, wherein $-X-R^1$ is $-OCH_2CH_2C(CH_3)_2C(O)OH$. In some embodiments is a compound of Formula (Icc), or a pharmaceutically acceptable salt or solvate thereof, wherein $-X-R^1$ is $-N(H)CH_2CH_2C(CH_3)_2C(O)OH$.

In some embodiments is a compound of Formula (Icc), or a pharmaceutically acceptable salt or solvate thereof, wherein $-X-R^1$ is $-OCH_2C(O)OCH_3$. In some embodiments is a compound of Formula (Icc), or a pharmaceutically acceptable salt or solvate thereof, wherein $-X-R^1$ is $-N(H)CH_2C(O)OCH_3$. In some embodiments is a compound of Formula (Icc), or a pharmaceutically acceptable salt or solvate thereof, wherein $-X-R^1$ is $-OCH(CH_3)C(O)OCH_3$. In some embodiments is a compound of Formula (Icc), or a pharmaceutically acceptable salt or solvate thereof, wherein $-X-R^1$ is $-N(H)CH(CH_3)C(O)OCH_3$. In some embodiments is a compound of Formula (Icc), or a pharmaceutically acceptable salt or solvate thereof, wherein $-X-R^1$ is $-OCH_2CH_2C(O)OCH_3$. In some embodiments is a compound of Formula (Icc), or a pharmaceutically acceptable salt or solvate thereof, wherein $-X-R^1$ is $-N(H)CH_2CH_2C(O)OCH_3$. In some embodiments is a compound of Formula (Icc), or a pharmaceutically acceptable salt or solvate thereof, wherein $-X-R^1$ is $-OCH_2CH_2CH_2C(O)OCH_3$. In some embodiments is a compound of Formula (Icc), or a pharmaceutically acceptable salt or solvate thereof, wherein $-X-R^1$ is $-N(H)CH_2CH_2CH_2C(O)OCH_3$. In some embodiments is a compound of Formula (Icc), or a pharmaceutically acceptable salt or solvate thereof, wherein $-X-R^1$ is $-OCH_2CH_2C(CH_3)_2C(O)OCH_3$. In some embodiments is a compound of Formula (Icc), or a pharmaceutically acceptable salt or solvate thereof, wherein $-X-R^1$ is $-N(H)CH_2CH_2C(CH_3)_2C(O)OCH_3$.

In some embodiments is a compound of Formula (Icc), or a pharmaceutically acceptable salt or solvate thereof, wherein n is 1 or 2. In some embodiments is a compound of Formula (Icc), or a pharmaceutically acceptable salt or solvate thereof, wherein n is 0 or 1. In some embodiments is a compound of Formula (Icc), or a pharmaceutically acceptable salt or solvate thereof, wherein n is 0. In some embodiments is a compound of Formula (Icc), or a pharmaceutically acceptable salt or solvate thereof, wherein n is 1. In some embodiments is a compound of Formula (Icc), or a pharmaceutically acceptable salt or solvate thereof, wherein n is 2.

In some embodiments is a compound of Formula (Icc), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (Icc), or a pharmaceutically acceptable salt or solvate thereof, wherein n is 1 and $R^2$ is halogen. In some embodiments is a compound of Formula (Icc), or a pharmaceutically acceptable salt or solvate thereof, wherein n is 1 and $R^2$ is $-Cl$. In some embodiments is a compound of Formula (Icc), or a pharmaceutically acceptable salt or solvate thereof, wherein n is 1 and $R^2$ is $-F$. In some embodiments is a compound of Formula (Icc), or a pharmaceutically acceptable salt or solvate thereof, wherein n is 1 and $R^2$ is $C_{1-6}$alkyl. In some embodiments is a compound of Formula (Icc), or a pharmaceutically acceptable salt or solvate thereof, wherein n is 1 and $R^2$ is $-CH_3$. In some embodiments is a compound of Formula (Icc), or a pharmaceutically acceptable salt or solvate thereof, wherein n is 1 and $R^2$ is $C_{1-6}$haloalkyl. In some embodiments is a compound of Formula (Icc), or a pharmaceutically acceptable salt or solvate thereof, wherein n is 1 and $R^2$ is $-CF_3$.

In some embodiments is a compound of Formula (Icc), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (Icc), or a pharmaceutically acceptable salt or solvate thereof, wherein n is 2 and each $R^2$ is independently halogen or $C_{1-6}$haloalkyl. In some embodiments is a compound of Formula (Icc), or a pharmaceutically acceptable salt or solvate thereof, wherein n is 2 and each $R^2$ is independently halogen or $C_{1-6}$alkyl. In some embodiments is a compound of Formula (Icc), or a pharmaceutically acceptable salt or solvate thereof, wherein n is 2 and each $R^2$ is independently halogen. In some embodiments is a compound of Formula (Icc), or a pharmaceutically acceptable salt or solvate thereof, wherein n is 2 and each $R^2$ is independently $C_{1-6}$alkyl. In some embodiments is a compound of Formula (Icc), or a pharmaceutically acceptable salt or solvate thereof, wherein n is 2 and each $R^2$ is independently $C_{1-6}$haloalkyl.

Further embodiments provided herein include combinations of one or more of the particular embodiments set forth above.

In some embodiments, the compound disclosed herein has the structure provided in Table 1.

TABLE 1

| Chemical Synthesis Example | Structure | Name |
| --- | --- | --- |
| 1 | 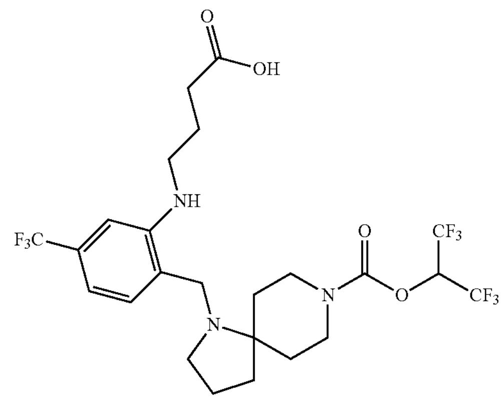 | 4-((2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)butanoic acid |
| 2 | 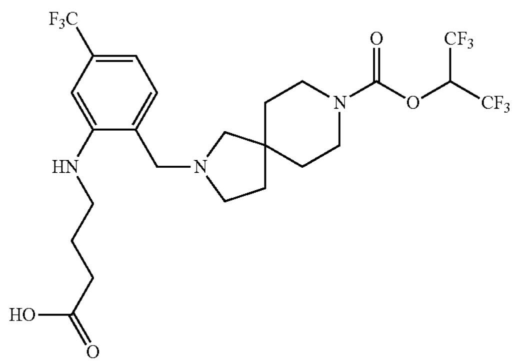 [SMILES: O=C(O)CCCNc1cc(C(F)(F)F)ccc1CN1CCC2(CCN(C(=O)OC(C(F)(F)F)C(F)(F)F)CC2)C1] | 4-((2-((8-(((1,1,1,3,3,3-Hexafluoropropan-2-yl)oxy)carbonyl)-2,8-diazaspiro[4.5]decan-2-yl)methyl)-5-(trifluoromethyl)phenyl)amino)butanoic acid |
| 3 | 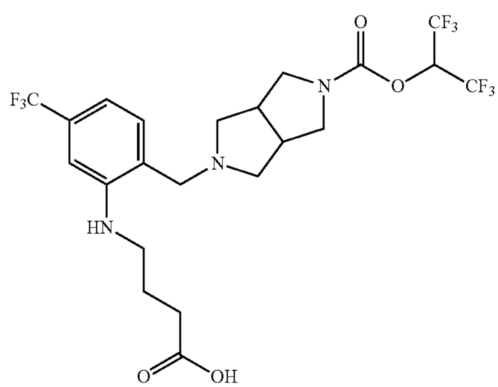 [SMILES: O=C(O)CCCNc1cc(C(F)(F)F)ccc1CN1CC2CN(C(=O)OC(C(F)(F)F)C(F)(F)F)CC2C1] | 4-((2-((5-(((1,1,1,3,3,3-Hexafluoropropan-2-yl)oxy)carbonyl)hexahydropyrrolo[3,4-c]pyrrol-2(1H)-yl)methyl)-5-(trifluoromethyl)phenyl)amino)butanoic acid |
| 4 | 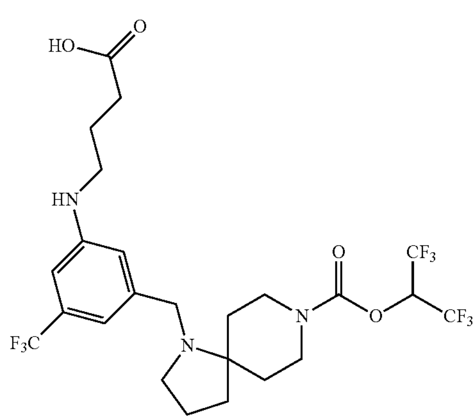 [SMILES: O=C(O)CCCNc1cc(CN2CCCC23CCN(C(=O)OC(C(F)(F)F)C(F)(F)F)CC3)cc(C(F)(F)F)c1] | 4-((3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)butanoic acid |

TABLE 1-continued

| Chemical Synthesis Example | Structure | Name |
|---|---|---|
| 5 | 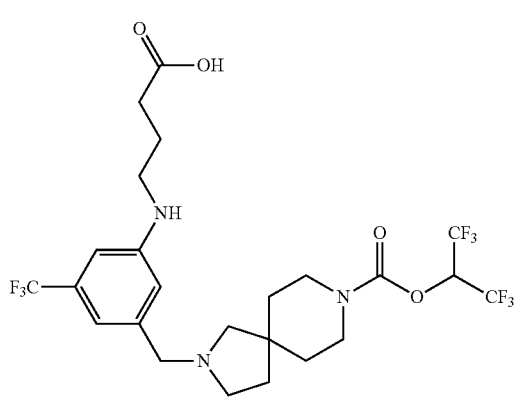 [SMILES: O=C(O)CCCNc1cc(CN2CCC3(CCN(C(=O)OC(C(F)(F)F)C(F)(F)F)CC3)C2)cc(C(F)(F)F)c1] | 4-((3-((8-((((1,1,1,3,3,3-Hexafluoropropan-2-yl)oxy)carbonyl)-2,8-diazaspiro[4.5]decan-2-yl)methyl)-5-(trifluoromethyl)phenyl)amino)butanoic acid |
| 6 | 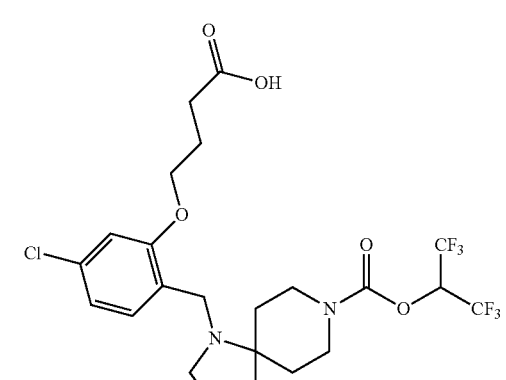 | 4-(5-Chloro-2-((8-((((1,1,1,3,3,3-hexafluoropropan-2-yl)oxy)carbonyl)-1,8-diazaspiro[4.5]decan-1-yl)methyl)phenoxy)butanoic acid |
| 7 | 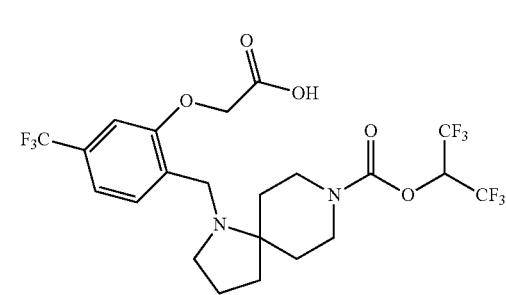 | 2-(2-((8-((((1,1,1,3,3,3-Hexafluoropropan-2-yl)oxy)carbonyl)-1,8-diazaspiro[4.5]decan-1-yl)methyl)-5-(trifluoromethyl)phenoxy)acetic acid |
| 8 | 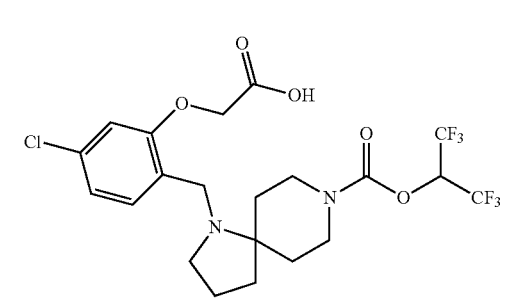 [SMILES: O=C(O)COc1cc(Cl)ccc1CN1CCCC12CCN(C(=O)OC(C(F)(F)F)C(F)(F)F)CC2] | 2-(5-Chloro-2-((8-((((1,1,1,3,3,3-hexafluoropropan-2-yl)oxy)carbonyl)-1,8-diazaspiro[4.5]decan-1-yl)methyl)phenoxy)acetic acid |

TABLE 1-continued

| Chemical Synthesis Example | Structure | Name |
|---|---|---|
| 9 | 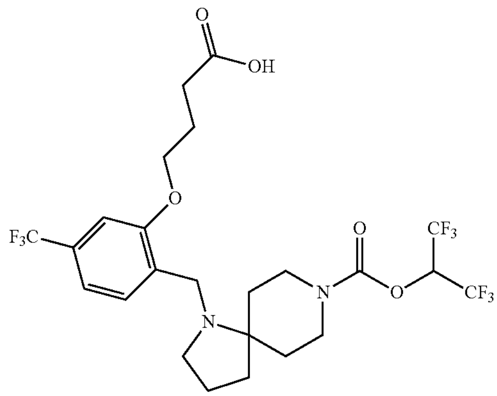 [SMILES: O=C(O)CCCOc1cc(C(F)(F)F)ccc1CN1CCCC12CCN(C(=O)OC(C(F)(F)F)C(F)(F)F)CC2] | 4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)butanoic acid |
| 10 | 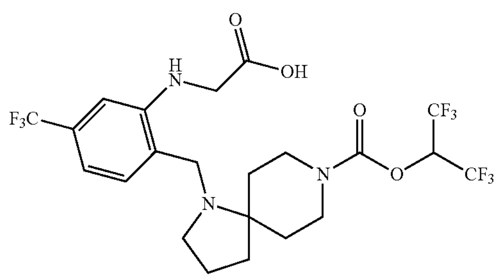 [SMILES: O=C(O)CNc1cc(C(F)(F)F)ccc1CN1CCCC12CCN(C(=O)OC(C(F)(F)F)C(F)(F)F)CC2] | (2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)glycine |
| 11 | 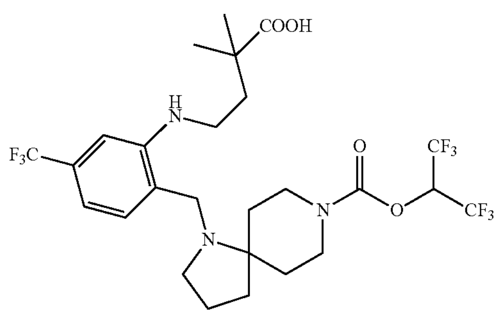 [SMILES: CC(C)(CCNc1cc(C(F)(F)F)ccc1CN1CCCC12CCN(C(=O)OC(C(F)(F)F)C(F)(F)F)CC2)C(=O)O] | 4-((2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)-2,2-dimethylbutanoic acid |
| 12 | 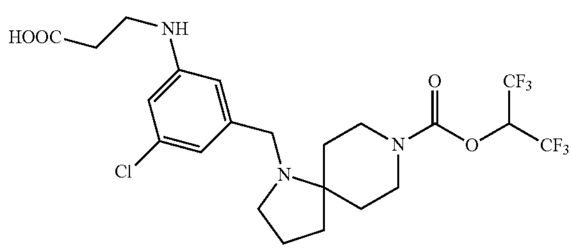 [SMILES: O=C(O)CCNc1cc(Cl)cc(CN2CCCC23CCN(C(=O)OC(C(F)(F)F)C(F)(F)F)CC3)c1] | 3-((3-Chloro-5-((8-(((1,1,1,3,3,3-hexafluoropropan-2-yl)oxy)carbonyl)-1,8-diazaspiro[4.5]decan-1-yl)methyl)phenyl)amino)propanoic acid |
| 13 | 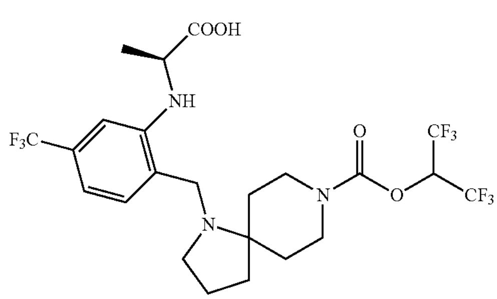 [SMILES: C[C@H](Nc1cc(C(F)(F)F)ccc1CN1CCCC12CCN(C(=O)OC(C(F)(F)F)C(F)(F)F)CC2)C(=O)O] | (2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)-L-alanine |

TABLE 1-continued

| Chemical Synthesis Example | Structure | Name |
|---|---|---|
| 14 | 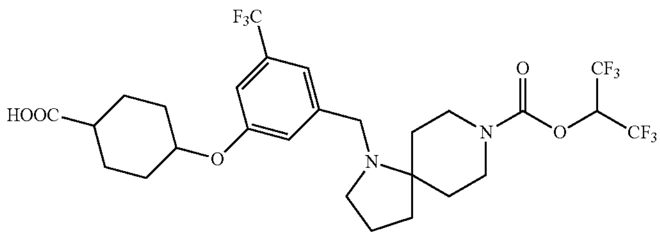 [SMILES: O=C(O)C1CCC(Oc2cc(CN3CCCC34CCN(C(=O)OC(C(F)(F)F)C(F)(F)F)CC4)cc(C(F)(F)F)c2)CC1] | 4-(3-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)cyclohexane-1-carboxylic acid |
| 15 | 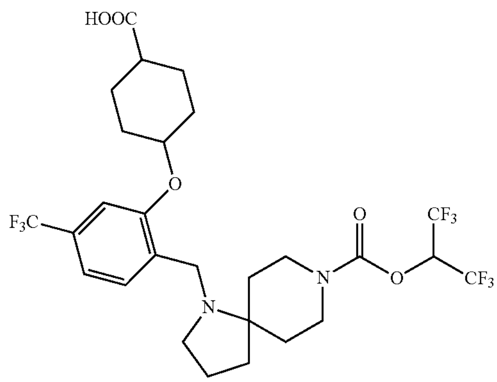 [SMILES: O=C(O)C1CCC(Oc2cc(C(F)(F)F)ccc2CN2CCCC23CCN(C(=O)OC(C(F)(F)F)C(F)(F)F)CC3)CC1] | 4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)cyclohexane-1-carboxylic acid |
| 16 | 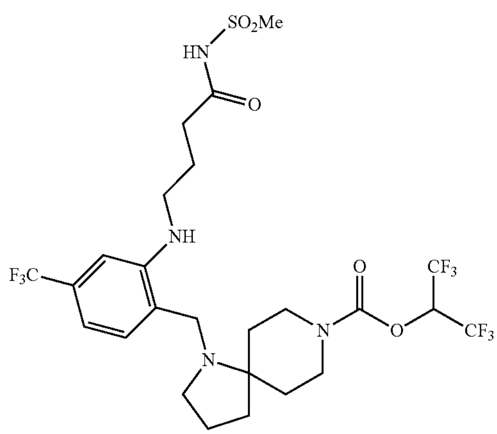 [SMILES: CS(=O)(=O)NC(=O)CCCNc1cc(C(F)(F)F)ccc1CN1CCCC12CCN(C(=O)OC(C(F)(F)F)C(F)(F)F)CC2] | 1,1,1,3,3,3-Hexafluoropropan-2-yl 1-(2-((4-(methylsulfonamido)-4-oxobutyl)amino)-4-(trifluoromethyl)benzyl)-1,8-diazaspiro[4.5]decane-8-carboxylate |
| 17 | 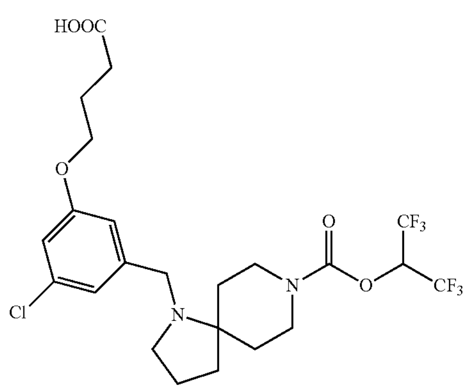 [SMILES: O=C(O)CCCOc1cc(Cl)cc(CN2CCCC23CCN(C(=O)OC(C(F)(F)F)C(F)(F)F)CC3)c1] | 4-(3-Chloro-5-((8-(((1,1,1,3,3,3-hexafluoropropan-2-yl)oxy)carbonyl)-1,8-diazaspiro[4.5]decan-1-yl)methyl)phenoxy)butanoic acid |

TABLE 1-continued

| Chemical Synthesis Example | Structure | Name |
|---|---|---|
| 18 | 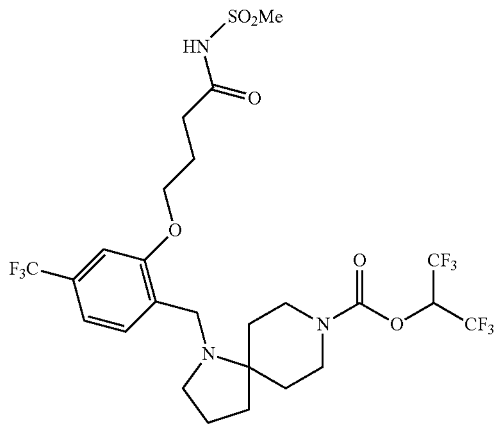 [SMILES: CS(=O)(=O)NC(=O)CCCOc1cc(C(F)(F)F)ccc1CN1CCCC12CCN(C(=O)OC(C(F)(F)F)C(F)(F)F)CC2] | 1,1,1,3,3,3-Hexafluoropropan-2-yl 1-(2-(4-(methylsulfonamido)-4-oxobutoxy)-4-(trifluoromethyl)benzyl)-1,8-diazaspiro[4.5]decane-8-carboxylate |
| 19 | 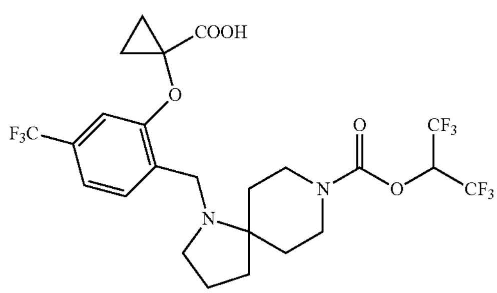 [SMILES: O=C(OC(C(F)(F)F)C(F)(F)F)N1CCC2(CCCN2Cc2ccc(C(F)(F)F)cc2OC2(C(=O)O)CC2)CC1] | 1-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)cyclopropane-1-carboxylic acid |
| 20 | 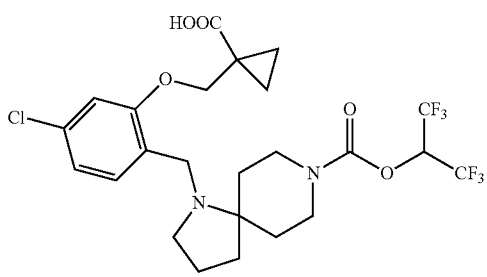 [SMILES: O=C(OC(C(F)(F)F)C(F)(F)F)N1CCC2(CCCN2Cc2ccc(Cl)cc2OCC2(C(=O)O)CC2)CC1] | 1-((5-Chloro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid |
| 21 | 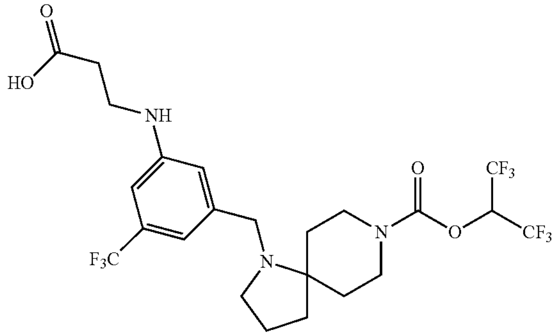 [SMILES: O=C(O)CCNc1cc(CN2CCCC23CCN(C(=O)OC(C(F)(F)F)C(F)(F)F)CC3)cc(C(F)(F)F)c1] | 3-((3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)propanoic acid |

TABLE 1-continued

| Chemical Synthesis Example | Structure | Name |
|---|---|---|
| 22 | 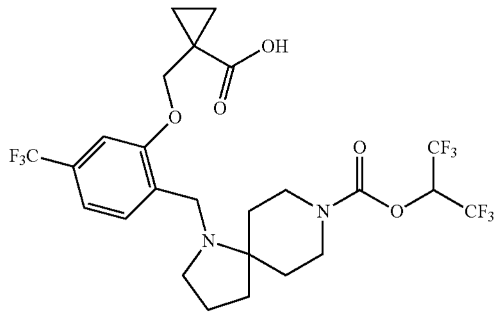 [SMILES: O=C(OC(C(F)(F)F)C(F)(F)F)N1CCC2(CCCN2Cc2ccc(C(F)(F)F)cc2OCC2(C(=O)O)CC2)CC1] | 1-((2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)methyl)cyclopropane-1-carboxylic acid |
| 23 | 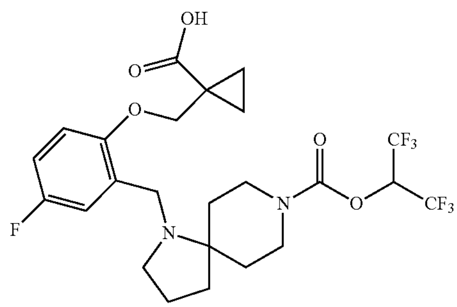 [SMILES: O=C(OC(C(F)(F)F)C(F)(F)F)N1CCC2(CCCN2Cc2cc(F)ccc2OCC2(C(=O)O)CC2)CC1] | 1-((4-Fluoro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid |
| 24 | 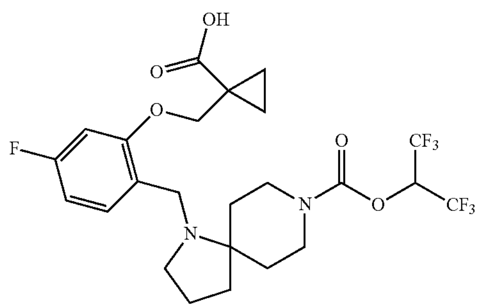 [SMILES: O=C(OC(C(F)(F)F)C(F)(F)F)N1CCC2(CCCN2Cc2ccc(F)cc2OCC2(C(=O)O)CC2)CC1] | 1-((5-Fluoro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid |
| 25 | 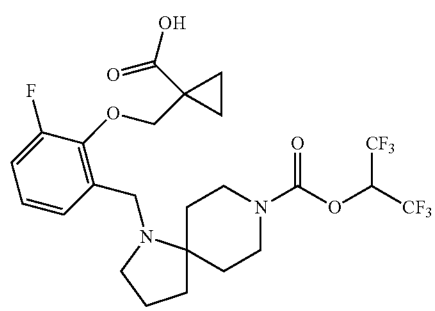 [SMILES: O=C(OC(C(F)(F)F)C(F)(F)F)N1CCC2(CCCN2Cc2cccc(F)c2OCC2(C(=O)O)CC2)CC1] | 1-((2-Fluoro-6-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treat is es that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treat is es that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein
Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate t is sue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

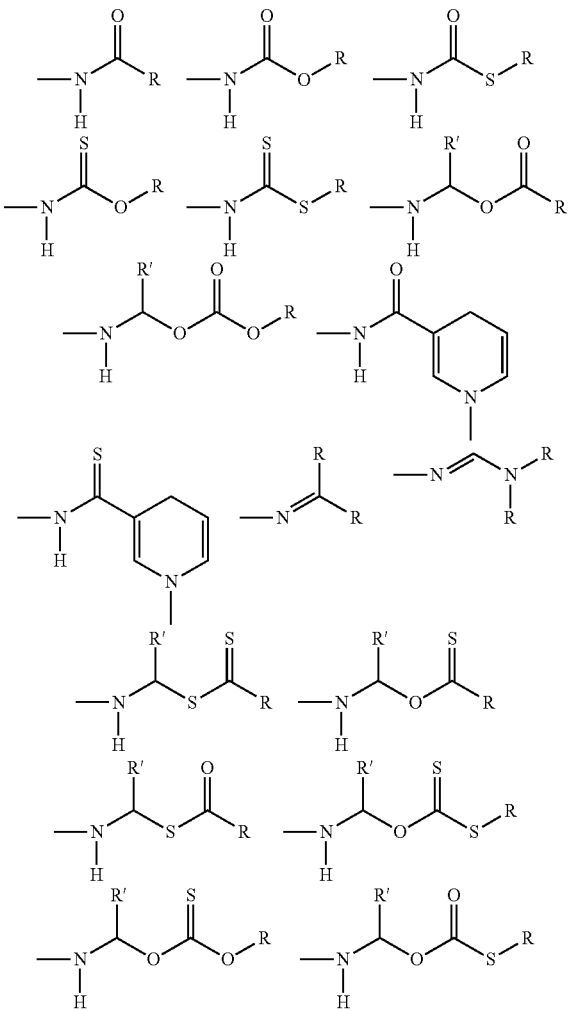

-continued

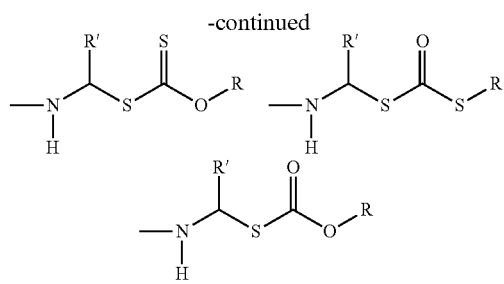

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), (Iaa), (Ib), (Ibb), (Ic), or (Icc) as described herein is administered as a pure chemical. In some embodiments, the compound of Formula (I), (Ia), (Iaa), (Ib), (Ibb), (Ic), or (Icc) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), (Iaa), (Ib), (Ibb), (Ic), or (Icc) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (Ib), or a pharmaceutically acceptable salt thereof.

One embodiment provides a pharmaceutical composition comprising a pharmaceutically acceptable excipient and a compound of Formula (II), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (II), or a pharmaceutically acceptable salt thereof.

In certain embodiments, the compound of Formula (I), (Ia), (Iaa), (Ib), (Ibb), (Ic), or (Icc) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous) vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Iaa), (Ib), (Ibb), (Ic), or (Icc) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (Iaa), (Ib), (Ibb), (Ic), or (Icc), or a pharmaceutically acceptable salt or solvate thereof. The ability of compounds described herein to modulate or inhibit MAGL is evaluated by procedures known in the art and/or described herein. Another aspect of this disclosure provides methods of treating a disease associated with expression or activity of MAGL in a patient.

Also disclosed herein are methods of treating and/or preventing in a patient in need thereof a disorder such as one or more of acute or chronic pain and neuropathy. Disclosed methods include administering a pharmaceutically effective amount of a compound described herein.

In another embodiment is a method of treating pain in a patient, comprising administering a therapeutically effective amount of a compound of Formula (I), (Ia), (Iaa), (Ib), (Ibb), (Ic), or (Icc) described herein, or a pharmaceutically acceptable salt or solvate thereof, to a patient in need thereof to treat said pain. In another embodiment is a method of treating neuropathic pain in a patient, comprising administering a therapeutically effective amount of a compound of Formula (I), (Ia), (Iaa), (Ib), (Ibb), (Ic), or (Icc) described herein, or a pharmaceutically acceptable salt or solvate thereof, to a patient in need thereof to treat said neuropathic pain. In another embodiment is a method of treating inflammatory pain in a patient, comprising administering a therapeutically effective amount of a compound of Formula (I), (Ia), (Iaa), (Ib), (Ibb), (Ic), or (Icc) described herein, or a pharmaceutically acceptable salt or solvate thereof, to a patient in need thereof to treat said inflammatory pain. In another embodiment is a method of treating complex regional pain syndrome in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating a disease or disorder in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof, wherein the disease or disorder is selected from the group consisting of epilepsy/seizure disorder, multiple sclerosis, neuromyelit is optica (NMO), Tourette syndrome, Alzheimer's disease, and abdominal pain associated with irritable bowel syndrome. In another embodiment is a method of treating epilepsy/seizure disorder in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating multiple sclerosis in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating neuromyelit is optica (NMO) in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating Tourette syndrome in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating Alzheimer's disease in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating abdominal pain associated with irritable bowel syndrome in a patient comprising administering to the patient in need thereof a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating acute pain in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating inflammatory pain in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating central pain in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating migraine in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating spasticity or pain associated with multiple sclerosis in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating Persistent Motor Tic Disorder in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In some embodiments, disclosed herein is a method of treating Persistent Vocal Tic Disorder in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating attention deficit and hyperactivity disorder (ADHD) in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In some embodiments, disclosed herein is a method of treating obsessive-compulsive disorder (OCD) in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating atopic dermatit is in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating prurit is in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating Down's syndrome in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating dystonia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating Amyotrophic Lateral Sclerosis (ALS) or ALS-related symptoms in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating agitation in aut is m in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In another embodiment is a method of treating sleep disturbance or bladder dysfunction associated with multiple sclerosis in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating Huntington's Disease in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of Parkinson's Disease in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of improving functional outcome following stroke in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating traumatic brain injury in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In some embodiments, disclosed herein is a method of treating trigeminal neuralgia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof. In some embodiments, disclosed herein is a method of treating glossopharyngeal neuralgia in a patient in need thereof, comprising administering to the patient a therapeutically effective amount of a compound of Formula (I), (Ia), (Iaa), (Ib), (Ibb), (Ic), or (Icc) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (Iaa), (Ib), (Ibb), (Ic), or (Icc).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane t is sues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lomoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($C_1CH_2CH_2C_1$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
LCMS liquid chromatography-mass spectrometry
Me methyl
MeOH methanol
MS mass spectroscopy
NMM N-methylmorpholine
NMR nuclear magnetic resonance
PMB para-methoxybenzyl
rt room temperature
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1

4-((2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)butanoic acid

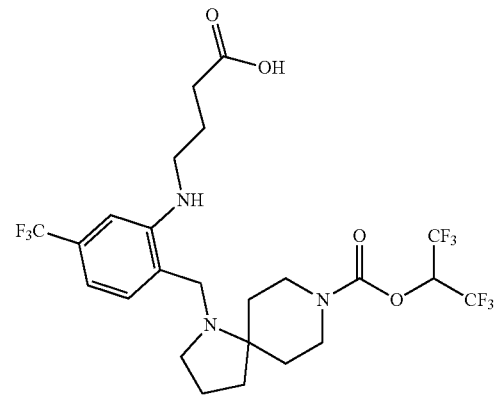 [SMILES: O=C(O)CCCNc1cc(C(F)(F)F)ccc1CN1CCCC12CCN(C(=O)OC(C(F)(F)F)C(F)(F)F)CC2]

Step 1

Preparation of tert-butyl 4-((4-methoxybenzyl)amino)butanoate

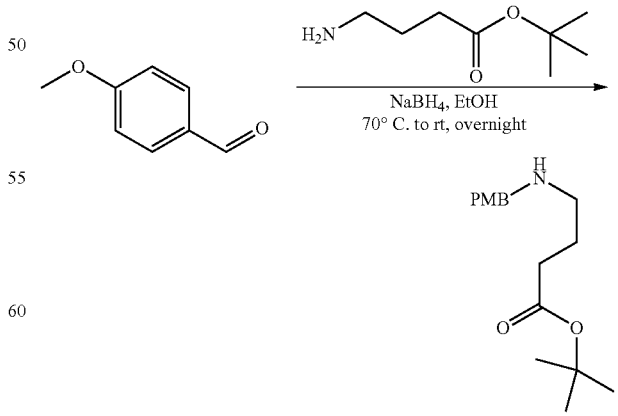

A flask was charged with 4-methoxybenzaldehyde (4.27 g, 31.4 mmol, 1.00 equiv), EtOH (30 mL), and tert-butyl 4-aminobutanoate (5.00 g, 31.4 mmol, 1.00 equiv). The resulting solution was stirred for 5 h at 70° C. and cooled to rt. Sodium borohydride (0.718 g, 18.9 mmol, 0.60 equiv) was added. The resulting solution was stirred overnight at rt and concentrated. The residue was chromatographed on a silica gel column with EtOAc/petroleum ether (2/1) to provide 4.55 g (52% yield) of tert-butyl 4-((4-methoxybenzyl)amino)butanoate as a yellow oil. LCMS (ESI, m/z): 280 [M+H]+.

Step 2

Preparation of tert-butyl 4-((2-formyl-5-(trifluoromethyl)phenyl)(4-methoxybenzyl)amino)butanoate

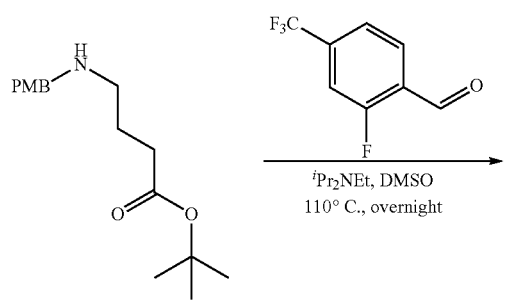

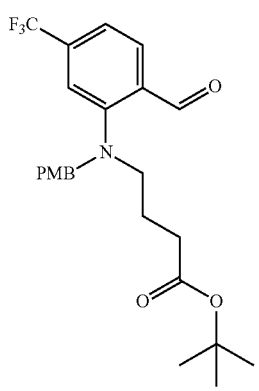

A flask was charged with tert-butyl 4-((4-methoxybenzyl)amino)butanoate (3.00 g, 10.7 mmol, 1.00 equiv), DMSO (35 mL), 2-fluoro-4-(trifluoromethyl)benzaldehyde (2.07 g, 10.7 mmol, 1.00 equiv), and DIPEA (4.18 g, 32.3 mmol, 3.00 equiv) under nitrogen. The resulting solution was stirred overnight at 110° C. and quenched with water (50 mL). The resulting solution was extracted with DCM (2×80 mL) and the organic layers were combined, washed with brine (2×50 mL), dried over anhydrous sodium sulfate, filtered and concentrated. The residue was chromatographed on a silica gel column with EtOAc/petroleum ether (1/12) to provide 2.20 g (45% yield) of tert-butyl 4-((2-formyl-5-(trifluoromethyl)phenyl)(4-methoxybenzyl)amino)butanoate as a yellow oil. LCMS (ESI, m/z): 452 [M+H]+.

Step 3

Preparation of 1-(tert-butyl) 8-(1,1,1,3,3,3-hexafluoropropan-2-yl) 1,8-diazaspiro[4.5]decane-1,8-dicarboxylate

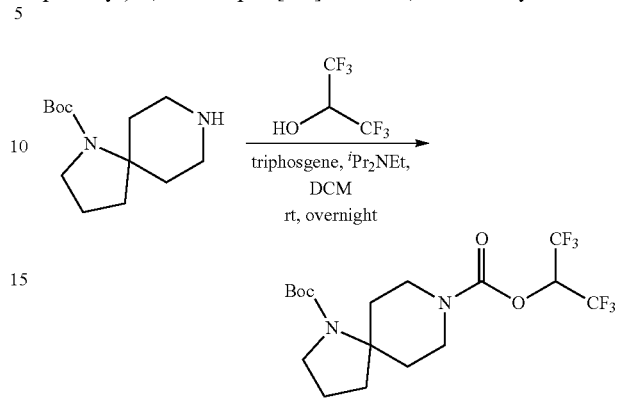

A flask was charged with triphosgene (1.73 g, 5.82 mmol, 0.70 equiv), DCM (60 mL), and HFIP (2.80 g, 16.7 mmol, 2.00 equiv) under nitrogen. DIPEA (4.28 g, 33.2 mmol, 4.00 equiv) was added at 0° C., and then the reaction mixture was allowed to stir for 2 h at rt. tert-Butyl 1,8-diazaspiro[4.5]decane-1-carboxylate (2.00 g, 8.32 mmol, 1.00 equiv) was added and the mixture was stirred overnight. The mixture was then quenched with water (50 mL), extracted with DCM (2×80 mL) and the organic layers were combined, washed with brine (2×50 mL), dried over anhydrous sodium sulfate, filtered and concentrated. The residue was chromatographed on a silica gel column with EtOAc/petroleum ether (⅕) to provide 2.56 g (71% yield) of 1-(tert-butyl) 8-(1,1,1,3,3,3-hexafluoropropan-2-yl) 1,8-diazaspiro[4.5]decane-1,8-dicarboxylate as a yellow solid. LCMS (ESI, m/z): 435 [M+H]+.

Step 4

Preparation of 1,1,1,3,3,3-hexafluoropropan-2-yl 1,8-diazaspiro[4.5]decane-8-carboxylate, 2,2,2-trifluoroacetate salt

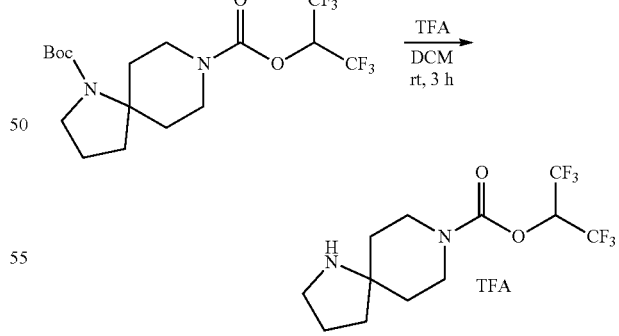

A flask was charged with 1-(tert-butyl) 8-(1,1,1,3,3,3-hexafluoropropan-2-yl) 1,8-diazaspiro[4.5]decane-1,8-dicarboxylate (200 mg, 0.460 mmol, 1.00 equiv), DCM (10 mL), and TFA (2 mL). The resulting solution was stirred for 3 h at rt and concentrated to provide 250 mg (crude) of 1,1,1,3,3,3-hexafluoropropan-2-yl 1,8-diazaspiro[4.5]decane-8-carboxylate, 2,2,2-trifluoroacetate salt as a white solid. LCMS (ESI, m/z): 335 [M+H]+.

Step 5

Preparation of 1,1,1,3,3,3-hexafluoropropan-2-yl 1-(2-((4-(tert-butoxy)-4-oxobutyl)(4-methoxybenzyl)amino)-4-(trifluoromethyl)benzyl)-1,8-diazaspiro[4.5]decane-8-carboxylate

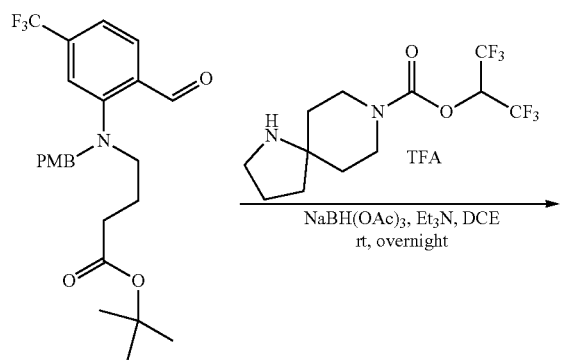

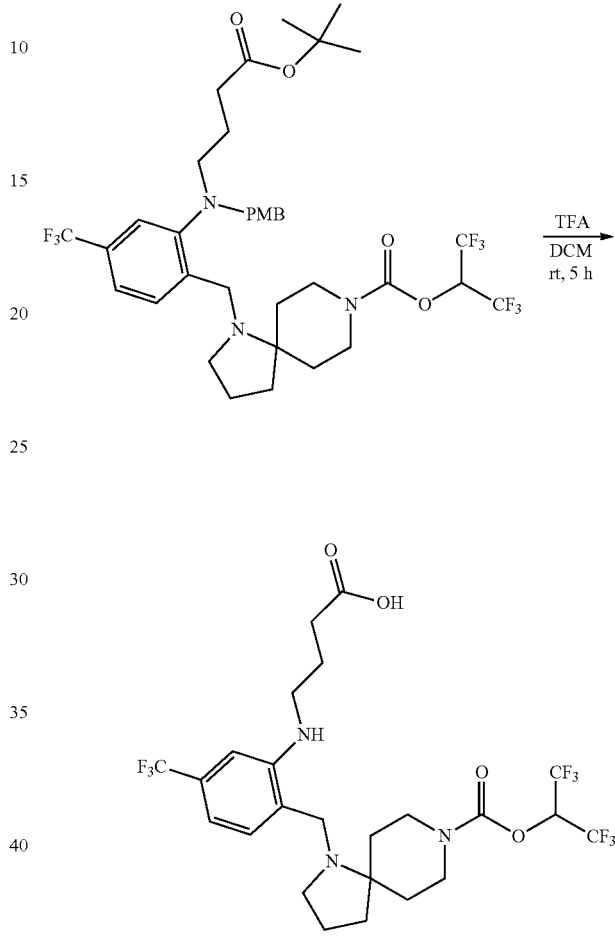

Step 6

Preparation of 4-((2-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)butanoic acid A flask was charged with 1,1,1,3,3,3-hexafluoropropan-2-yl 1,8-diazaspiro[4.5]decane-8-carboxylate, 2,2,2-trifluoroacetate salt (154 mg, 0.460 mmol, 1.20 equiv), DCE (10 mL), TEA (115 mg, 1.14 mmol, 3.00 equiv), and tert-butyl 4-((2-formyl-5-(trifluoromethyl)phenyl)(4-methoxybenzyl)amino)butanoate (171 mg, 0.380 mmol, 1.00 equiv). The resulting solution was stirred 1 h at rt and sodium triacetoxyborohydride (243 mg, 1.15 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 250 mg (86% yield) of 1,1,1,3,3,3-hexafluoropropan-2-yl 1-(2-((4-(tert-butoxy)-4-oxobutyl)(4-methoxybenzyl)amino)-4-(trifluoromethyl)benzyl)-1,8-diazaspiro[4.5]decane-8-carboxylate as a yellow oil. LCMS (ESI, m/z): 770 [M+H]$^+$.

A flask was charged with 1,1,1,3,3,3-hexafluoropropan-2-yl 1-(2-((4-(tert-butoxy)-4-oxobutyl)(4-methoxybenzyl)amino)-4-(trifluoromethyl)benzyl)-1,8-diazaspiro[4.5]decane-8-carboxylate (250 mg, 0.320 mmol, 1.00 equiv), DCM (10 mL), and TFA (2 mL). The resulting solution was stirred 5 h at rt and concentrated. The crude product (400 mg) was purified by preparative HPLC to provide 13.4 mg (7% yield) of 4-((2-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)butanoic acid as a white solid. $^1$H NMR (400 MHz, Methanol-d$_4$) δ 7.15 (d, J=7.6 Hz, 1H), 6.82 (d, J=8.0 Hz, 1H), 6.77 (s, 1H), 6.08-6.16 (m, 1H), 4.15-4.21 (m, 2H), 3.71-3.79 (m, 2H), 3.01-3.19 (m, 4H), 2.64 (t, J=6.8 Hz, 2H), 2.43 (t, J=7.2 Hz, 2H), 1.84-1.97 (m, 8H), 1.48-1.57 (m, 2H). LCMS (ESI, m/z): 594 [M+H]$^+$.

Example 2

4-((2-((8-(((1,1,1,3,3,3-Hexafluoropropan-2-yl)oxy)carbonyl)-2,8-diazaspiro[4.5]decan-2-yl)methyl)-5-(trifluoromethyl)phenyl)amino)butanoic acid

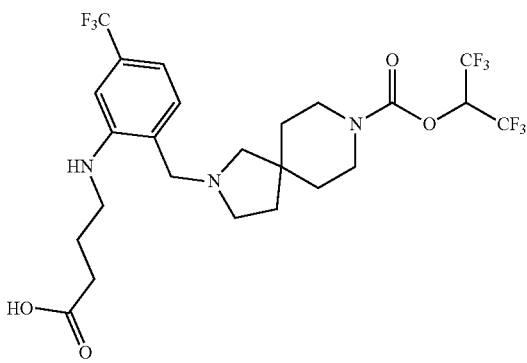 [SMILES: O=C(O)CCCNc1cc(C(F)(F)F)ccc1CN1CCC2(CCN(C(=O)OC(C(F)(F)F)C(F)(F)F)CC2)C1]

The title compound was synthesized according to the representative procedure of Example 1 using commercially available 2-fluoro-4-(trifluoromethyl)benzaldehyde in Step 2 and tert-butyl 2,8-diazaspiro[4.5]decane-2-carboxylate in Step 3 to provide 4-((2-((8-(((1,1,1,3,3,3-hexafluoropropan-2-yl)oxy)carbonyl)-2,8-diazaspiro[4.5]decan-2-yl)methyl)-5-(trifluoromethyl)phenyl)amino)butanoic acid as a white solid. $^1$H NMR (300 MHz, Methanol-$d_4$) 7.24 (d, J=7.5 Hz, 1H), 6.84-6.87 (m, 2H), 6.09-6.18 (m, 1H), 3.86 (s, 2H), 3.47-3.63 (m, 4H), 3.27 (t, J=6.3 Hz, 2H), 2.88 (t, J=7.2 Hz, 2H), 2.74 (s, 2H), 2.40 (t, J=6.9 Hz, 2H), 1.95-2.04 (m, 2H), 1.86 (t, J=7.0 Hz, 2H), 1.66-1.67 (m, 4H). LCMS (ESI, m/z): 594 [M+H]$^+$.

Example 3

4-((2-((5-(((1,1,1,3,3,3-Hexafluoropropan-2-yl)oxy)carbonyl)hexahydropyrrolo[3,4-c]pyrrol-2(1H)-yl)methyl)-5-(trifluoromethyl)phenyl)amino)butanoic acid

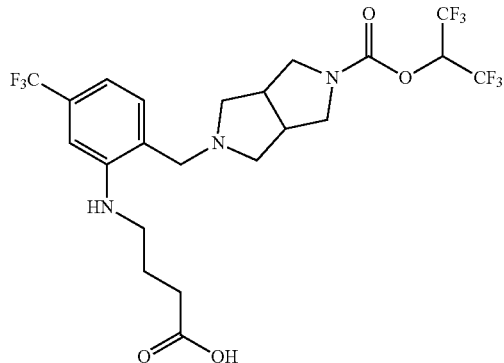 [SMILES: O=C(O)CCCNc1cc(C(F)(F)F)ccc1CN1CC2CN(C(=O)OC(C(F)(F)F)C(F)(F)F)CC2C1]

The title compound was synthesized according to the representative procedure of Example 1 using commercially available tert-butyl hexahydropyrrolo[3,4-c]pyrrole-2(1H)-carboxylate in Step 3 and hydrochloric acid and 1,4-dioxane in Step 6 to provide 60.1 mg (32% yield) of 4-((2-((5-(((1,1,1,3,3,3-hexafluoropropan-2-yl)oxy)carbonyl)hexahydropyrrolo[3,4-c]pyrrol-2(1H)-yl)methyl)-5-(trifluoromethyl)phenyl)amino)butanoic acid as a white solid. $^1$H NMR (300 MHz, Methanol-$d_4$) δ 7.15 (d, J=7.8 Hz, 1H), 6.80-6.83 (m, 2H), 6.08-6.16 (m, 1H), 3.66-3.74 (m, 4H), 3.34-3.42 (m, 2H), 3.18 (t, J=6.9 Hz, 2H), 2.98 (br, 2H), 2.65-2.67 (m, 2H), 2.43-2.50 (m, 2H), 2.33 (t, J=7.2 Hz, 2H), 1.90-1.97 (m, 2H). LCMS (ESI, m/z): 566 [M+H]$^+$.

Example 4

4-((3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)butanoic acid

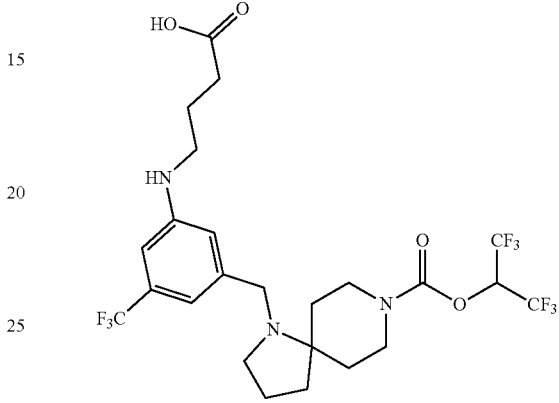

Step 1

Preparation of tert-butyl 4-((3-formyl-5-(trifluoromethyl)phenyl)(4-methoxybenzyl)amino)butanoate

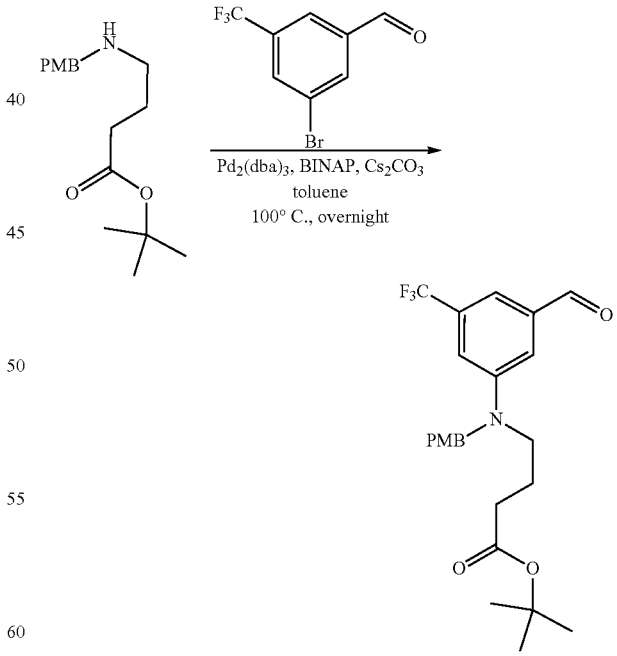

A flask was charged with 3-bromo-5-(trifluoromethyl)benzaldehyde (374 mg, 1.48 mmol, 1.00 equiv), tert-butyl 4-((4-methoxybenzyl)amino)butanoate (500 mg, 1.79 mmol, 1.20 equiv, prepared as described in Example 1, Step 1), tris(dibenzylideneacetone)dipalladium (68.0 mg, 0.070 mmol, 0.05 equiv), 2,2'-bis(diphenylphosphino)-1,1'-binaphthyl (139 mg, 0.220 mmol, 0.15 equiv), cesium carbonate (1.46 g, 4.48 mmol, 3.00 equiv), and toluene (10 mL). The reaction mixture was stirred overnight at 100° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (⅙) to provide 320 mg (48% yield) of tert-butyl 4-((3-formyl-5-(trifluoromethyl)phenyl)(4-methoxybenzyl)amino)butanoate as a yellow oil. LCMS (ESI, m/z): 452 [M+H]⁺.

Step 2

Preparation of 1,1,1,3,3,3-hexafluoropropan-2-yl 1-(3-((4-(tert-butoxy)-4-oxobutyl)(4-methoxybenzyl)amino)-5-(trifluoromethyl)benzyl)-1,8-diazaspiro[4.5]decane-8-carboxylate

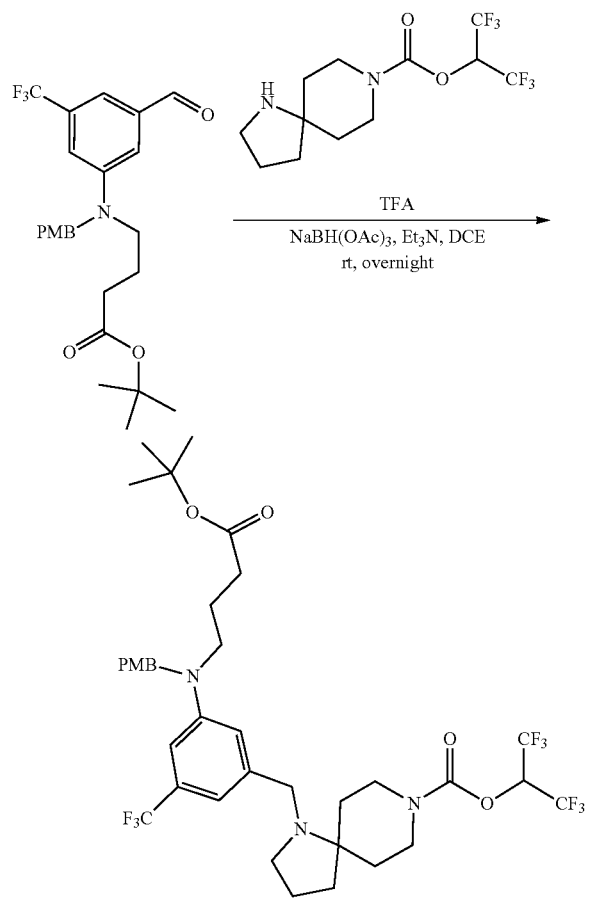

A flask was charged with tert-buty 4-((3-formyl-5-(trifluoromethyl)phenyl)(4-methoxybenzyl)amino)butanoate (300 mg, 0.660 mmol, 1.00 equiv), DCE (10 mL), TEA (200 mg, 1.98 mmol, 3.00 equiv), and 1,1,1,3,3,3-hexafluoropropan-2-yl 1,8-diazaspiro[4.5]decane-8-carboxylate, 2,2,2-trifluoroacetate salt (267 mg, 0.800 mmol, 1.20 equiv, prepared as described in Example 1, Steps 3-4). The mixture was stirred for 1 h at rt and then sodium triacetoxyborohydride (420 mg, 1.98 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (⅙) to provide 320 mg (63% yield) of 1,1,1,3,3,3-hexafluoropropan-2-yl 1-(3-((4-(tert-butoxy)-4-oxobutyl)(4-methoxybenzyl)amino)-5-(trifluoromethyl)benzyl)-1,8-diazaspiro[4.5]decane-8-carboxylate as a yellow oil. LCMS (ESI, m/z): 770 [M+H]⁺.

Step 3

Preparation of 4-((3-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)butanoic acid

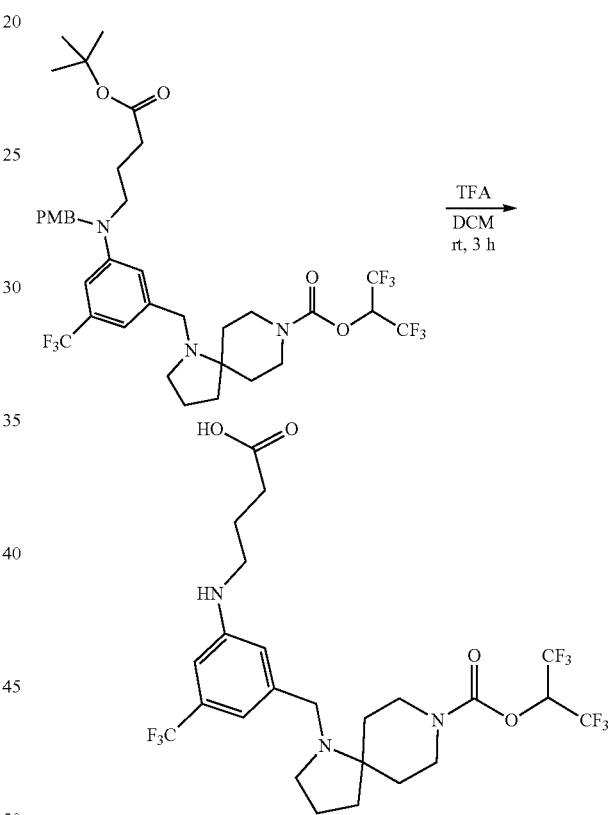

A flask was charged with 1,1,1,3,3,3-hexafluoropropan-2-yl 1-(3-((4-(tert-butoxy)-4-oxobutyl)(4-methoxybenzyl)amino)-5-(trifluoromethyl)benzyl)-1,8-diazaspiro[4.5]decane-8-carboxylate (320 mg, 0.420 mmol, 1.00 equiv), DCM (10 mL), and TFA (10 mL). The resulting solution was stirred for 3 h at rt and concentrated. The crude product was purified by preparative HPLC to provide 23.8 mg (10% yield) of 4-((3-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)butanoic acid as a white solid. ¹H NMR (300 MHz, Methanol-$d_4$) δ 6.84 (s, 2H), 6.76 (s, 1H), 6.12-6.18 (m, 1H), 4.22 (br, 2H), 3.78 (s, 2H), 3.06-3.12 (m, 4H), 2.93 (t, J=6.0 Hz, 2H), 2.35 (t, J=6.0 Hz, 2H), 2.00-2.05 (m, 2H), 1.84-1.93 (m, 6H), 1.64-1.68 (m, 2H). LCMS (ESI, m/z): 594 [M+H]⁺.

Example 5

4-((3-((8-(((1,1,1,3,3,3-Hexafluoropropan-2-yl)oxy)carbonyl)-2,8-diazaspiro[4.5]decan-2-yl)methyl)-5-(trifluoromethyl)phenyl)amino)butanoic acid

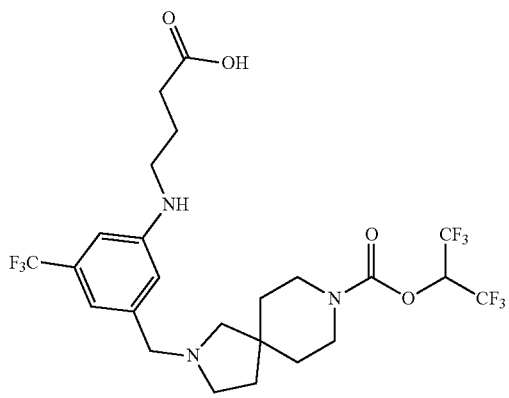 [SMILES: O=C(O)CCCNc1cc(CN2CCC3(CCN(C(=O)OC(C(F)(F)F)C(F)(F)F)CC3)C2)cc(C(F)(F)F)c1]

The title compound was prepared according to the representative procedure of Example 4 using 1,1,1,3,3,3-hexafluoropropan-2-yl 2,8-diazaspiro[4.5]decane-8-carboxylate (prepared as described in Example 1, Steps 3-4 using commercially available tert-butyl 2,8-diazaspiro[4.5]decane-2-carboxylate) in Step 2 to provide 4-((3-((8-(((1,1,1,3,3,3-hexafluoropropan-2-yl)oxy)carbonyl)-2,8-diazaspiro[4.5]decan-2-yl)methyl)-5-(trifluoromethyl)phenyl) amino)butanoic acid as a white solid. $^1$H NMR (300 MHz, Methanol-$d_4$) δ 6.83-6.90 (m, 3H), 6.08-6.16 (m, 1H), 4.00 (br, 2H), 3.43-3.63 (m, 4H), 3.12-3.20 (m, 4H), 2.96 (br, 2H), 2.32 (t, J=7.0 Hz, 2H), 1.84-1.94 (m, 4H), 1.66-1.68 (m, 4H). LCMS (ESI, m/z): 594 [M+H]$^+$.

Example 6

4-(5-Chloro-2-((8-(((1,1,1,3,3,3-hexafluoropropan-2-yl)oxy)carbonyl)-1,8-diazaspiro[4.5]decan-1-yl)methyl)phenoxy)butanoic acid

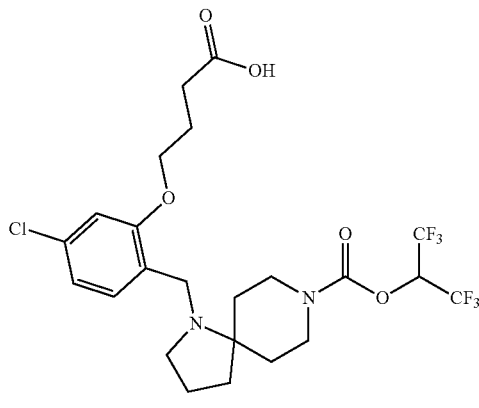 [SMILES: O=C(O)CCCOc1cc(Cl)ccc1CN1CCCC12CCN(C(=O)OC(C(F)(F)F)C(F)(F)F)CC2]

Step 1

Preparation of tert-butyl 4-(5-chloro-2-formylphenoxy)butanoate

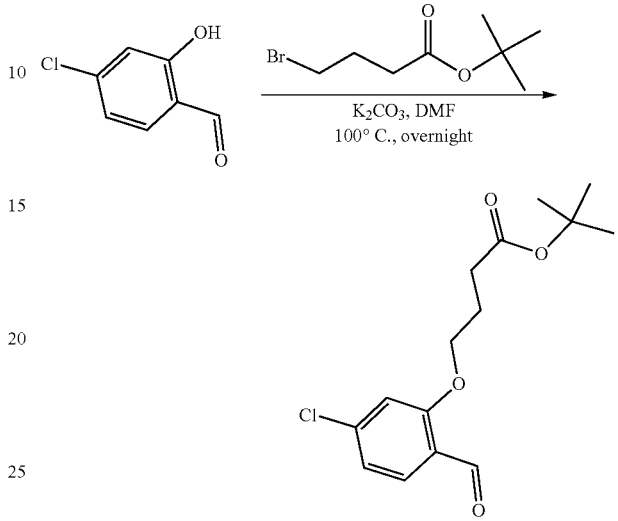

A flask was charged with 4-chloro-2-hydroxybenzaldehyde (250 mg, 1.60 mmol, 1.00 equiv), DMF (10 mL), tert-butyl 4-bromobutanoate (710 mg, 3.20 mmol, 2.00 equiv), and potassium carbonate (662 mg, 4.80 mmol, 3.00 equiv). The resulting solution was stirred overnight at 100° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (⅛) to provide 400 mg (84% yield) of tert-butyl 4-(5-chloro-2-formylphenoxy)butanoate as a light yellow oil. $^1$H NMR (300 MHz, Chloroform-d) δ 10.4 (s, 1H), 7.79 (d, J=8.0 Hz, 1H), 7.00-7.04 (m, 2H), 4.14 (t, J=6.0 Hz, 2H), 2.46-2.48 (m, 2H), 2.15-2.20 (m, 2H), 1.47 (s, 9H).

Step 2

Preparation of 1,1,1,3,3,3-hexafluoropropan-2-yl 1-(2-(4-(tert-butoxy)-4-oxobutoxy)-4-chlorobenzyl)-1,8-diazaspiro[4.5]decane-8-carboxylate

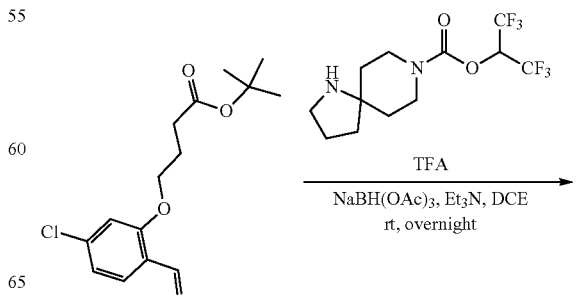

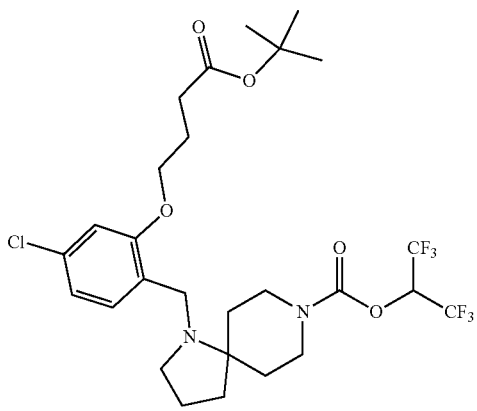

A flask was charged with 1,1,1,3,3,3-hexafluoropropan-2-yl 1,8-diazaspiro[4.5]decane-8-carboxylate, 2,2,2-trifluoroacetate salt (224 mg, 0.670 mmol, 1.00 equiv, prepared as described in Example 1, Steps 3-4), DCE (10 mL), TEA (203 mg, 2.01 mmol, 3.00 equiv), tert-butyl 4-(5-chloro-2-formylphenoxy)butanoate (200 mg, 0.670 mmol, 1.00 equiv). The mixture was stirred for 1 h at rt and sodium triacetoxyborohydride (426 mg, 2.01 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (95/5) to provide 350 mg (85% yield) of 1,1,1,3,3,3-hexafluoropropan-2-yl 1-(2-(4-(tert-butoxy)-4-oxobutoxy)-4-chlorobenzyl)-1,8-diazaspiro[4.5]decane-8-carboxylate as a yellow oil. LCMS (ESI, m/z): 617 [M+H]$^+$.

Step 3

Preparation of 4-(5-chloro-2-((8-(((1,1,1,3,3,3-hexafluoropropan-2-yl)oxy)carbonyl)-1,8-diazaspiro[4.5]decan-1-yl)methyl)phenoxy)butanoic acid

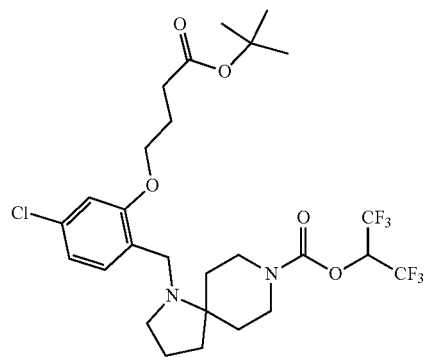

$\xrightarrow{\text{HCl}}$ 1,4-dioxane rt, overnight

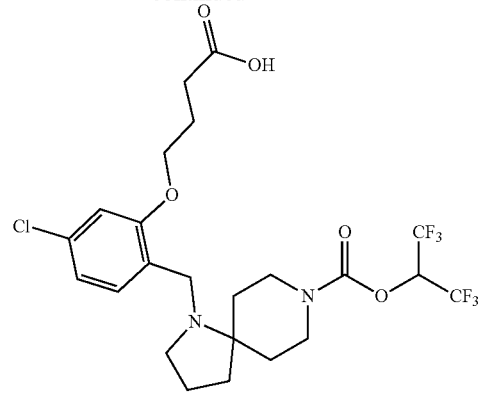

A flask was charged with 1,1,1,3,3,3-hexafluoropropan-2-yl 1-(2-(4-(tert-butoxy)-4-oxobutoxy)-4-chlorobenzyl)-1,8-diazaspiro[4.5]decane-8-carboxylate (300 mg, 0.490 mmol, 1.00 equiv), 1,4-dioxane (10 mL), and hydrochloric acid (3 mL). The resulting solution was stirred overnight at rt and concentrated. The crude product (300 mg) was purified by preparative HPLC to provide 123.0 mg (45% yield) of 4-(5-chloro-2-((8-(((1,1,1,3,3,3-hexafluoropropan-2-yl)oxy)carbonyl)-1,8-diazaspiro[4.5]decan-1-yl)methyl)phenoxy)butanoic acid as a white solid. $^1$H NMR (300 MHz, Methanol-d$_4$) δ 7.33 (d, J=8.1 Hz, 1H), 7.08 (s, 1H), 6.95-6.98 (m, 1H), 6.12-6.21 (m, 1H), 4.21-4.29 (m, 2H), 4.12 (t, J=6.0 Hz, 2H), 4.04 (s, 2H), 3.05-3.22 (m, 4H), 2.38 (t, J=6.8 Hz, 2H), 2.01-2.21 (m, 8H), 1.79-1.89 (m, 2H). LCMS (ESI, m/z): 561 [M+H]$^+$.

Example 7

2-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)acetic acid

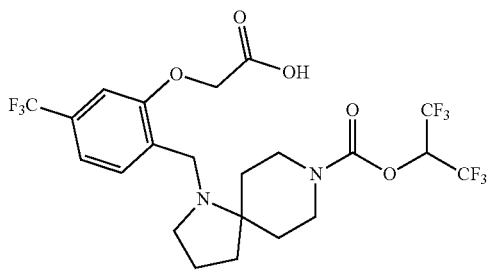 [SMILES: O=C(O)COc1cc(C(F)(F)F)ccc1CN1CCCC12CCN(C(=O)OC(C(F)(F)F)C(F)(F)F)CC2]

Step 1

Preparation of 2-hydroxy-4-(trifluoromethyl)benzaldehyde

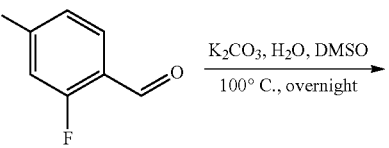

$\xrightarrow{\text{K}_2\text{CO}_3, \text{H}_2\text{O}, \text{DMSO}}{100° \text{C., overnight}}$

107

-continued

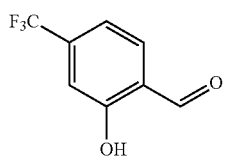

A flask was charged with 2-fluoro-4-(trifluoromethyl) benzaldehyde (1.00 g, 5.21 mmol, 1.00 equiv), water (2 mL), DMSO (10 mL), and potassium carbonate (2.16 g, 15.6 mmol, 3.00 equiv) under nitrogen. The resulting solution was stirred overnight at 100° C. and quenched with water (50 mL). The resulting solution was extracted with EtOAc (2×80 mL) and the organic layers were combined, washed with brine (2×50 mL), dried over anhydrous sodium sulfate, filtered and concentrated. The residue was chromatographed on a silica gel column with EtOAc/petroleum ether (1/19) to provide 500 mg (51% yield) of 2-hydroxy-4-(trifluoromethyl)benzaldehyde as a light yellow oil.

Step 2

Preparation of tert-butyl 1-(2-hydroxy-4-(trifluoromethyl)benzyl)-1,8-diazaspiro[4.5]decane-8-carboxylate

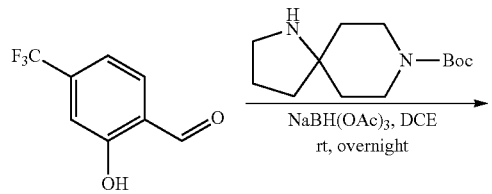

A flask was charged with 2-hydroxy-4-(trifluoromethyl)benzaldehyde (150 mg, 0.790 mmol, 1.00 equiv), DCE (10 mL), and tert-butyl 1,8-diazaspiro[4.5]decane-8-carboxylate (227 mg, 0.940 mmol, 1.20 equiv). The mixture was stirred for 1 h at rt and sodium triacetoxyborohydride (502 mg, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 180 mg (55% yield) of tert-butyl 1-(2-hydroxy-4-(trifluoromethyl)benzyl)-1,8-diazaspiro[4.5]decane-8-carboxylate as a colorless oil. LCMS (ESI, m/z): 415 [M+H]+.

108

Step 3

Preparation of tert-butyl 1-(2-(2-(tert-butoxy)-2-oxoethoxy)-4-(trifluoromethyl)benzyl)-1,8-diazaspiro[4.5]decane-8-carboxylate

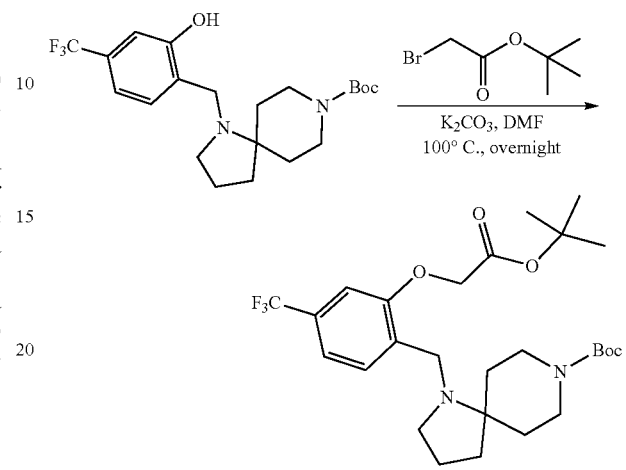

A flask was charged with tert-butyl 1-(2-hydroxy-4-(trifluoromethyl)benzyl)-1,8-diazaspiro[4.5]decane-8-carboxylate (180 mg, 0.430 mmol, 1.00 equiv), DMF (10 mL), tert-butyl 2-bromoacetate (90.0 mg, 0.460 mmol, 1.10 equiv), and potassium carbonate (174 mg, 1.26 mmol, 3.00 equiv). The resulting solution was stirred overnight at 100° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with DCM/MeOH (96/4) to provide 160 mg (70% yield) of tert-butyl 1-(2-(2-(tert-butoxy)-2-oxoethoxy)-4-(trifluoromethyl)benzyl)-1,8-diazaspiro[4.5]decane-8-carboxylate as a yellow oil. LCMS (ESI, m/z): 529 [M+H]+.

Step 4

Preparation of 2-(2-((1,8-diazaspiro[4.5]decan-1-yl)methyl)-5-(trifluoromethyl)phenoxy)acetic acid hydrochloride

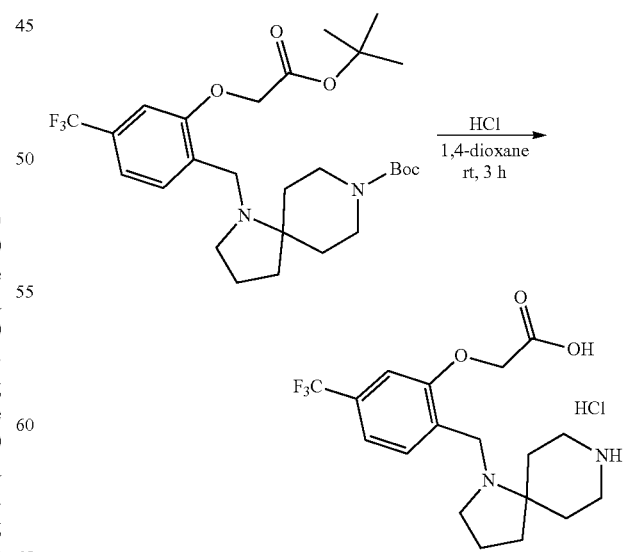

A flask was charged with tert-butyl 1-(2-(2-(tert-butoxy)-2-oxoethoxy)-4-(trifluoromethyl)benzyl)-1,8-diazaspiro

[4.5]decane-8-carboxylate (160 mg, 0.300 mmol, 1.00 equiv), 1,4-dioxane (10 mL), and concentrated hydrochloric acid (2 mL). The resulting solution was stirred for 3 h at rt and concentrated to provide 170 mg (crude) of 2-(2-((1,8-diazaspiro[4.5]decan-1-yl)methyl)-5-(trifluoromethyl)phenoxy)acetic acid hydrochloride as a yellow oil. LCMS (ESI, m/z): 373 [M+H]+.

Step 5

Preparation of 2-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)acetic acid

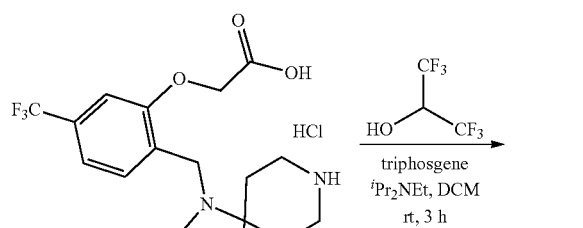

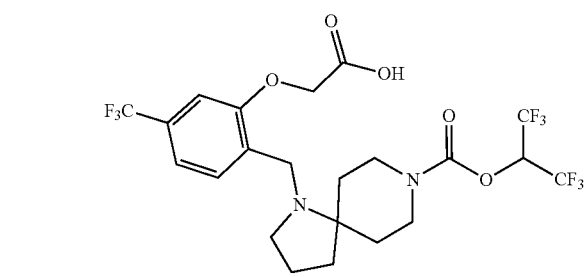

A flask was charged with triphosgene (45.0 mg, 0.152 mmol, 0.50 equiv), DCM (10 mL), and HFIP (77.0 mg, 0.456 mmol, 1.50 equiv) under nitrogen. DIPEA (117 mg, 0.910 mmol, 3.00 equiv) was added at 0° C. The mixture was stirred for 1 h at rt and 2-(2-((1,8-diazaspiro[4.5]decan-1-yl)methyl)-5-(trifluoromethyl)phenoxy)acetic acid hydrochloride (113 mg, 0.304 mmol, 1.00 equiv) was added. The resulting solution was stirred for 3 h at rt and quenched with water (30 mL). The resulting solution was extracted with DCM (2×50 mL) and the organic layers were combined, washed with brine (2×30 mL), dried over anhydrous sodium sulfate, filtered and concentrated. The crude product (130 mg) was purified by preparative HPLC to provide 44.6 mg (33% yield) of 2-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)acetic acid as a white solid. $^1$H NMR (300 MHz, Methanol-d$_4$) δ 7.59 (d, J=7.8 Hz, 1H), 7.48 (s, 1H), 7.35 (d, J=7.8 Hz, 1H), 6.14-6.25 (m, 1H), 4.99 (s, 1H), 4.80 (br, 3H), 4.26-4.34 (m, 2H), 3.07-3.27 (m, 4H), 2.10 (br, 6H), 1.89-1.93 (m, 2H). LCMS (ESI, m/z): 567 [M+H]+.

Example 8

2-(5-Chloro-2-((8-(((1,1,1,3,3,3-hexafluoropropan-2-yl)oxy)carbonyl)-1,8-diazaspiro[4.5]decan-1-yl)methyl)phenoxy)acetic acid

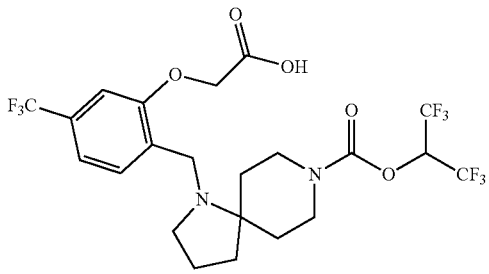 [SMILES: O=C(O)COc1cc(C(F)(F)F)ccc1CN1CCCC12CCN(C(=O)OC(C(F)(F)F)C(F)(F)F)CC2]

The title compound was prepared according to the representative procedure of Example 7 using 4-chloro-2-hydroxybenzaldehyde in Step 2 to provide 2-(5-chloro-2-((8-(((1,1,1,3,3,3-hexafluoropropan-2-yl)oxy)carbonyl)-1,8-diazaspiro[4.5]decan-1-yl)methyl)phenoxy)acetic acid as a white solid. $^1$H NMR (300 MHz, Methanol-d$_4$) δ 7.38 (d, J=8.1 Hz, 1H), 7.26 (s, 1H), 7.06-7.09 (m, 1H), 6.13-6.21 (m, 1H), 4.65-4.77 (m, 4H), 4.25-4.33 (m, 2H), 3.15-3.30 (m, 4H), 2.11-2.51 (m, 6H), 1.88-1.92 (m, 2H). LCMS (ESI, m/z): 533 [M+H]+.

Example 9

4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)butanoic acid

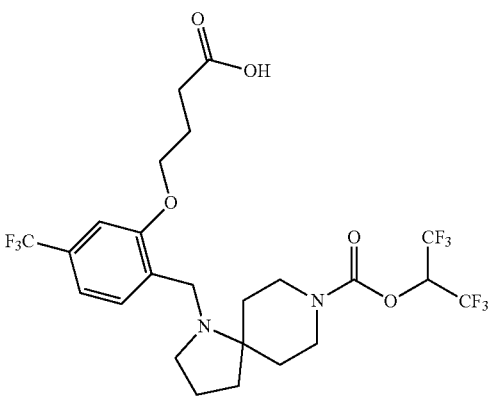 [SMILES: O=C(O)CCCOc1cc(C(F)(F)F)ccc1CN1CCCC12CCN(C(=O)OC(C(F)(F)F)C(F)(F)F)CC2]

Step 1

Preparation of tert-butyl 4-(2-formyl-5-(trifluoromethyl)phenoxy)butanoate

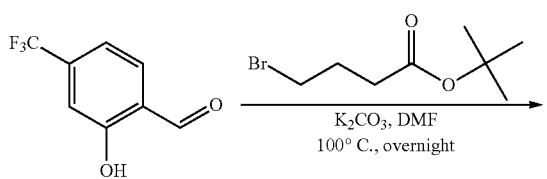

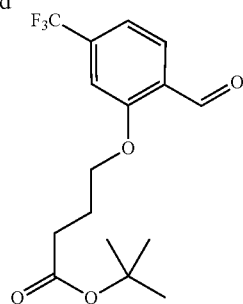

A flask was charged with 2-hydroxy-4-(trifluoromethyl)benzaldehyde (110 mg, 0.580 mmol, 1.00 equiv, prepared as described in Example 7, Step 1), DMF (10 mL), tert-butyl 4-bromobutanoate (258 mg, 1.16 mmol, 2.00 equiv), and potassium carbonate (240 mg, 1.74 mmol, 3.00 equiv). The resulting solution was stirred overnight at rt and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (1/5) to provide 120 mg (62% yield) of tert-butyl 4-(2-formyl-5-(trifluoromethyl)phenoxy)butanoate as a yellow oil.

Step 2

Preparation of 1,1,1,3,3,3-hexafluoropropan-2-yl 1-(2-(4-(tert-butoxy)-4-oxobutoxy)-4-(trifluoromethyl)benzyl)-1,8-diazaspiro[4.5]decane-8-carboxylate

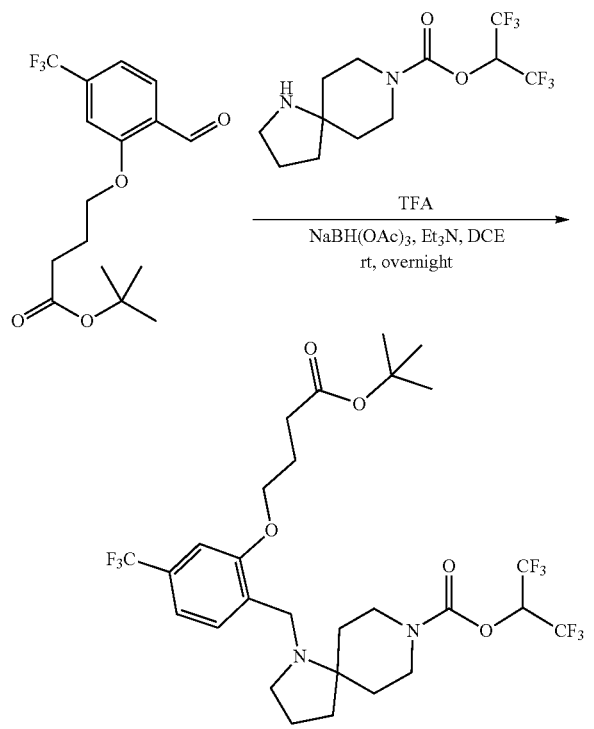

A flask was charged with tert-butyl 4-(2-formyl-5-(trifluoromethyl)phenoxy)butanoate (200 mg, 0.600 mmol, 1.00 equiv), DCE (10 mL), TEA (182 mg, 1.80 mmol, 3.00 equiv), and 1,1,1,3,3,3-hexafluoropropan-2-yl 1,8-diazaspiro[4.5]decane-8-carboxylate, 2,2,2-trifluoroacetate salt (201 mg, 0.600 mmol, 1.00 equiv, prepared as described in Example 1, Steps 3-4). The mixture was stirred for 1 h at rt and then sodium triacetoxyborohydride (382 mg, 1.80 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (3/17) to provide 250 mg (64% yield) of 1,1,1,3,3,3-hexafluoropropan-2-yl 1-(2-(4-(tert-butoxy)-4-oxobutoxy)-4-(trifluoromethyl)benzyl)-1,8-diazaspiro[4.5]decane-8-carboxylate as a colorless oil. LCMS (ESI, m/z): 651 [M+H]$^+$.

Step 3

Preparation of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)butanoic acid

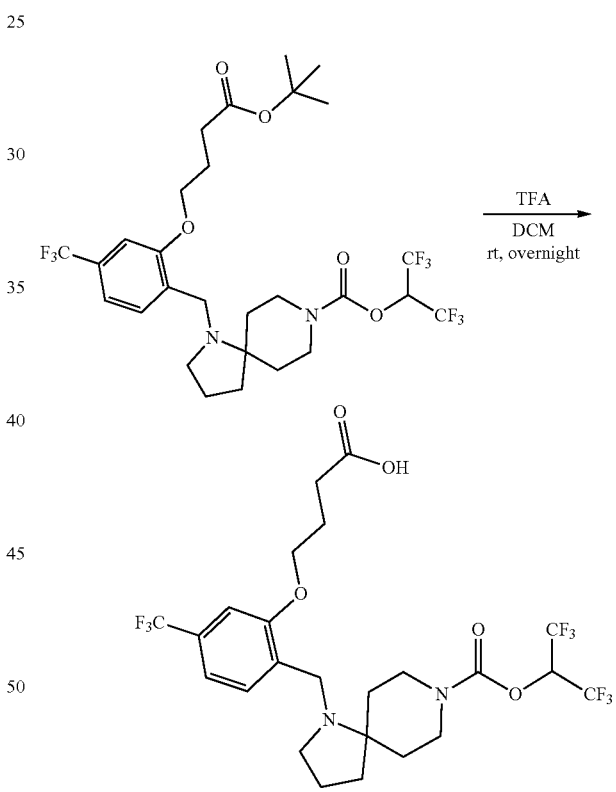

A flask was charged with 1,1,1,3,3,3-hexafluoropropan-2-yl 1-(2-(4-(tert-butoxy)-4-oxobutoxy)-4-(trifluoromethyl)benzyl)-1,8-diazaspiro[4.5]decane-8-carboxylate (250 mg, 0.380 mmol, 1.00 equiv), DCM (10 mL), and TFA (2 mL). The resulting solution was stirred overnight at rt and concentrated. The crude product (300 mg) was purified by preparative HPLC to provide 93.6 mg (41% yield) of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)butanoic acid as a white solid. $^1$H NMR (300 MHz, Methanol-d$_4$) δ 7.53-7.56 (m, 1H), 7.24-7.26 (m, 2H), 6.09-6.22 (m, 1H), 4.11-4.34 (m, 4H), 4.02 (br, 2H), 3.04-

3.31 (m, 4H), 2.42 (t, J=6.9 Hz, 2H), 2.12-2.18 (m, 4H), 1.92-2.10 (m, 4H), 1.75-1.87 (m, 2H). LCMS (ESI, m/z): 595 [M+H]+.

Example 10

(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)glycine

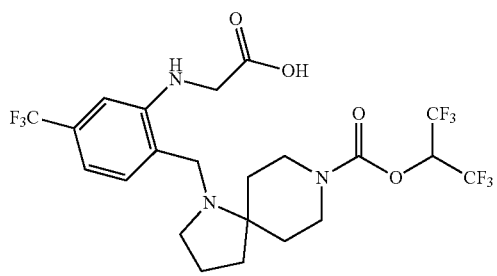 [SMILES: O=C(O)CNc1cc(C(F)(F)F)ccc1CN1CCCC12CCN(C(=O)OC(C(F)(F)F)C(F)(F)F)CC2]

Step 1

Preparation of tert-butyl 1-(2-nitro-4-(trifluoromethyl)benzyl)-1,8-diazaspiro[4.5]decane-8-carboxylate

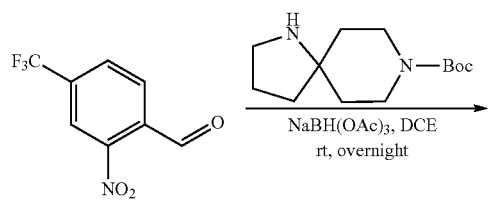

A flask was charged with 2-nitro-4-(trifluoromethyl)benzaldehyde (500 mg, 2.28 mmol, 1.00 equiv), DCE (15 mL), and tert-butyl 1,8-diazaspiro[4.5]decane-8-carboxylate (547 mg, 2.28 mmol, 1.00 equiv). The mixture was stirred for 1 h at rt and sodium triacetoxyborohydride (1450 mg, 6.84 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 400 mg (40% yield) of tert-butyl 1-(2-nitro-4-(trifluoromethyl)benzyl)-1,8-diazaspiro[4.5]decane-8-carboxylate as a yellow oil. LCMS (ESI, m/z): 444 [M+H]+.

Step 2

Preparation of tert-butyl 1-(2-amino-4-(trifluoromethyl)benzyl)-1,8-diazaspiro[4.5]decane-8-carboxylate

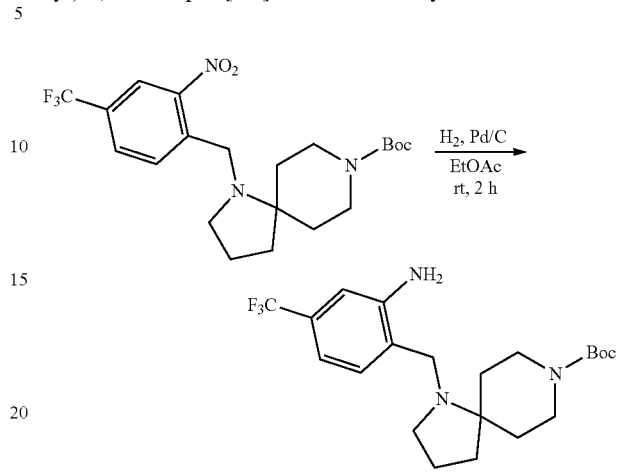

A flask was charged with tert-butyl 1-(2-nitro-4-(trifluoromethyl)benzyl)-1,8-diazaspiro[4.5]decane-8-carboxylate (400 mg, 0.900 mmol, 1.00 equiv), EtOAc (10 mL), and 10% palladium on carbon (200 mg). Hydrogen was introduced into the reaction mixture and it was allowed to stir for 2 h at rt. The solids were filtered, and the filtrate was concentrated to provide 300 mg (80% yield) of tert-butyl 1-(2-amino-4-(trifluoromethyl)benzyl)-1,8-diazaspiro[4.5]decane-8-carboxylate as a yellow solid. LCMS (ESI, m/z): 414 [M+H]+.

Step 3

Preparation of tert-butyl 1-(2-((2-(tert-butoxy)-2-oxoethyl)amino)-4-(trifluoromethyl)benzyl)-1,8-diazaspiro[4.5]decane-8-carboxylate

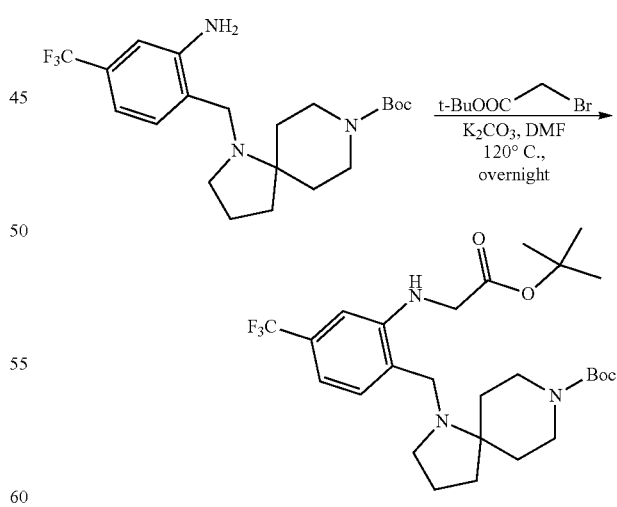

A flask was charged with tert-butyl 1-(2-amino-4-(trifluoromethyl)benzyl)-1,8-diazaspiro[4.5]decane-8-carboxylate (150 mg, 0.360 mmol, 1.00 equiv), DMF (10 mL), potassium carbonate (150 mg, 1.09 mmol, 3.00 equiv), and tert-butyl 2-bromoacetate (77.0 mg, 0.390 mmol, 1.10 equiv). The resulting solution was stirred overnight at 100°

C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (98/2) to provide 100 mg (52% yield) of tert-butyl 1-(2-((2-(tert-butoxy)-2-oxoethyl)amino)-4-(trifluoromethyl)benzyl)-1,8-diazaspiro[4.5]decane-8-carboxylate as a yellow oil. LCMS (ESI, m/z): 528 [M+H]$^+$.

Step 4

Preparation of (2-((1,8-diazaspiro[4.5]decan-1-yl)methyl)-5-(trifluoromethyl)phenyl)glycine hydochloride

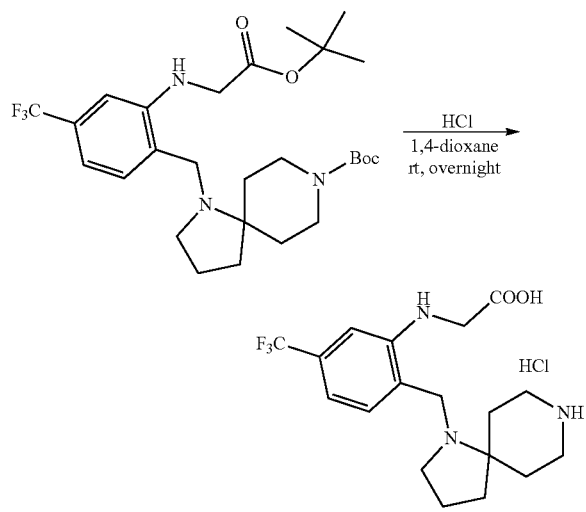

A flask was charged with tert-butyl 1-(2-((2-(tert-butoxy)-2-oxoethyl)amino)-4-(trifluoromethyl)benzyl)-1,8-diazaspiro[4.5]decane-8-carboxylate (100 mg, 0.234 mmol, 1.00 equiv), 1,4-dioxane (10 mL), and hydrochloric acid (3 mL). The resulting solution was stirred overnight at rt and concentrated to provide 150 mg (crude) of (2-((1,8-diazaspiro[4.5]decan-1-yl)methyl)-5-(trifluoromethyl)phenyl)glycine hydrochloride as a yellow solid. LCMS (ESI, m/z): 372 [M+H]$^+$.

Step 5

Preparation of (2-((8-(((1,1,1,3,3,3-hexafluoropropan-2-yl)oxy)carbonyl)-1,8-diazaspiro[4.5]decan-1-yl)methyl)-5-(trifluoromethyl)phenyl)glycine

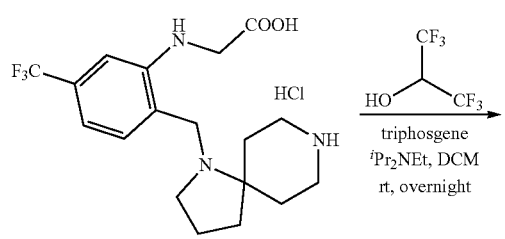

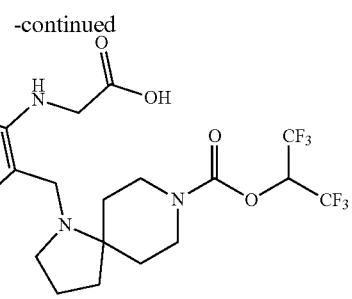

A flask was charged with triphosgene (45.0 mg, 0.150 mmol, 0.70 equiv), DCM (10 mL), and HFIP (73.0 mg, 0.430 mmol, 2.00 equiv) under nitrogen. DIPEA (84.0 mg, 0.650 mmol, 3.00 equiv) was added at 0° C. and the mixture was stirred for 1 h at rt. (2-((1,8-Diazaspiro[4.5]decan-1-yl)methyl)-5-(trifluoromethyl)phenyl)glycine hydrochloride (80.0 mg, 0.220 mmol, 1.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The crude product (300 mg) was purified by preparative HPLC to provide 21.9 mg (18% yield) of (2-((8-(((1,1,1,3,3,3-hexafluoropropan-2-yl)oxy)carbonyl)-1,8-diazaspiro[4.5]decan-1-yl)methyl)-5-(trifluoromethyl)phenyl)glycine as a white solid. $^1$H NMR (300 MHz, Methanol-d$_4$) δ 7.30 (d, J=7.5 Hz, 1H), 6.94 (d, J=8.4 Hz, 1H), 6.88 (br, 1H), 6.09-6.19 (m, 1H), 4.20-4.28 (m, 2H), 4.05 (s, 2H), 3.84 (s, 2H), 3.04-3.23 (m, 2H), 2.87-2.90 (m, 2H), 2.09-2.12 (m, 2H), 1.92-2.03 (m, 4H), 1.78-1.82 (m, 2H). LCMS (ESI, m/z): 566 [M+H]$^+$.

Example 11

4-((2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)amino)-2,2-dimethylbutanoic acid

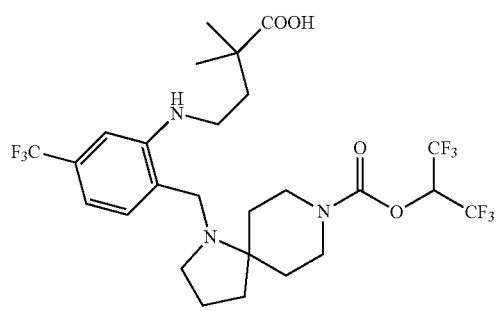 [SMILES: CC(C)(CCNc1cc(C(F)(F)F)ccc1CN1CCCC12CCN(C(=O)OC(C(F)(F)F)C(F)(F)F)CC2)C(=O)O]

Step 1

Preparation of tert-butyl 1-(2-bromo-4-(trifluoromethyl)benzyl)-1,8-diazaspiro[4.5]decane-8-carboxylate

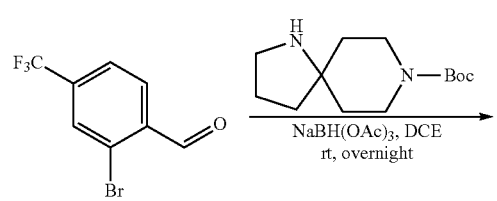

-continued

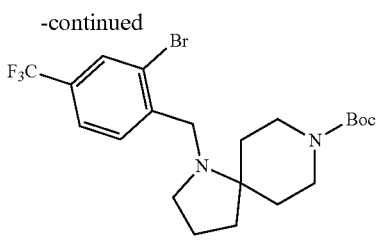

A 250-mL round-bottom flask was charged with 2-bromo-4-(trifluoromethyl)benzaldehyde (2.00 g, 7.90 mmol, 1.00 equiv), DCE (30 mL), and tert-butyl 1,8-diazaspiro[4.5]decane-8-carboxylate (2.28 g, 9.48 mmol, 1.20 equiv). The mixture was stirred for 1 h at room temperature before the addition of sodium triacetoxyborohydride (5.04 g, 23.7 mmol, 3.00 equiv). The resulting solution was stirred overnight at room temperature and quenched with water (50 mL). The mixture was extracted with DCM (2×80 mL) and the organic layers were combined, washed with brine (2×80 mL), dried over anhydrous sodium sulfate, filtered and concentrated under reduced pressure. The residue was chromatographed on a silica gel column with DCM/MeOH (97/3) to provide (58% yield) of tert-butyl 1-(2-bromo-4-(trifluoromethyl)benzyl)-1,8-diazaspiro[4.5]decane-8-carboxylate as a light yellow oil. LCMS (ESI, m/z): 477 [M+H]+.

Step 2

Preparation of tert-butyl 1-(2-((4-(tert-butoxy)-3,3-dimethyl-4-oxobutyl)amino)-4-(trifluoromethyl)benzyl)-1,8-diazaspiro[4.5]decane-8-carboxylate

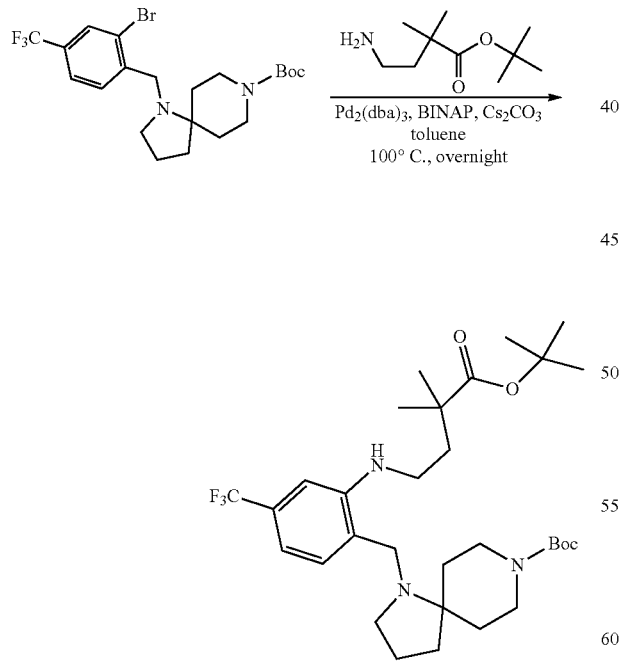

A 50-mL round-bottom flask was charged with tert-butyl 1-(2-bromo-4-(trifluoromethyl)benzyl)-1,8-diazaspiro[4.5]decane-8-carboxylate (400 mg, 0.840 mmol, 1.00 equiv), toluene (10 mL), tris(dibenzylideneacetone)dipalladium (115 mg, 0.130 mmol, 0.15 equiv), 2,2'-bis(diphenylphosphino)-1,1'-binaphthyl (235 mg, 0.390 mmol, 0.45 equiv), cesium carbonate (822 mg, 2.52 mmol, 3.00 equiv), and tert-butyl 4-amino-2,2-dimethylbutanoate (189 mg, 1.01 mmol, 1.20 equiv) under nitrogen. The resulting solution was stirred overnight at 100° C. and quenched with water (30 mL). The mixture was extracted with DCM (2×50 mL) and the organic layers were combined, washed with brine (2×30 mL), dried over anhydrous sodium sulfate, filtered and concentrated under reduced pressure. The residue was chromatographed on a silica gel column with EtOAc/hexane (1/5) to provide 300 mg (61% yield) of tert-butyl 1-(2-((4-(tert-butoxy)-3,3-dimethyl-4-oxobutyl)amino)-4-(trifluoromethyl)benzyl)-1,8-diazaspiro[4.5]decane-8-carboxylate as a yellow oil. LCMS (ESI, m/z): 584 [M+H]+.

Step 3

Preparation of 4-((2-((1,8-diazaspiro[4.5]decan-1-yl)methyl)-5-(trifluoromethyl)phenyl)amino)-2,2-dimethylbutanoic acid hydrochloride

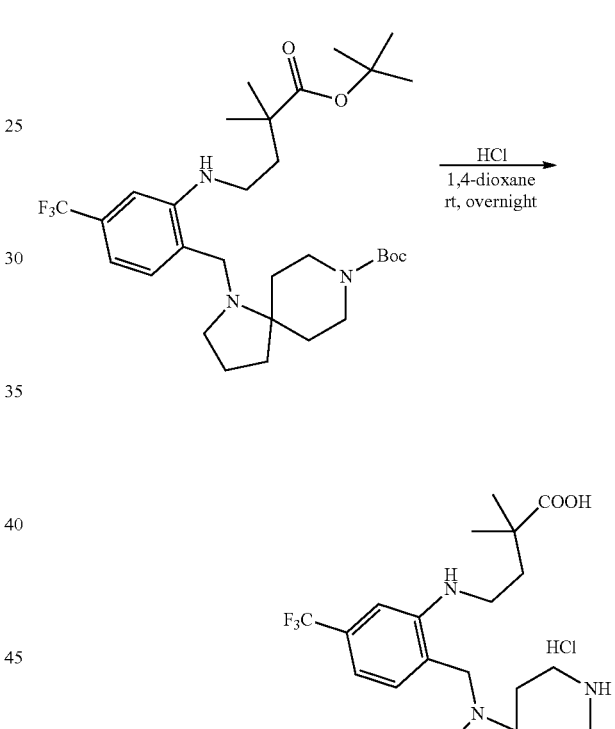

A 50-mL round-bottom flask was charged with tert-butyl 1-(2-((4-(tert-butoxy)-3,3-dimethyl-4-oxobutyl)amino)-4-(trifluoromethyl)benzyl)-1,8-diazaspiro[4.5]decane-8-carboxylate (300 mg, 0.510 mmol, 1.00 equiv), 1,4-dioxane (10 mL), and concentrated hydrochloric acid (3 mL). The resulting solution was stirred overnight at room temperature and concentrated under reduced pressure to provide 400 mg (crude) of 4-[(2-[1,8-diazaspiro[4.5]decan-1-ylmethyl]-5-(trifluoromethyl)phenyl)amino]-2,2-dimethylbutanoic acid hydrochloride as a light yellow solid. LCMS (ESI, m/z): 428 [M+H]+.

Step 4

Preparation of 4-((2-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)-2,2-dimethylbutanoic acid

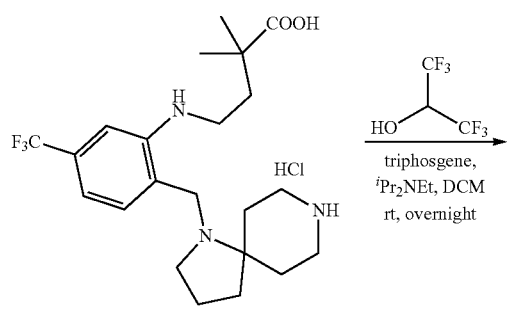

A 50-mL round-bottom flask was charged with triphosgene (97.0 mg, 0.330 mmol, 0.70 equiv), DCM (10 mL), and 1,1,1,3,3,3-hexafluoropropan-2-ol (157 mg, 0.930 mmol, 2.00 equiv) under nitrogen. N,N-Diisopropylethylamine (181 mg, 1.40 mmol, 3.00 equiv) was added at 0° C., and the mixture was stirred for 1 h at room temperature. 4-[(2-[1,8-Diazaspiro[4.5]decan-1-ylmethyl]-5-(trifluoromethyl)phenyl)amino]-2,2-dimethylbutanoic acid hydrochloride (200 mg, 0.470 mmol, 1.00 equiv) was then added and the resulting solution was stirred overnight at room temperature before quenching with water (30 mL). The mixture was extracted with DCM (2×50 mL) and the organic layers were combined, washed with brine (2×30 mL), dried over anhydrous sodium sulfate, filtered and concentrated under reduced pressure. The crude product (300 mg) was purified by preparative HPLC to afford 51.7 mg (18% yield) of 4-((2-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)-2,2-dimethylbutanoic acid as a white solid. $^1$H NMR (300 MHz, Methanol-$d_4$) δ 7.15 (d, J=7.8 Hz, 1H), 6.77-6.82 (m, 2H), 6.08-6.16 (m, 1H), 4.17 (br, 2H), 3.73 (s, 2H), 3.00-3.16 (m, 4H), 2.63 (t, J=6.9 Hz, 2H), 1.76-1.97 (m, 8H), 1.51-1.55 (m, 2H), 1.25 (s, 6H). LCMS (ESI, m/z): 622 [M+H]$^+$.

Example 12

3-((3-Chloro-5-((8-(((1,1,1,3,3,3-hexafluoropropan-2-yl)oxy)carbonyl)-1,8-diazaspiro[4.5]decan-1-yl)methyl)phenyl)amino)propanoic acid

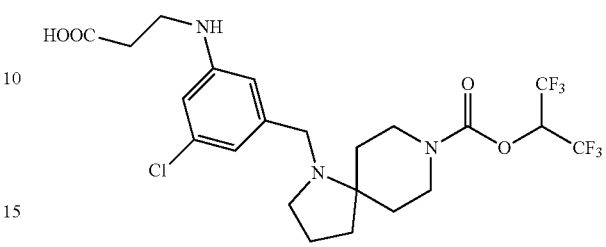

The title compound was prepared according to the representative procedure of Example 11 using 2-bromo-4-(trifluoromethyl)benzaldehyde in Step 1 and tert-butyl 4-amino-2,2-dimethylbutanoate in Step 2 to provide 3-((3-chloro-5-((8-(((1,1,1,3,3,3-hexafluoropropan-2-yl)oxy)carbonyl)-1,8-diazaspiro[4.5]decan-1-yl)methyl)phenyl)amino) propanoic acid as a white solid. $^1$H NMR (300 MHz, Methanol-$d_4$) δ 6.87 (br, 2H), 6.79 (br, 1H), 6.08-6.21 (m, 1H), 4.20-4.22 (m, 2H), 3.81 (s, 2H), 3.40 (t, J=6.9 Hz, 2H), 3.02-3.19 (m, 2H), 2.94-2.98 (m, 2H), 2.52 (t, J=6.8 Hz, 2H), 1.88-2.06 (m, 6H), 1.56-1.72 (m, 2H). LCMS (ESI, m/z): 546 [M+H]$^+$.

Example 13

(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)-L-alanine

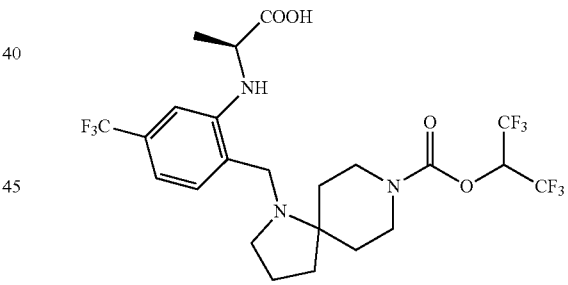

Step 1

Synthesis of (2-((8-(tert-butoxycarbonyl)-1,8-diazaspiro[4.5]decan-1-yl)methyl)-5-(trifluoromethyl)phenyl)-L-alanine

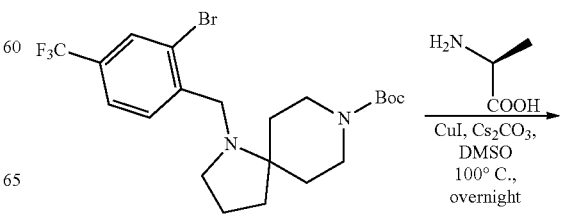

121
-continued

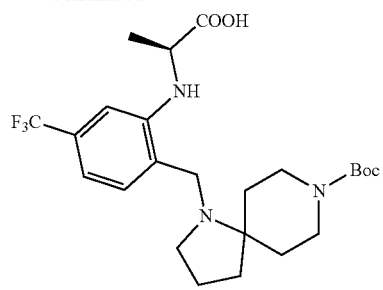

A 50-mL round-bottom flask was charged with tert-butyl 1-(2-bromo-4-(trifluoromethyl)benzyl)-1,8-diazaspiro[4.5]decane-8-carboxylate (Example 11, Step 1, 300 mg, 0.630 mmol, 1.00 equiv), DMSO (10 mL), (2S)-2-aminopropanoic acid (168 mg, 1.89 mmol, 3.00 equiv), cesium carbonate (821 mg, 2.52 mmol, 4.00 equiv), and copper (I) iodide (48.0 mg, 0.250 mmol, 0.40 equiv) under nitrogen. The resulting solution was stirred overnight at 100° C. and quenched with water (1 mL). The residue was chromatographed on a silica gel column with DCM/MeOH (4/1) to provide 200 mg (66% yield) of (2-((8-(tert-butoxycarbonyl)-1,8-diazaspiro[4.5]decan-1-yl)methyl)-5-(trifluoromethyl)phenyl)-L-alanine as a light yellow solid. LCMS (ESI, m/z): 486 [M+H]+.

Step 2

Preparation of (2-((8-(tert-butoxycarbonyl)-1,8-diazaspiro[4.5]decan-1-yl)methyl)-5-(trifluoromethyl)phenyl)-L-alanine The title compound was prepared according to the representative procedure of Example 11, Steps 3-4, using (2-((8-(tert-butoxycarbonyl)-1,8-diazaspiro[4.5]decan-1-yl)methyl)-5-(trifluoromethyl)phenyl)-L-alanine in Step 3 to provide (2-((8-(tert-butoxycarbonyl)-1,8-diazaspiro[4.5]decan-1-yl)methyl)-5-(trifluoromethyl)phenyl)-L-alanine as a white solid. $^1$H NMR (300 MHz, Methanol-$d_4$) δ 7.32 (d, J=7.8 Hz, 1H), 6.96-7.30 (m, 2H), 6.12-6.21 (m, 1H), 4.37-4.46 (m, 1H), 4.22-4.25 (m, 2H), 4.09-4.16 (m, 1H), 3.80-3.84 (m, 1H), 3.04-3.30 (m, 2H), 2.90-2.93 (m, 2H), 2.08-2.23 (m, 2H), 1.76-2.03 (m, 6H), 1.48 (d, J=6.9 Hz, 3H). LCMS (ESI, m/z): 580 [M+H]+.

Example 14

4-(3-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)cyclohexane-1-carboxylic acid

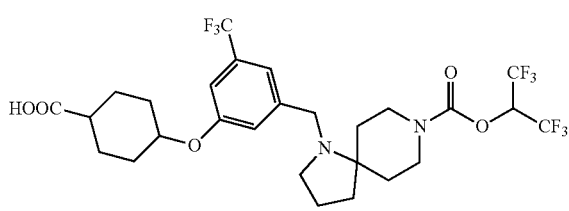 [SMILES: O=C(O)C1CCC(Oc2cc(CN3CCCC34CCN(C(=O)OC(C(F)(F)F)C(F)(F)F)CC4)cc(C(F)(F)F)c2)CC1]

Step 1

Synthesis of ethyl 4-((methylsulfonyl)oxy)cyclohexane-1-carboxylate

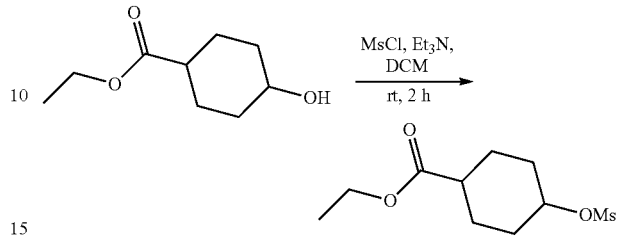

A 40-mL round-bottom flask was charged with ethyl 4-hydroxycyclohexane-1-carboxylate (200 mg, 1.16 mmol, 1.00 equiv), TEA (351 mg, 3.47 mmol, 3.00 equiv), and DCM (10 mL). Methanesulfonyl chloride (158 mg, 1.38 mmol, 1.20 equiv) was added dropwise at 0° C. The resulting solution was stirred for 2 h at room temperature and quenched with water (10 mL). The mixture was extracted with DCM (3×10 mL) and the organic layers were combined, washed with brine (2×10 mL), dried over anhydrous sodium sulfate, filtered and concentrated under reduced pressure to yield 280 mg (96% yield) of ethyl 4-(methanesulfonyloxy)cyclohexane-1-carboxylate as a light yellow oil.

Step 2

Synthesis of tert-butyl 1-(3-hydroxy-5-(trifluoromethyl)benzyl)-1,8-diazaspiro[4.5]decane-8-carboxylate

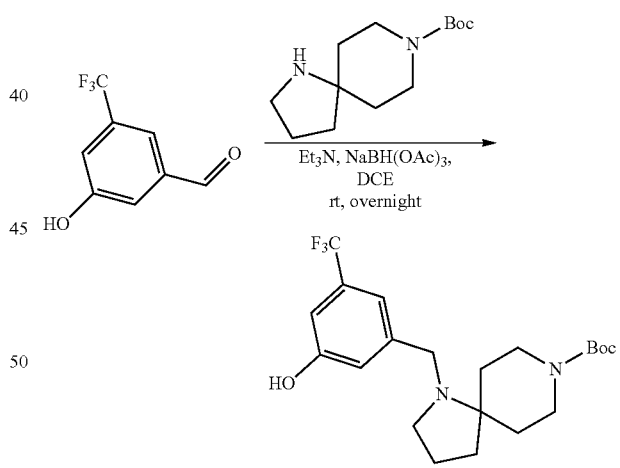

A 40-mL round-bottom flask was charged with 3-hydroxy-5-(trifluoromethyl)benzaldehyde (300 mg, 1.58 mmol, 1.00 equiv), tert-butyl 1,8-diazaspiro[4.5]decane-8-carboxylate (379 mg, 1.58 mmol, 1.00 equiv), and TEA (479 mg, 4.73 mmol, 3.00 equiv) in DCE (10 mL). The resulting solution was stirred for 0.5 h at room temperature. Sodium triacetoxyborohydride (1.00 g, 4.72 mmol, 3.00 equiv) was added, and the mixture was stirred overnight at room temperature and quenched with water (10 mL). The resulting solution was extracted with DCM (3×10 mL) and the organic layers were combined, washed with brine (2×10 mL), dried over anhydrous sodium sulfate, filtered and concentrated under reduced pressure. The residue was chromatographed on a silica gel column with DCM/MeOH (10/1) to yield 520 mg (80% yield) of tert-butyl 1-(3-hydroxy-5-(trifluoromethyl)benzyl)-1,8-diazaspiro[4.5]decane-8-carboxylate as a light yellow oil. LCMS (ESI, m/z): 415 [M+H]⁺.

Step 3

Synthesis of tert-butyl 1-(3-((4-(ethoxycarbonyl)cyclohexyl)oxy)-5-(trifluoromethyl)benzyl)-1,8-diazaspiro[4.5]decane-8-carboxylate

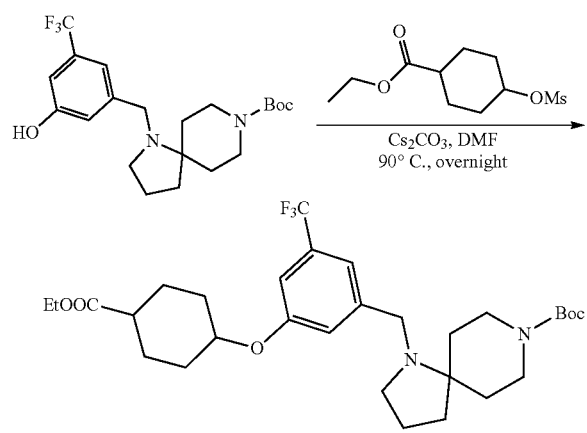

A 100-mL round-bottom flask was charged with tert-butyl 1-(3-hydroxy-5-(trifluoromethyl)benzyl)-1,8-diazaspiro[4.5]decane-8-carboxylate (380 mg, 0.920 mmol, 1.00 equiv), ethyl 4-(methanesulfonyloxy)cyclohexane-1-carboxylate (344 mg, 1.37 mmol, 1.50 equiv), cesium carbonate (898 mg, 2.76 mmol, 3.00 equiv), and N,N-dimethylformamide (10 mL). The resulting solution was stirred overnight at 90° C. and quenched with water (10 mL). The resulting solution was extracted with EtOAc (3×10 mL) and the organic layers were combined, washed with brine (2×10 mL), dried over anhydrous sodium sulfate, filtered and concentrated under reduced pressure. The residue was chromatographed on a silica gel column with EtOAc/petroleum ether (¼) to provide 180 mg (35% yield) of tert-butyl 1-(3-((4-(ethoxycarbonyl)cyclohexyl)oxy)-5-(trifluoromethyl)benzyl)-1,8-diazaspiro[4.5]decane-8-carboxylate as a light yellow oil. LCMS (ESI, m/z): 569 [M+H]⁺.

Step 4

Synthesis of 4-(3-((8-(tert-butoxycarbonyl)-1,8-diazaspiro[4.5]decan-1-yl)methyl)-5-(trifluoromethyl)phenoxy)cyclohexane-1-carboxylic acid

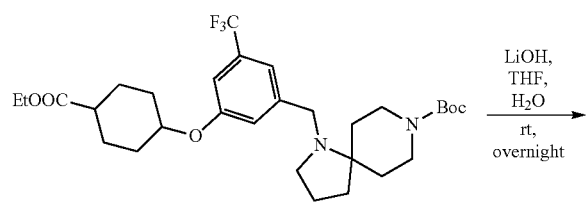

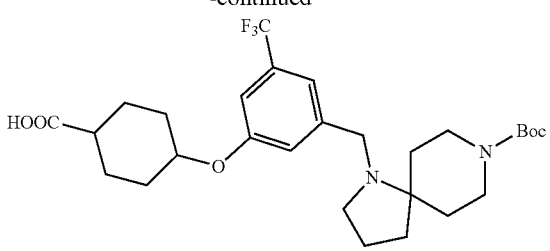

A 100-mL round-bottom flask was charged with tert-butyl 1-(3-((4-(ethoxycarbonyl)cyclohexyl)oxy)-5-(trifluoromethyl)benzyl)-1,8-diazaspiro[4.5]decane-8-carboxylate (180 mg, 0.320 mmol, 1.00 equiv), lithium hydroxide (76.0 mg, 3.17 mmol, 10.0 equiv), tetrahydrofuran (5 mL), and water (3 mL). The resulting solution was stirred overnight at room temperature and quenched with water (10 mL). The pH value of the solution was adjusted to 6 with hydrochloric acid (1M). The resulting solution was extracted with DCM (3×10 mL) and the organic layers were combined, washed with brine (2×10 mL), dried over anhydrous sodium sulfate, filtered and concentrated under reduced pressure to provide 170 mg (99% yield) of 4-(3-((8-(tert-butoxycarbonyl)-1,8-diazaspiro[4.5]decan-1-yl)methyl)-5-(trifluoromethyl)phenoxy)cyclohexane-1-carboxylic acid as a solid. LCMS (ESI, m/z): 541 [M+H]⁺.

Step 5

Synthesis of 4-(3-((1,8-diazaspiro[4.5]decan-1-yl)methyl)-5-(trifluoromethyl)phenoxy)cyclohexane-1-carboxylic acid hydrochloride

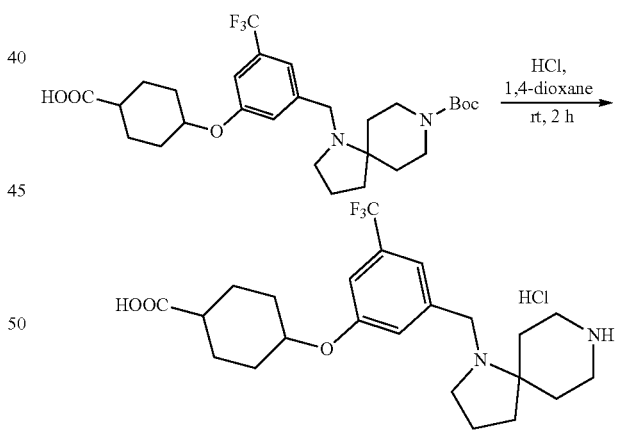

A 50-mL round-bottom flask was charged with 4-(3-((8-(tert-butoxycarbonyl)-1,8 diazaspiro[4.5]decan-1-yl)methyl)-5-(trifluoromethyl)phenoxy)cyclohexane-1-carboxylic acid (170 mg, 0.310 mmol, 1.00 equiv), 1,4-dioxane (10 mL), and hydrochloric acid (2 mL). The resulting solution was stirred for 2 h at room temperature and concentrated under reduced pressure to provide 180 mg (crude) of 4-(3-((1,8-diazaspiro[4.5]decan-1-yl)methyl)-5-(trifluoromethyl)phenoxy)cyclohexane-1-carboxylic acid hydrochloride as a light yellow oil. LCMS (ESI, m/z): 441 [M+H]⁺.

Step 6

Synthesis of 4-(3-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclohexane-1-carboxylic acid

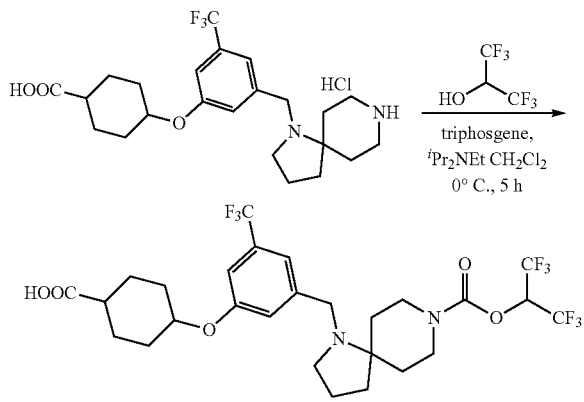

A 40-mL round-bottom flask was charged with 1,1,1,3,3,3-hexafluoropropan-2-ol (79.0 mg, 0.470 mmol, 1.50 equiv), and triphosgene (47.0 mg, 0.160 mmol, 0.50 equiv) in DCM (5 mL) under nitrogen. N,N-Diisopropylethylamine (121 mg, 0.940 mmol, 3.00 equiv) was added dropwise at 0° C. The resulting solution was stirred for 2 h at 0° C. before 4-(3-[1,8-diazaspiro[4.5]decan-1-ylmethyl]-5-(trifluoromethyl)phenoxy)cyclohexane-1-carboxylic acid hydrochloride (138 mg, 0.310 mmol, 1.00 equiv) was added. The resulting solution was stirred for 3 h at 0° C. and quenched with water (10 mL). The mixture was extracted with DCM (3×10 mL) and the organic layers were combined, washed with brine (2×10 mL), dried over anhydrous sodium sulfate, filtered and concentrated under reduced pressure. The crude product (200 mg) was purified by preparative HPLC to afford 12.1 mg (6% yield) of 4-(3-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclohexane-1-carboxylic acid as a white solid. $^1$H NMR (400 MHz, Methanol-$d_4$) δ 7.06-7.54 (m, 3H), 6.15-6.19 (m, 1H), 4.31-4.89 (m, 1H), 4.20-4.23 (m, 2H), 3.34-3.82 (m, 2H), 3.07-3.32 (m, 2H), 2.95 (br, 1H), 2.72-2.76 (m, 1H), 2.20-2.23 (m, 1H), 2.07-2.10 (m, 1H), 1.73-2.00 (m, 11H), 1.52-1.68 (m, 4H). LCMS (ESI, m/z): 635 [M+H]$^+$.

Example 15

4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenoxy)cyclohexane-1-carboxylic acid

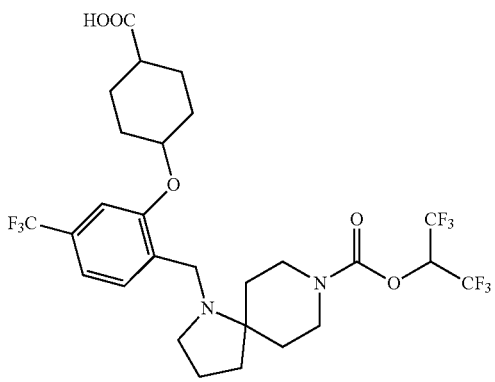 [SMILES: O=C(O)C1CCC(Oc2cc(C(F)(F)F)ccc2CN2CCCC23CCN(C(=O)OC(C(F)(F)F)C(F)(F)F)CC3)CC1]

The title compound was prepared according to the representative procedure of Example 14 using 2-hydroxy-4-(trifluoromethyl)benzaldehyde in Step 2 to provide 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclohexane-1-carboxylic acid as a white solid. $^1$H NMR (400 MHz, Methanol-$d_4$) δ 7.19-7.22 (m, 2H), 7.02-7.08 (m, 1H), 6.13-6.17 (m, 1H), 4.89 (br, 0.2H), 4.35-4.39 (m, 0.8H), 4.15-4.26 (m, 2H), 3.74-3.75 (m, 2H), 3.07-3.18 (m, 2H), 2.77-2.80 (m, 2H), 2.20-2.35 (m, 1H), 2.07-2.19 (m, 3H), 1.76-1.99 (m, 8H), 1.51-1.66 (m, 5H). LCMS (ESI, m/z): 635 [M+H]$^+$.

Example 16

1,1,1,3,3,3-Hexafluoropropan-2-yl 1-(2-((4-(methylsulfonamido)-4-oxobutyl)amino)-4-(trifluoromethyl)benzyl)-1,8-diazaspiro[4.5]decane-8-carboxylate

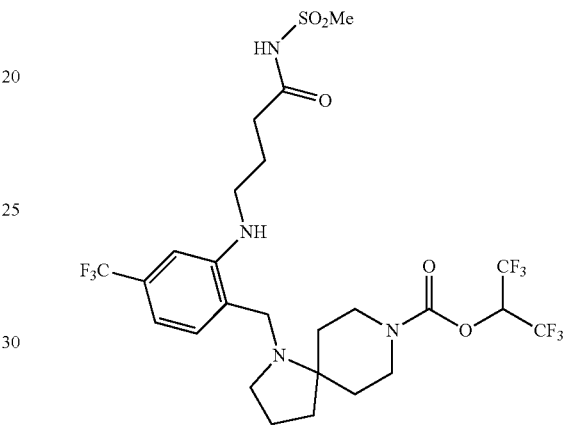

The title compound was prepared according to the representative procedure of Example 11 using tert-butyl 4-aminobutanoate in Step 2 to provide 1,1,1,3,3,3-hexafluoropropan-2-yl 1-(2-((4-(methylsulfonamido)-4-oxobutyl)amino)-4-(trifluoromethyl)benzyl)-1,8-diazaspiro[4.5]decane-8-carboxylate as a white solid. $^1$H NMR (400 MHz, Methanol-$d_4$) δ 7.16 (d, J=7.6 Hz, 1H), 6.83 (d, J=7.6 Hz, 1H), 6.77 (s, 1H), 6.08-6.18 (m, 1H), 4.16-4.22 (m, 2H), 3.72-3.83 (m, 2H), 3.01-3.24 (m, 7H), 2.64 (t, J=7.0 Hz, 2H), 2.45 (t, J=7.2 Hz, 2H), 1.91-1.99 (m, 5H), 1.75-1.90 (m, 3H), 154-1.56 (m, 2H). LCMS (ESI, m/z): 671 [M+H]$^+$.

Example 17

4-(3-Chloro-5-((8-(((1,1,1,3,3,3-hexafluoropropan-2-yl)oxy)carbonyl)-1,8-diazaspiro[4.5]decan-1-yl)methyl)phenoxy)butanoic acid

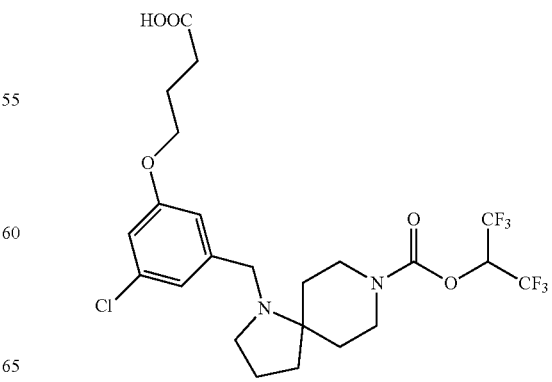

Step 1

Synthesis of tert-butyl 4-(3-chloro-5-formylphenoxy)butanoate

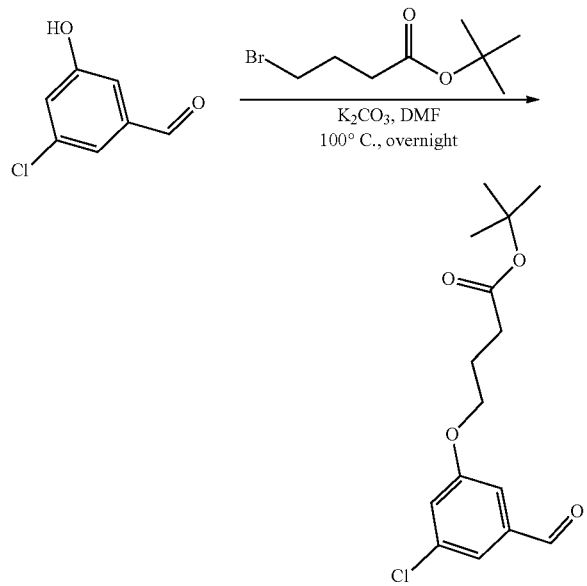

A 50-mL round-bottom flask was charged with 3-chloro-5-hydroxybenzaldehyde (1.00 g, 6.39 mmol, 1.00 equiv), N,N-dimethylformamide (10 mL), potassium carbonate (2.65 g, 19.2 mmol, 3.00 equiv), and tert-butyl 4-bromobutanoate (2.84 g, 12.7 mmol, 2.00 equiv). The resulting solution was stirred overnight at 100° C. and quenched with water (30 mL). The resulting solution was extracted with EtOAc (2×50 mL) and the organic layers were combined, washed with brine (2×30 mL), dried over anhydrous sodium sulfate, filtered and concentrated under reduced pressure. The residue was chromatographed on a silica gel column with DCM/MeOH (98/2) to provide 1.10 g (58%) of tert-butyl 4-(3-chloro-5-formylphenoxy)butanoate as a light yellow oil.

Step 2

Synthesis of 1,1,1,3,3,3-hexafluoropropan-2-yl 1-(3-(4-(tert-butoxy)-4-oxobutoxy)-5-chlorobenzyl)-1,8-diazaspiro[4.5]decane-8-carboxylate

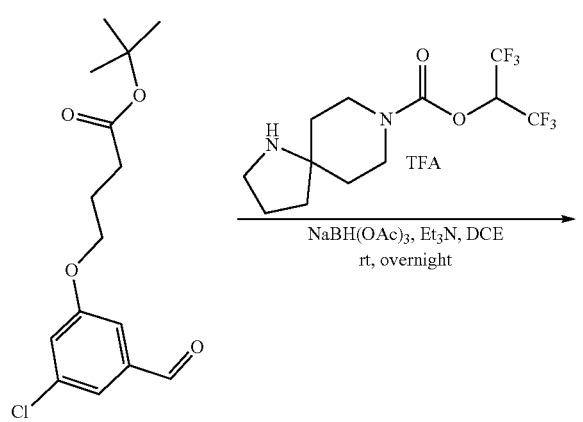

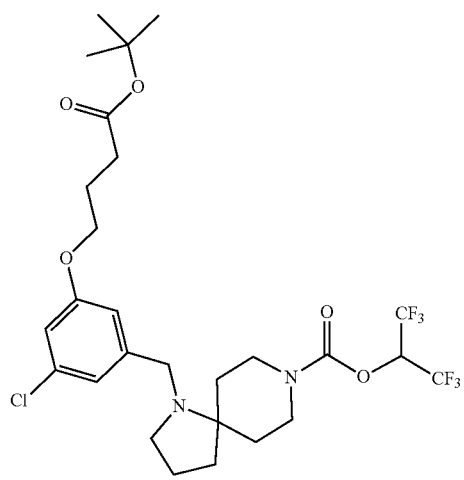

A 50-mL round-bottom flask was charged with tert-butyl 4-(3-chloro-5-formylphenoxy)butanoate (150 mg, 0.500 mmol, 1.00 equiv), DCE (10 mL), TEA (153 mg, 1.50 mmol, 3.00 equiv), and 1,1,1,3,3,3-hexafluoropropan-2-yl 1,8-diazaspiro[4.5]decane-8-carboxylate, 2,2,2-trifluoroacetate salt (Example 1, Step 4; 168 mg, 0.500 mmol, 1.00 equiv), The mixture was stirred for 1 h at room temperature before sodium triacetoxyborohydride (320 mg, 1.50 mmol, 3.00 equiv) was added. The resulting solution was stirred overnight at room temperature and quenched with water (30 mL). The mixture was extracted with DCM (2×50 mL) and the organic layers were combined, washed with brine (2×30 mL), dried over anhydrous sodium sulfate, filtered and concentrated under reduced pressure. The residue was chromatographed on a silica gel column with DCM/MeOH (98/2) to provide 240 mg (77% yield) of 1,1,1,3,3,3-hexafluoropropan-2-yl 1-(3-(4-(tert-butoxy)-4-oxobutoxy)-5-chlorobenzyl)-1,8-diazaspiro[4.5]decane-8-carboxylate as yellow oil. LCMS (ESI, m/z): 617 [M+H]$^+$.

Step 3

Synthesis of 4-(3-chloro-5-((8-(((1,1,1,3,3,3-hexafluoropropan-2-yl)oxy)carbonyl)-1,8-diazaspiro[4.5]decan-1-yl)methyl)phenoxy)butanoic acid

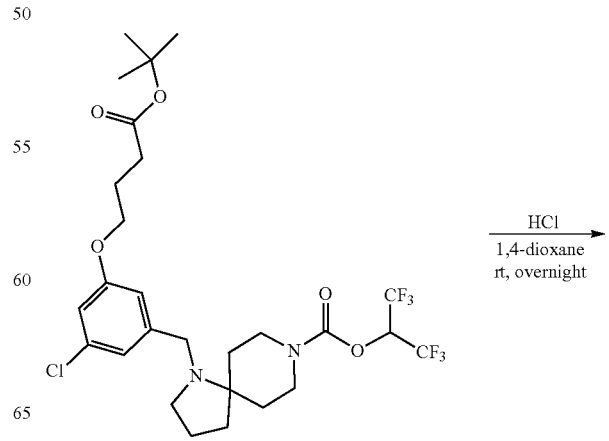

-continued

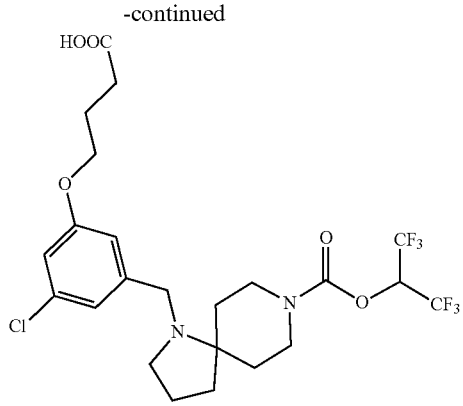

A 50-mL round-bottom flask was charged with 1,1,1,3,3,3-hexafluoropropan-2-yl 1-(3-(4-(tert-butoxy)-4-oxobutoxy)-5-chlorobenzyl)-1,8-diazaspiro[4.5]decane-8-carboxylate (240 mg, 0.390 mmol, 1.00 equiv), 1,4-dioxane (10 mL), and hydrochloric acid (3 mL). The resulting solution was stirred overnight at room temperature and concentrated under reduced pressure. The residue was dissolved in saturated NaHCO₃ solution (30 mL). The resulting solution was extracted with DCM (2×50 mL) and the organic layers were combined, washed with brine (2×30 mL), dried over anhydrous sodium sulfate, filtered and concentrated under reduced pressure. The crude product (300 mg) was purified by preparative HPLC to afford 44.7 mg (20% yield) of 4-(3-chloro-5-((8-(((1,1,1,3,3,3-hexafluoropropan-2-yl)oxy)carbonyl)-1,8-diazaspiro[4.5]decan-1-yl)methyl)phenoxy)butanoic acid as a white solid. ¹H NMR (300 MHz, Methanol-d₄) 6.95 (s, 1H), 6.84-6.87 (m, 2H), 6.09-6.17 (m, 1H), 4.17-4.19 (m, 2H), 4.01 (t, J=6.3 Hz, 2H), 3.68 (s, 2H), 3.05-3.12 (m, 2H), 2.81 (t, J=7.0 Hz, 2H), 2.43 (t, J=7.4 Hz, 2H), 1.94-2.11 (m, 4H), 1.71-1.90 (m, 4H), 1.59-1.61 (m, 2H). LCMS (ESI, m/z): 561 [M+H]⁺.

Example 18

1,1,1,3,3,3-hexafluoropropan-2-yl 1-(2-(4-(methylsulfonamido)-4-oxobutoxy)-4-(trifluoromethyl)benzyl)-1,8-diazaspiro[4.5]decane-8-carboxylate

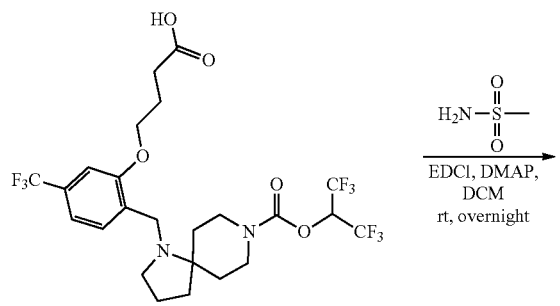

-continued

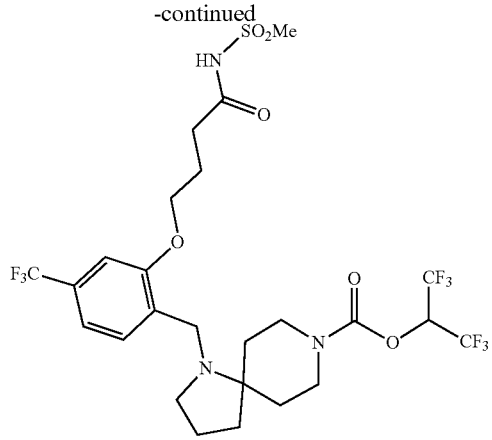

A 50-mL round-bottom flask was charged with 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)butanoic acid (Example 6, Steps 1-3; 200 mg, 0.340 mmol, 1.00 equiv), DCM (10 mL), methanesulfonamide (96.0 mg, 1.01 mmol, 3.00 equiv), 4-dimethylaminopyridine (123 mg, 1.01 mmol, 3.00 equiv), and N-(3-dimethylaminopropyl)-N'-ethylcarbodiimide hydrochloride (129 mg, 0.670 mmol, 2.00 equiv). The resulting solution was stirred overnight at room temperature and quenched with water (30 mL). The mixture was extracted with DCM (2×50 mL) and the organic layers were combined, washed with brine (2×30 mL), dried over anhydrous sodium sulfate, filtered and concentrated under reduced pressure. The crude product (300 mg) was purified by preparative HPLC to afford 52.0 mg (23% yield) of (2-((8-(((1,1,1,3,3,3-hexafluoropropan-2-yl)oxy)carbonyl)-1,8-diazaspiro[4.5]decan-1-yl)methyl)-5-(trifluoromethyl)phenyl)-L-alanine as a white solid. ¹H NMR (300 MHz, Methanol-d₄) δ 7.06 (d, J=8.1 Hz, 1H), 7.26-0.28 (m, 2H), 6.12-6.20 (m, 1H), 4.23-4.31 (m, 2H), 4.16 (t, J=6.0 Hz, 2H), 4.08-4.11 (m, 2H), 3.06-3.21 (m, 7H), 2.46 (t, J=6.9 Hz, 2H), 1.97-2.20 (m, 8H), 1.76-1.80 (m, 2H). LCMS (ESI, m/z): 672 [M+H]⁺.

Example 19

1-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclopropane-1-carboxylic acid

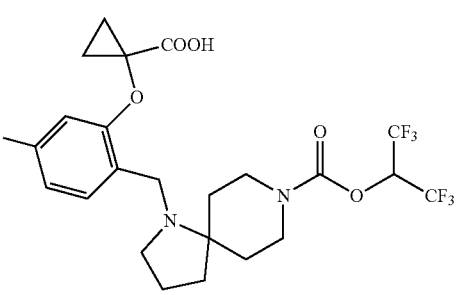

Step 1

Synthesis of methyl 1-(2-formyl-5-(trifluoromethyl)phenoxy)cyclopropane-1-carboxylate

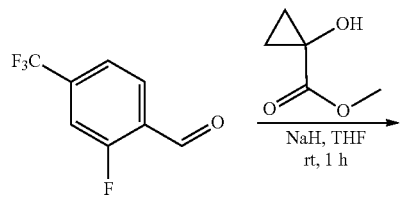

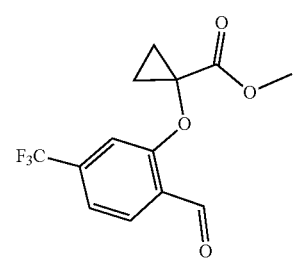

A flask was charged with methyl 1-hydroxycyclopropane-1-carboxylate (1.36 g, 11.7 mmol, 1.50 equiv) and THF (10 mL). Sodium hydride (0.780 g, 19.5 mmol, 2.50 equiv, 60% in mineral oil) was added at 0° C. The mixture was stirred for 20 min at room temperature. 2-Fluoro-4-(trifluoromethyl)benzaldehyde (1.50 g, 7.81 mmol, 1.00 equiv) was added. The resulting solution was stirred for 1 h at room temperature and quenched with water (30 mL). The resulting solution was extracted with DCM (2×50 mL) and the organic layers were combined, washed with brine (2×30 mL), dried over anhydrous sodium sulfate, filtered and concentrated under reduced pressure. The residue was chromatographed on a silica gel column to provide 530 mg (24% yield) of methyl 1-(2-formyl-5-(trifluoromethyl)phenoxy)cyclopropane-1-carboxylate as a yellow oil. $^1$H NMR (300 MHz, Chloroform-d) δ 10.50 (s, 1H), 8.00-7.97 (m, 1H), 7.38-7.27 (m, 2H), 3.79 (s, 3H), 1.82-1.70 (m, 2H), 1.52-1.44 (m, 2H).

Step 2

Synthesis of tert-butyl 1-(2-(1-(methoxycarbonyl)cyclopropoxy)-4-(trifluoromethyl)benzyl)-1,8-diazaspiro[4.5]decane-8-carboxylate

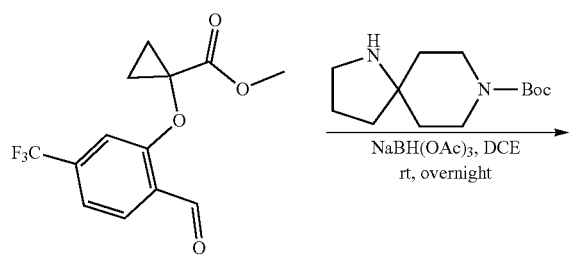

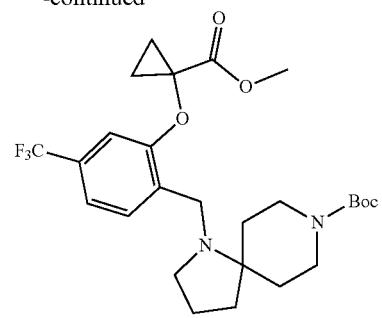

A flask was charged with methyl 1-(2-formyl-5-(trifluoromethyl)phenoxy)cyclopropane-1-carboxylate (530 mg, 1.84 mmol, 1.00 equiv), DCE (10 mL), and tert-butyl 1,8-diazaspiro[4.5]decane-8-carboxylate (530 mg, 2.21 mmol, 1.20 equiv). The mixture was stirred for 1 h at room temperature. Sodium triacetoxyborohydride (1.17 g, 5.52 mmol, 3.00 equiv) was added. The resulting solution was stirred overnight at room temperature and quenched with water (50 mL), as described in Example 7, Step 2. The residue was chromatographed on a silica gel column to provide 350 mg (37% yield) of tert-butyl 1-(2-(1-(methoxycarbonyl)cyclopropoxy)-4-(trifluoromethyl)benzyl)-1,8-diazaspiro[4.5]decane-8-carboxylate as a yellow oil. LCMS (ESI, m/z): 513 [M+H]$^+$.

Step 3

Synthesis of 1-(2-((8-(tert-butoxycarbonyl)-1,8-diazaspiro[4.5]decan-1-yl)methyl)-5-(trifluoromethyl)phenoxy)cyclopropane-1-carboxylic acid

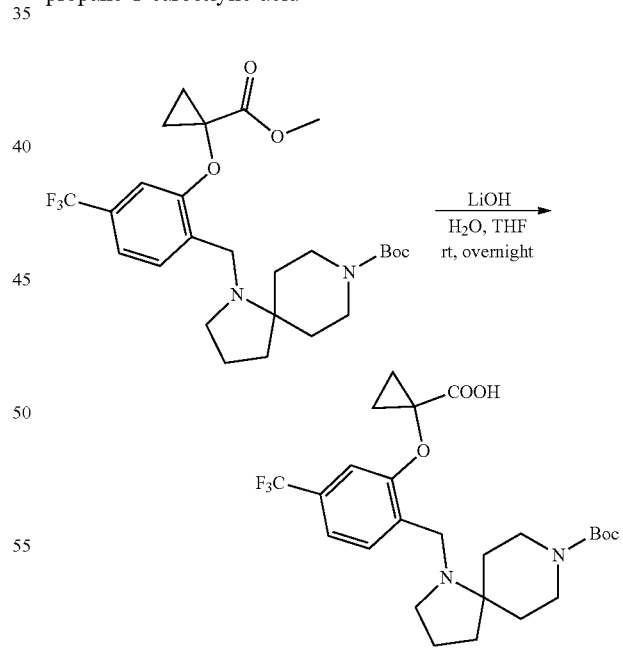

A flask was charged with tert-butyl 1-(2-(1-(methoxycarbonyl)cyclopropoxy)-4-(trifluoromethyl)benzyl)-1,8-diazaspiro[4.5]decane-8-carboxylate (350 mg, 0.680 mmol, 1.00 equiv), water (5 mL), THF and (5 mL), lithium hydroxide (246 mg, 10.2 mmol, 15.0 equiv). The resulting solution was stirred overnight at room temperature. The pH value of the solution was adjusted to 5 with hydrochloric acid (1 mol/L), as described in Example 14, Step 4 to provide 330 mg (97% yield) of 1-(2-((8-(tert-butoxycarbonyl)-1,8-diazaspiro[4.5]decan-1-yl)methyl)-5-(trifluoromethyl)phenoxy)cyclopropane-1-carboxylic acid as a yellow oil. LCMS (ESI, m/z): 499 [M+H]+.

Step 4

Synthesis of 1-(2-((1,8-diazaspiro[4.5]decan-1-yl)methyl)-5-(trifluoromethyl)phenoxy)cyclopropane-1-carboxylic acid

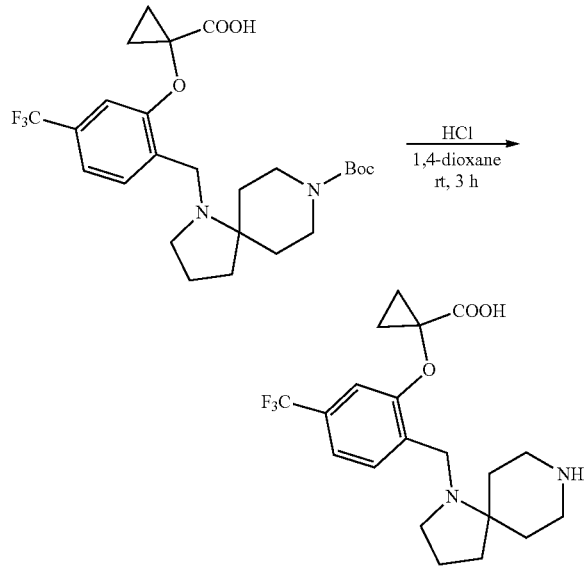

A flask was charged with 1-(2-((8-(tert-butoxycarbonyl)-1,8-diazaspiro[4.5]decan-1-yl)methyl)-5-(trifluoromethyl)phenoxy)cyclopropane-1-carboxylic acid (330 mg, 0.660 mmol, 1.00 equiv), 1,4-dioxane (10 mL), and concentrated hydrochloric acid (2 mL). The resulting solution was stirred for 3 h at room temperature and concentrated under reduced pressure to provide 264 mg (quantitative) of 1-(2-((1,8-diazaspiro[4.5]decan-1-yl)methyl)-5-(trifluoromethyl)phenoxy)cyclopropane-1-carboxylic acid as a yellow oil. LCMS (ESI, m/z): 399 [M+H]+.

Step 5

Synthesis of 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclopropane-1-carboxylic acid

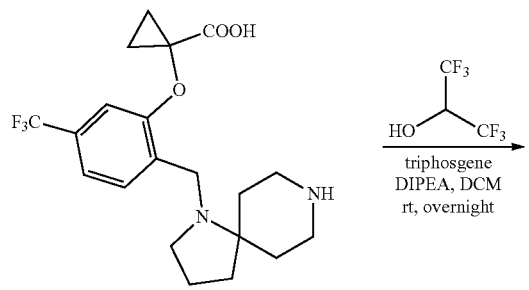

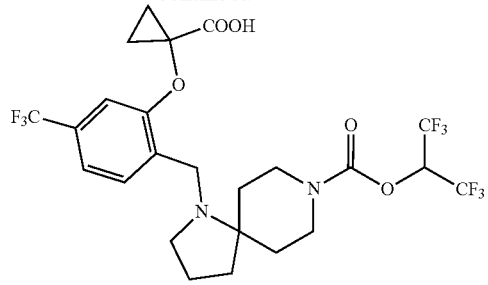

A flask was charged with triphosgene (137 mg, 0.462 mmol, 0.70 equiv), DCM (10 mL), and 1,1,1,3,3,3-hexafluoropropan-2-ol (222 mg, 1.32 mmol, 2.00 equiv). DIPEA (255 mg, 1.98 mmol, 3.00 equiv) was added dropwise at 0° C. The mixture was stirred for 1 h at room temperature. 1-(2-((1,8-Diazaspiro[4.5]decan-1-yl)methyl)-5-(trifluoromethyl)phenoxy)cyclopropane-1-carboxylic acid (264 mg, 0.660 mmol, 1.00 equiv) was added. The resulting solution was stirred overnight at room temperature and quenched with water (30 mL), as described in Example 1, Step 3. The crude product (300 mg) was purified by preparative HPLC to provide 268.6 mg (68% yield) of 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclopropane-1-carboxylic acid as a white solid. 1H NMR (400 MHz, Methanol-d4) δ 7.65-7.58 (m, 2H), 7.36 (d, J=8.0 Hz, 1H), 6.22-6.15 (m, 1H), 4.84 (br, 1H), 4.33-4.26 (m, 2H), 3.84 (br, 1H), 3.48 (br, 1H), 3.31 (br, 1H), 3.31-3.13 (m, 2H), 2.54-2.31 (m, 2H), 2.26-2.19 (m, 3H), 2.10-1.90 (m, 3H), 1.90-1.76 (m, 1H), 1.45-1.43 (m, 1H), 1.28-1.15 (m, 2H). LCMS (ESI, m/z): 593 [M+H]+.

Example 20

1-((5-chloro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid

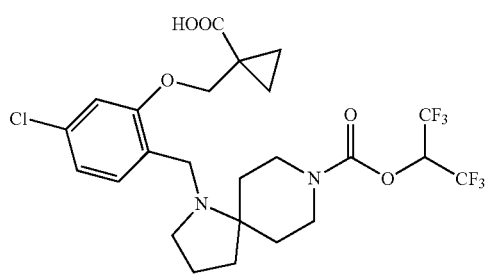 [SMILES: O=C(OC(C(F)(F)F)C(F)(F)F)N1CCC2(CCCN2Cc2ccc(Cl)cc2OCC2(C(=O)O)CC2)CC1]

Step 1

Synthesis of ethyl 1-(((methylsulfonyl)oxy)methyl)cyclopropane-1-carboxylate

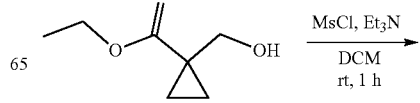

135 / 136 -continued

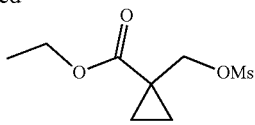

A flask was charged with ethyl 1-(hydroxymethyl)cyclopropane-1-carboxylate (1.20 g, 8.33 mmol, 1.00 equiv), DCM (10 mL), and TEA (2.52 g, 25.0 mmol, 3.00 equiv). Methanesulfonyl chloride (1.42 g, 12.5 mmol, 1.50 equiv) was added at 0° C. The resulting solution was stirred for 1 h at room temperature and quenched with saturated NH$_4$Cl solution (30 mL), as described in Example 14, Step 1, to provide 1.84 g of ethyl 1-(((methylsulfonyl)oxy)methyl)cyclopropane-1-carboxylate as a yellow oil.

Step 2

Synthesis of ethyl 1-((5-chloro-2-formylphenoxy)methyl)cyclopropane-1-carboxylate

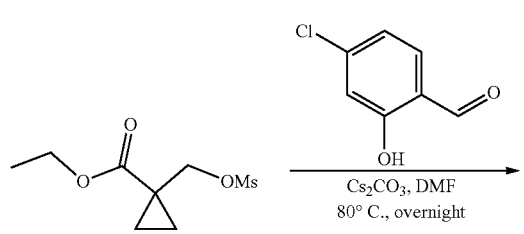

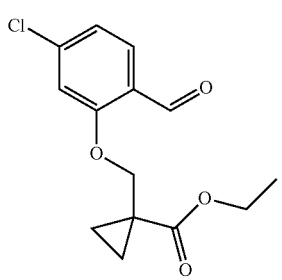

A flask was charged with ethyl 1-(((methylsulfonyl)oxy)methyl)cyclopropane-1-carboxylate (1.07 g, 4.80 mmol, 1.50 equiv), DMF (10 mL), cesium carbonate (3.14 g, 9.60 mmol, 3.00 equiv), and 4-chloro-2-hydroxybenzaldehyde (500 mg, 3.20 mmol, 1.00 equiv). The resulting solution was stirred overnight at 80° C. and quenched with water (50 mL), as described in Example 14, Step 3. The residue was chromatographed on a silica gel column to provide 800 mg (89% yield) of ethyl 1-((5-chloro-2-formylphenoxy)methyl)cyclopropane-1-carboxylate as a yellow oil. LCMS (ESI, m/z): 283 [M+H]$^+$.

Step 3

Synthesis of tert-butyl 1-(4-chloro-2-((1-(ethoxycarbonyl)cyclopropyl)methoxy)benzyl)-1,8-diazaspiro[4.5]decane-8-carboxylate

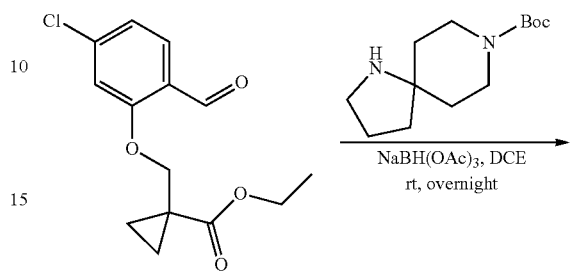

A flask was charged with ethyl 1-((5-chloro-2-formylphenoxy)methyl)cyclopropane-1-carboxylate (0.800 g, 2.83 mmol, 1.00 equiv), DCE (10 mL), and tert-butyl 1,8-diazaspiro[4.5]decane-8-carboxylate (0.816 g, 3.40 mmol, 1.20 equiv). The mixture was stirred for 1 h at room temperature. Sodium triacetoxyborohydride (1.80 g, 8.49 mmol, 3.00 equiv). The resulting solution was stirred overnight at room temperature and quenched with water (50 mL), as described in Example 7, Step 2. The residue was chromatographed on a silica gel column to provide 0.800 g (56% yield) of tert-butyl 1-(4-chloro-2-((1-(ethoxycarbonyl)cyclopropyl)methoxy)benzyl)-1,8-diazaspiro[4.5]decane-8-carboxylate as a yellow oil. LCMS (ESI, m/z): 507 [M+H]$^+$.

Step 4

Synthesis of 1-((2-((8-(tert-butoxycarbonyl)-1,8-diazaspiro[4.5]decan-1-yl)methyl)-5-chlorophenoxy)methyl)cyclopropane-1-carboxylic acid

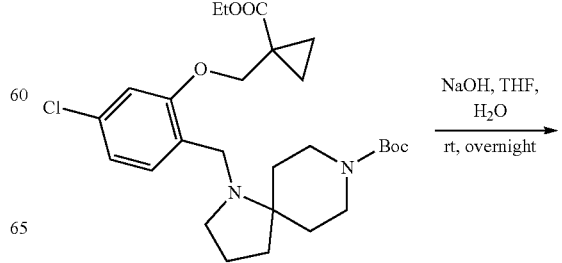

-continued

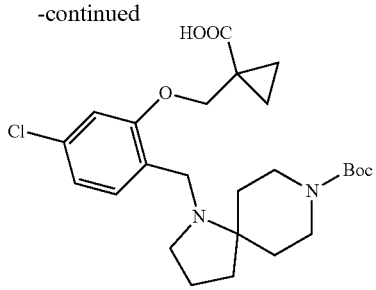

A flask was charged with tert-butyl 1-(4-chloro-2-((1-(ethoxycarbonyl)cyclopropyl)methoxy)benzyl)-1,8-diazaspiro[4.5]decane-8-carboxylate (350 mg, 0.690 mmol, 1.00 equiv), THF (5 mL), water (5 mL), and sodium hydroxide (277 mg, 6.92 mmol, 10.0 equiv). The resulting solution was stirred overnight at room temperature. The pH value of the solution was adjusted to 5 with hydrochloric acid (1 mol/L). The resulting solution was extracted with DCM (2×50 mL) and the organic layers were combined, washed with brine (2×30 mL), dried over anhydrous sodium sulfate, filtered and concentrated under reduced pressure to provide 270 mg (82% yield) of 1-((2-((8-(tert-butoxycarbonyl)-1,8-diazaspiro[4.5]decan-1-yl)methyl)-5-chlorophenoxy)methyl)cyclopropane-1-carboxylic acid as a yellow oil. LCMS (ESI, m/z): 479 [M+H]+.

Step 5

Synthesis of 1-((2-((1,8-diazaspiro[4.5]decan-1-yl)methyl)-5-chlorophenoxy)methyl)cyclopropane-1-carboxylic acid

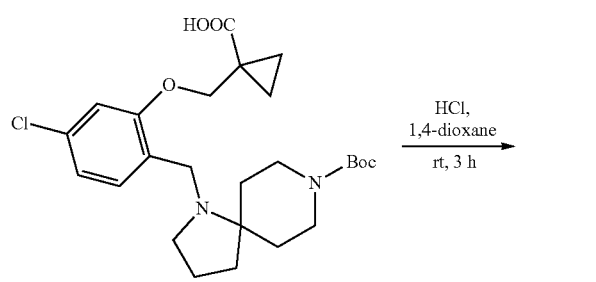

A flask was charged with 1-[2-([8-[(tert-butoxy)carbonyl]-1,8-diazaspiro[4.5]decan-1-yl]methyl)-5-chlorophenoxymethyl]cyclopropane-1-carboxylic acid (270 mg, 0.560 mmol, 1.00 equiv), concentrated hydrochloric acid (5 mL), and 1,4-dioxane (5 mL). The resulting solution was stirred for 3 h at room temperature filtered and concentrated under reduced pressure to provide 211 mg (quantitative) of 1-((2-((1,8-diazaspiro[4.5]decan-1-yl)methyl)-5-chlorophenoxy)methyl)cyclopropane-1-carboxylic acid as a brown oil. LCMS (ESI, m/z): 379 [M+H]+.

Step 6

Synthesis of 1-((5-chloro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid

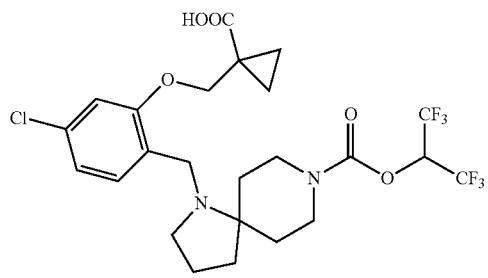

A flask was charged with triphosgene (118 mg, 0.400 mmol, 0.70 equiv), DCM (10 mL), and 1,1,1,3,3,3-hexafluoropropan-2-ol (190 mg, 1.13 mmol, 2.00 equiv). DIPEA (220 mg, 1.71 mmol, 3.00 equiv) was added at 0° C. The mixture was stirred for 1 h at room temperature. 1-((2-((1,8-Diazaspiro[4.5]decan-1-yl)methyl)-5-chlorophenoxy)methyl)cyclopropane-1-carboxylic acid (214 mg, 0.560 mmol, 1.00 equiv) was added. The resulting solution was stirred overnight at room temperature and quenched with saturated NaHCO3 solution (30 mL), as described in Example 1, Step 3. The crude product (300 mg) was purified by preparative HPLC to provide 86.1 mg (27% yield) of 1-((5-chloro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid as a white solid. 1H NMR (300 MHz, Chloroform-d) δ 7.18 (d, J=8.1 Hz, 1H), 6.94-6.89 (m, 2H), 5.81-5.57 (m, 1H), 4.30-4.15 (m, 2H), 4.12-4.05 (m, 2H), 3.84-3.74 (m, 2H), 3.00-2.92 (m, 4H), 2.21-2.16 (m, 2H), 2.04-1.08 (m, 6H), 1.36-1.34 (m, 2H), 0.86-0.82 (m, 2H). LCMS (ESI, m/z): 573 [M+H]+.

Examples 21-25

Examples 21-25 were prepared by similar procedures as described in Examples 1-20 (Table 2).

TABLE 2

| Ex | Name | Structure | NMR (¹H NMR, 300 MHz or 400 MHz) | MS [M + H]⁺ |
|---|---|---|---|---|
| 21 | 3-((3-((8-(((1,1,1,3,3,3-hexafluoropropan-2-yl)oxy)carbonyl)-1,8-diazaspiro[4.5]decan-1-yl)methyl)-5-(trifluoromethyl)phenyl)amino)propanoic acid | 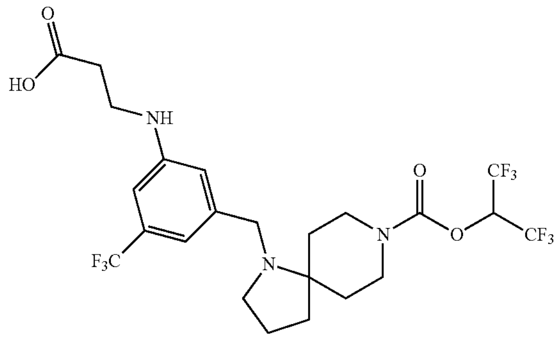 [SMILES: O=C(O)CCNc1cc(CN2CCCC23CCN(C(=O)OC(C(F)(F)F)C(F)(F)F)CC3)cc(C(F)(F)F)c1] | (Methanol-d₄) δ 6.97-6.89 (m, 2H), 6.83 (s, 1H), 6.20-6.16 (m, 1H), 4.26 (br, 2H), 3.85 (s, 2H), 3.46-3.32 (m, 2H), 3.18-2.98 (m, 4H), 2.58-2.54 (m, 2H), 2.10-1.96 (m, 6H), 1.72-1.67 (m, 2H) | 580.5 |
| 22 | 1-((2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)methyl)cyclopropane-1-carboxylic acid | 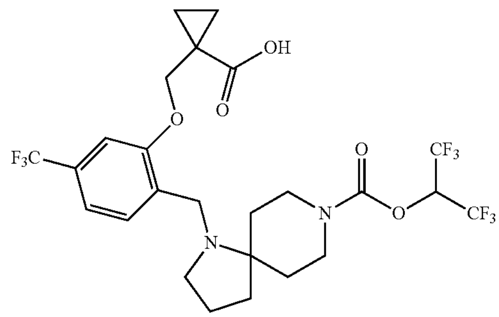 [SMILES: O=C(OC(C(F)(F)F)C(F)(F)F)N1CCC2(CCCN2Cc2ccc(C(F)(F)F)cc2OCC2(C(=O)O)CC2)CC1] | (Methanol-d₄) δ 7.59-7.56 (m, 1H), 7.30-7.29 (m, 2H), 6.21-6.13 (m, 1H), 4.26-4.18 (m, 4H), 3.27-3.08 (m, 4H), 2.38-2.33 (m, 2H), 2.15-1.87 (m, 6H), 1.26-1.22 (m, 2H), 0.90-0.89 (m, 2H) | 607.5 |
| 23 | 1-((4-fluoro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid | 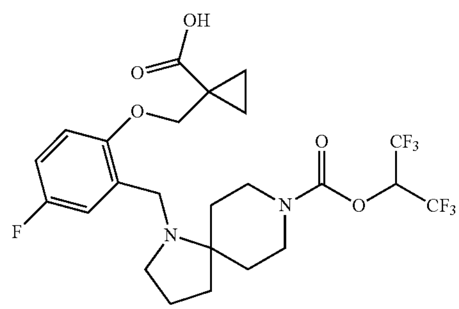 [SMILES: O=C(OC(C(F)(F)F)C(F)(F)F)N1CCC2(CCCN2Cc2cc(F)ccc2OCC2(C(=O)O)CC2)CC1] | (Chloroform-d) δ 7.06-6.94 (m, 2H), 6.85-6.80 (m, 1H), 5.79-5.70 (m, 1H), 4.29-4.21 (m, 2H), 4.14-4.02 (m, 2H), 3.84-3.73 (m, 2H), 3.07-2.92 (m, 4H), 2.18-2.13 (m, 2H), 2.03-1.80 (m, 6H), 1.36-1.33 (m, 2H), 0.87-0.83 (m, 2H) | 557.1 |
| 24 | 1-((5-fluoro-2-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid | 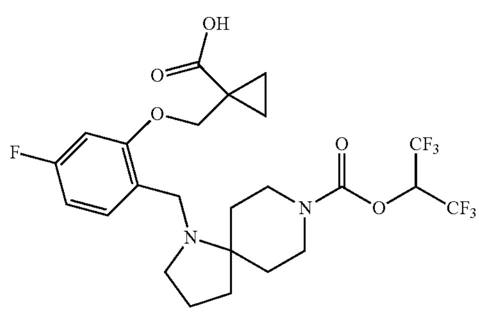 [SMILES: O=C(OC(C(F)(F)F)C(F)(F)F)N1CCC2(CCCN2Cc2ccc(F)cc2OCC2(C(=O)O)CC2)CC1] | (Chloroform-d) δ 7.34-7.26 (m, 1H), 6.69-6.63 (m, 2H), 5.80-5.72 (m, 1H), 4.36-4.26 (m, 2H), 4.14-4.06 (m, 2H), 3.95 (br, 2H), 3.14-3.00 (m, 4H), 2.38-2.33 (m, 2H), 2.15-1.87 (m, 6H), 1.37 (br, 2H), 0.86-0.85 (br, 2H) | 557.2 |
| 25 | 1-((2-fluoro-6-((8-(((1,1,1,3,3,3-hexafluoropropan-2-yl)oxy)carbonyl)-1,8-diazaspiro[4.5]decan-1-yl)methyl)phenoxy)methyl)cyclopropane-1-carboxylic acid | 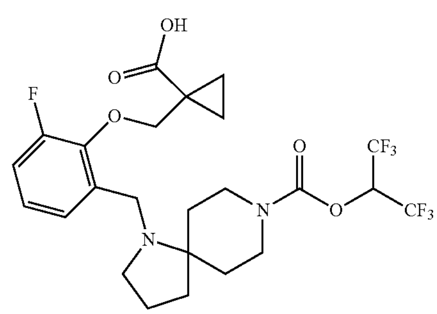 [SMILES: O=C(OC(C(F)(F)F)C(F)(F)F)N1CCC2(CCCN2Cc2cccc(F)c2OCC2(C(=O)O)CC2)CC1] | (Chloroform-d) δ 7.12-7.00 (m, 2H), 6.99-6.93 (m, 1H), 5.80-5.72 (m, 1H), 4.38-4.01 (m, 4H), 3.97 (br, 1H), 3.80 (br, 1H), 3.06-2.96 (m, 4H), 2.23-2.17 (m, 2H), 2.06-1.97 (m, 3H), 1.85 (br, 3H), 1.41-1.35 (m, 2H), 0.96-0.93 (m, 2H) | 557.1 |

II. Biological Evaluation

Compounds were tested to assess their MAGL and serine hydrolase activity using the following in vitro and in vivo assays.

In Vitro Competitive Activity-Based Protein Profiling (Human).

Proteomes (human prefrontal cortex or cell membrane fractions) (50 µL, 1.0-2.0 mg/mL total protein concentration) were preincubated with varying concentrations of inhibitors at 37° C. After 30 min, FP-Rh or JW912 (1.0 µL, 50 µM in DMSO) was added and the mixture was incubated for another 30 min at room temperature. Reactions were quenched with SDS loading buffer (15 µL-4×) and run on SDS-PAGE. Following gel imaging, serine hydrolase activity was determined by measuring fluorescent intensity of gel bands corresponding to MAGL using ImageJ 1.49 k software. $IC_{50}$ data from this assay is shown in Table 3.

In Vitro Competitive Activity-Based Protein Profiling (Mouse).

Proteomes (mouse brain membrane fraction or cell lysates) (50 µL, 1.0 mg/mL total protein concentration) were preincubated with varying concentrations of inhibitors at 37° C. After 30 min, FP-Rh (1.0 µL, 50 µM in DMSO) was added and the mixture was incubated for another 30 min at 37° C. Reactions were quenched with SDS loading buffer (50 µL-4×) and run on SDS-PAGE. Following gel imaging, serine hydrolase activity was determined by measuring fluorescent intensity of gel bands corresponding to MAGL using ImageJ 1.49 k software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44). Percent inhibition data from this assay is shown in Table 3.

TABLE 3

| Ex | MAGL $IC_{50}$ (µM) (human) | MAGL % inh. 5 mg/kg (mouse) |
|---|---|---|
| 1 | *** | A |
| 2 | *** | |
| 3 | *** | |
| 4 | *** | A |
| 5 | *** | |
| 6 | *** | A |
| 7 | *** | D |
| 8 | * | |
| 9 | *** | A |
| 10 | *** | B |
| 11 | *** | |
| 12 | *** | A |
| 13 | *** | A |
| 14 | *** | A |
| 15 | *** | |
| 16 | *** | |
| 17 | *** | |
| 18 | *** | A |
| 19 | *** | D |
| 20 | ** | |
| 21 | *** | A |

TABLE 3-continued

| Ex | MAGL $IC_{50}$ (µM) (human) | MAGL % inh. 5 mg/kg (mouse) |
|---|---|---|
| 22 | *** | D |
| 23 | * | |
| 24 | * | |
| 25 | * | |

* $IC_{50}$ is less than or equal to 100 nM;  $IC_{50}$ is greater than 100 nM and less than 1 µM; * $IC_{50}$ is greater than or equal to 1 µM and less than or equal to 10 µM.
A = % inhibition is greater than or equal to 75%; B = % inhibition is greater than or equal to 50% and less than 75%; C = % inhibition is greater than or equal to 25% and less than 50%; D = % inhibition is greater than or equal to 0% and less than 25%.

We claim:

1. A compound having the structure of Formula (I):

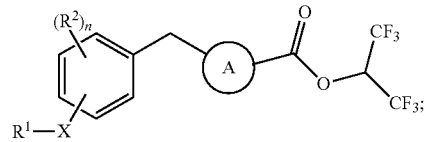

Formula (I)

wherein:

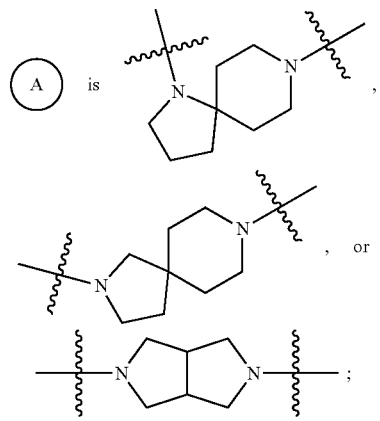

$X$ is —O—, —S—, —$SO_2$—, —N($R^3$)—, or —$CH_2$—;
$Y$ is —O— or —N($R^7$)—;
$R^1$ is —($CR^4R^5$)$_m$—$R^6$, —($CR^4R^5$)$_p$—Y—($CR^4R^5$)$_q$—$R^6$, or —($CR^4R^5$)$_t$—$C_{3-6}$cycloalkyl—$R^6$;
each $R^2$ is independently selected from halogen, —CN, $C_{1-6}$alkyl, $C_{1-6}$haloalkyl, —$C_{1-6}$ alkyl(heterocycloalkyl), —$OR^{17}$, and —C(O)$NR^{18}R^{19}$;
$R^3$ is H or $C_{1-6}$alkyl;
each $R^4$ and $R^5$ is each independently selected from H, F, and $C_{1-6}$alkyl; or $R^4$ and $R^5$, together with the carbon to which they are attached, form a $C_{3-6}$cycloalkyl ring;
$R^6$ is —$CO_2R^9$, —C(O)$R^{10}$, or —C(O)O—($CR^{12}R^{13}$)—OC(O)$R^{11}$;
$R^7$ is H, $C_{1-6}$alkyl, or —$SO_2R^8$;
$R^8$ is $C_{1-6}$alkyl;
$R^9$ is H or $C_{1-6}$alkyl;
$R^{10}$ is $C_{1-6}$alkyl or —$NHSO_2R^{21}$;
$R^{11}$ is $C_{1-6}$alkyl or $C_{1-6}$alkoxy;
$R^{12}$ and $R^{13}$ is each independently H or $C_{1-6}$alkyl;
each $R^{17}$ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl—C(O)(heterocycloalkyl), optionally substituted heterocycloalkyl, optionally substituted aryl, and optionally substituted heteroaryl;

each $R^{18}$ and $R^{19}$ is independently selected from H, $C_{1-6}$alkyl, $C_{1-6}$haloalkyl, cycloalkyl, aryl, and heteroaryl; or $R^{18}$ and $R^{19}$, together with the nitrogen to which they are attached, form a heterocycloalkyl ring optionally substituted with one, two, or three $R^{20}$;

each $R^{20}$ is independently selected from halogen, $C_{1-6}$alkyl, $C_{1-6}$haloalkyl, oxo, —CN, and $C_{3-6}$cycloalkyl;

$R^{21}$ is $C_{1-6}$alkyl;

m is 1, 2, 3 or 4;

n is 0, 1, 2, 3, or 4;

p is 2, 3, or 4;

q is 1, 2, or 3; and t is 0, 1, or 2;

or a pharmaceutically acceptable salt thereof.

2. The compound of claim 1, or a pharmaceutically acceptable salt thereof, wherein $R^1$ is —$(CR^4R^5)_m$—$R^6$.

3. The compound of claim 1, or a pharmaceutically acceptable salt thereof, wherein m is 1, 2, or 3.

4. The compound of claim 1, or a pharmaceutically acceptable salt thereof, wherein each $R^4$ and $R^5$ is H.

5. The compound of claim 1, or a pharmaceutically acceptable salt thereof, wherein $R^6$ is —$CO_2R^9$.

6. The compound of claim 5, or a pharmaceutically acceptable salt thereof, wherein $R^9$ is H.

7. The compound of claim 1, or a pharmaceutically acceptable salt thereof, wherein X is —O—.

8. The compound of claim 1, or a pharmaceutically acceptable salt thereof, wherein

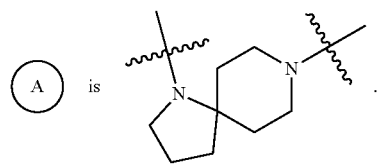

9. The compound of claim 1, or a pharmaceutically acceptable salt thereof, wherein each $R^2$ is independently selected from halogen, $C_{1-6}$alkyl, and $C_{1-6}$haloalkyl.

10. The compound of claim 1, or a pharmaceutically acceptable salt thereof, wherein n is 1.

11. The compound of claim 10, or a pharmaceutically acceptable salt thereof, wherein $R^2$ is —$CF_3$.

12. The compound of claim 1 selected from:

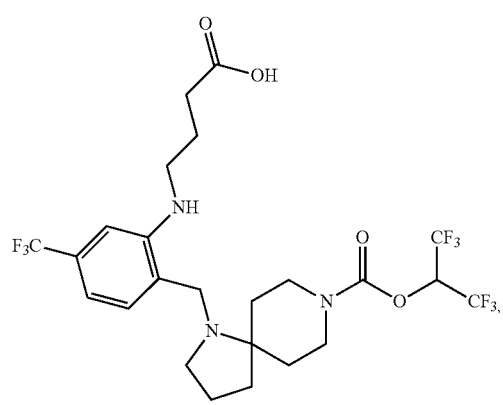

-continued

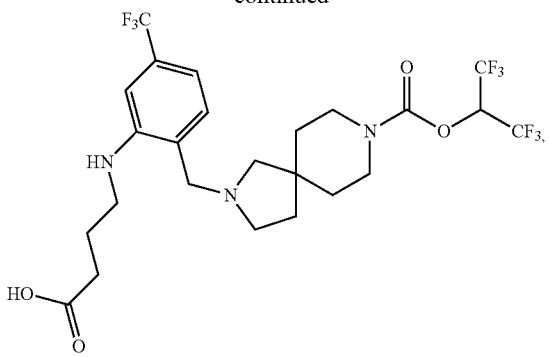

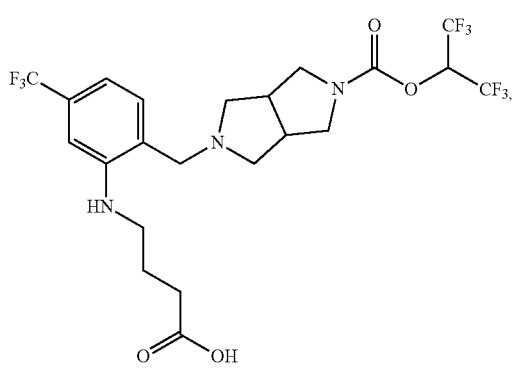

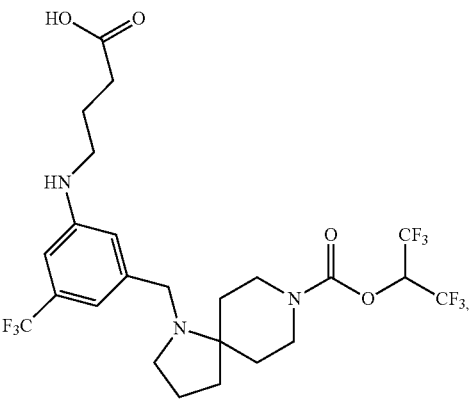

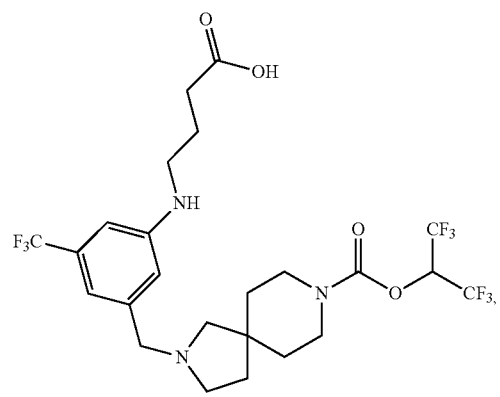

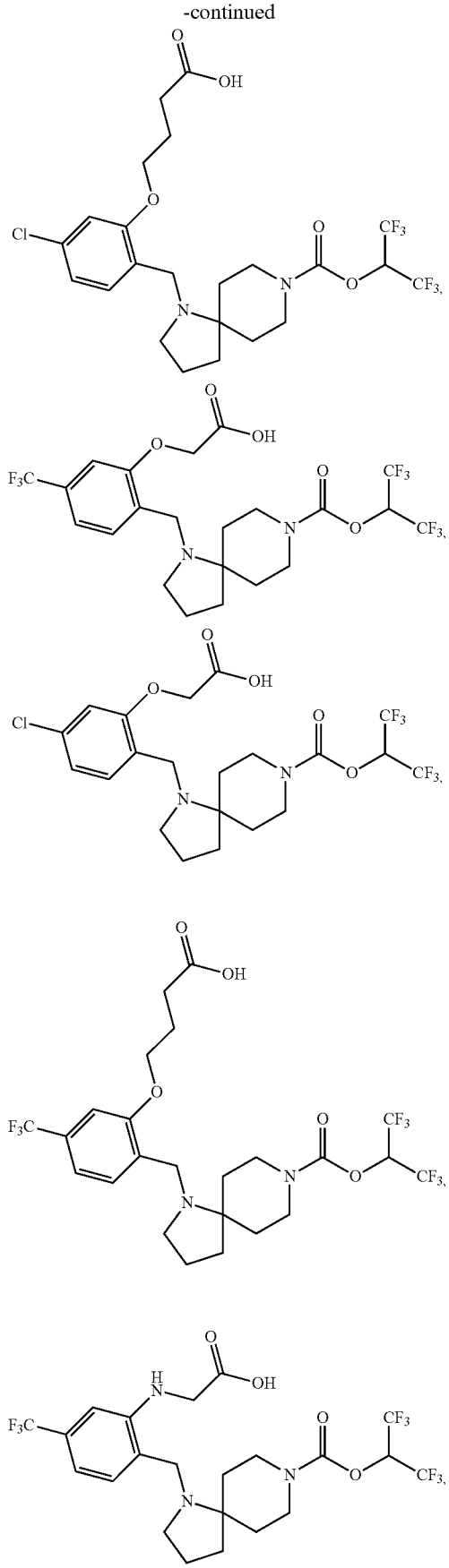

-continued
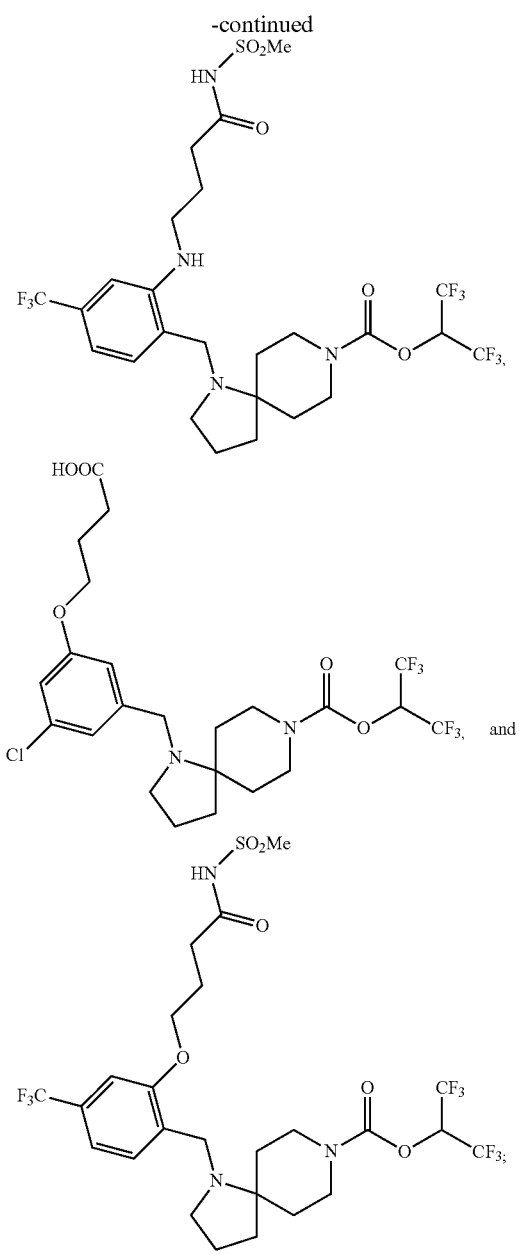
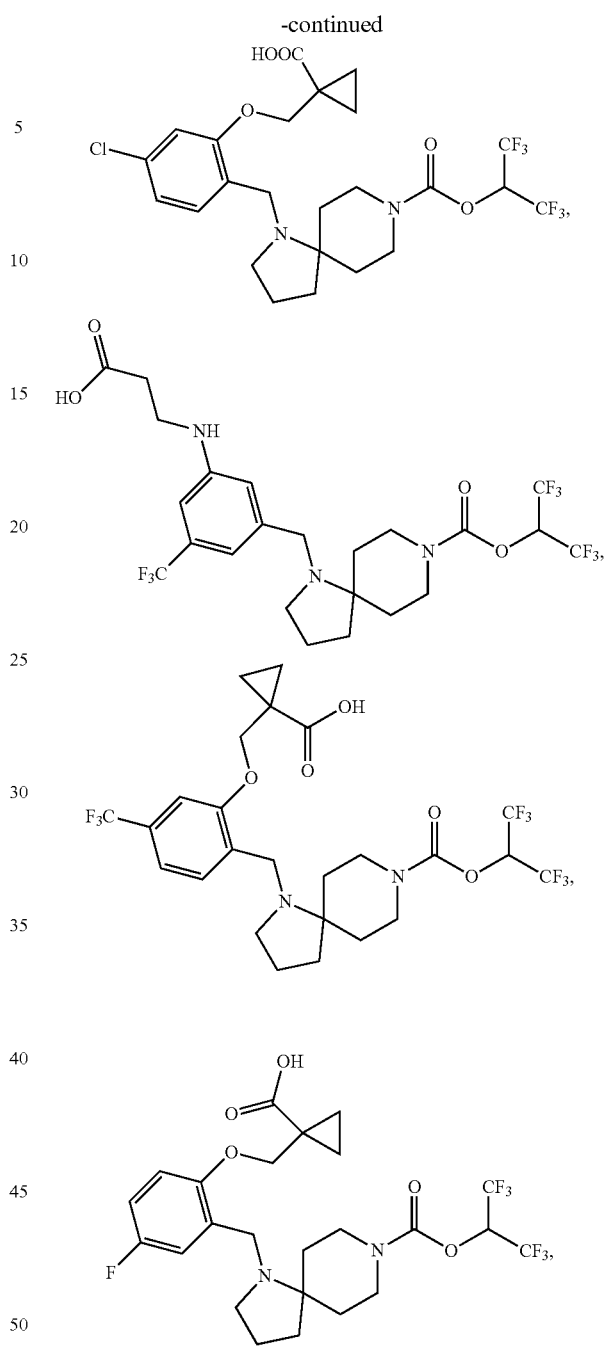
or a pharmaceutically acceptable salt thereof.
13. The compound of claim 1 selected from:
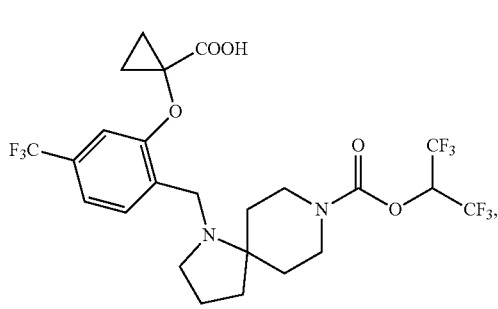

-continued

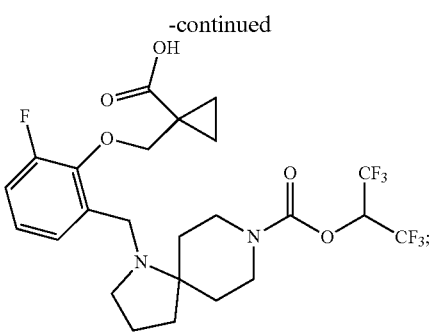

or a pharmaceutically acceptable salt thereof.

14. A pharmaceutical composition comprising a compound of claim 1, or a pharmaceutically acceptable salt thereof, and at least one pharmaceutically acceptable excipient.

15. The compound of claim 1, or a pharmaceutically acceptable salt thereof, selected from 2-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)acetic acid.

16. The compound of claim 1, or a pharmaceutically acceptable salt thereof, selected from 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)butanoic acid.

17. The compound of claim 1, or a pharmaceutically acceptable salt thereof, selected from 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)cyclopropane-1-carboxylic acid.

18. The compound of claim 1, or a pharmaceutically acceptable salt thereof, selected from 1-((2-((8-(((1,1,1,3,3,3-hexafluoropropan-2-yl)oxy)carbonyl)-1,8-diazaspiro[4.5]decan-1-yl)methyl)-5-(trifluoromethyl)phenoxy)methyl)cyclopropane-1-carboxylic acid.

* * * * *